United States Patent
Takagaki et al.

(10) Patent No.: US 6,670,391 B2
(45) Date of Patent: Dec. 30, 2003

(54) BENZOPYRAN DERIVATIVE AND ANTIALLERGIC AGENT

(75) Inventors: Hidetsugu Takagaki, Sakura (JP); Shingo Tanabe, Matsudo (JP); Nobuyuki Kimura, Sakura (JP); Yasuo Aoki, Yotsukaido (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 10/178,238

(22) Filed: Jun. 25, 2002

(65) Prior Publication Data

US 2003/0096860 A1 May 22, 2003

(30) Foreign Application Priority Data

Jun. 28, 2001 (JP) ........................ 2001-196462

(51) Int. Cl.[7] .............................. A61K 31/35
(52) U.S. Cl. ...................... 514/457; 549/285
(58) Field of Search ................ 514/457; 549/285

(56) References Cited

U.S. PATENT DOCUMENTS

| | | | |
|---|---|---|---|
| 4,845,121 A | 7/1989 | Witiak et al. | 514/455 |
| 5,428,059 A | 6/1995 | Takagaki et al. | 514/457 |
| 5,525,595 A | 6/1996 | Takagaki et al. | 514/27 |
| 5,580,552 A | 12/1996 | Takagaki et al. | 514/27 |
| 5,981,495 A | 11/1999 | Takagaki et al. | 514/25 |

FOREIGN PATENT DOCUMENTS

| | | |
|---|---|---|
| EP | 0 598 117 A1 | 5/1994 |
| EP | 0 684 255 A1 | 11/1995 |
| EP | 0 796 854 A1 | 9/1997 |
| JP | 8-92086 | 4/1996 |
| JP | 8-259556 | 10/1996 |
| JP | 9-95446 | 4/1997 |
| JP | 10-245391 | 9/1998 |

OTHER PUBLICATIONS

Takagaki, H. et al, 'Preparation of benzopyrans for treating heart disease' CA 127:307301 (1997) Same as EP 796854.*
Witiak et al., J. Med. Chem., vol. 31, p. 1437–1445, 1998.

* cited by examiner

*Primary Examiner*—Amelia Owens
(74) *Attorney, Agent, or Firm*—Armstrong, Westerman & Hattori, LLP

(57) ABSTRACT

The present invention provides a compound which is highly safe in terms of toxicity and has a stronger antiallergic action, and particularly has an action of inhibiting both immediate and delayed type allergic reactions. A benzopyran derivative represented by the general formula (I):

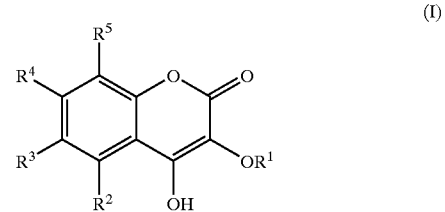

(I)

wherein $R^1$ is an alkyl group having 1–10 carbon atoms or an alkenyl group having 2–10 carbon atoms, and one of $R^2$, $R^3$, $R^4$, and $R^5$ is an alkoxy group substituted with a hydroxy group or an alkoxy group substituted with a carboxy group, and the others are hydrogen atoms or physiologically acceptable salts thereof are superior as the active ingredient of an antiallergic agent.

19 Claims, 1 Drawing Sheet

BENZOPYRAN DERIVATIVE AND ANTIALLERGIC AGENT

BACKGROUND OF THE INVENTION

1. Field of the Invention

The present invention relates to an antiallergic agent containing a benzopyran derivative or physiologically acceptable salts thereof as the active ingredient, and a benzopyran derivative which is useful as an antiallergic agent.

2. Description of Related Art

PCT International Publication No. WO92/13852 (U.S. Pat. No. 5,428,059) discloses that a benzopyran derivative represented by the general formula (III):

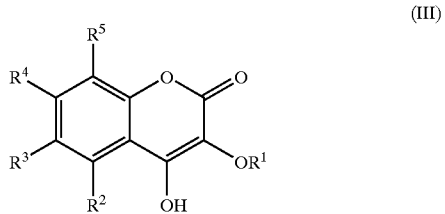

(III)

wherein $R^1$ is an alkyl group having 1–10 carbon atoms or an alkenyl group having 2–10 carbon atoms, and one of $R^2$, $R^3$, $R^4$, and $R^5$ is an alkoxy group and the others are hydrogen atoms, and physiologically acceptable salts thereof are compounds which are useful as antiallergic agents, also have low toxicity, and are highly safe.

Also, Japanese Unexamined Patent Application, First Publication No. Hei 7-145189 (U.S. Pat. No. 5,525,595) discloses a benzopyran derivative wherein a glycosyl group is introduced into the 3-position of benzopyran. Japanese Unexamined Patent Application, First Publication No. Hei 7-145190 (U.S. Pat. No. 5,525,595) discloses a benzopyran derivative wherein a glycosyl group is introduced into the 4-position of benzopyran. Japanese Unexamined Patent Application, First Publication No. Hei 8-198890 (U.S. Pat. No. 5,580,552) discloses a benzopyran derivative wherein a glycosyl group is introduced into the 7-position of benzopyran. The benzopyran derivatives and physiologically acceptable salts thereof are compounds which are useful as antiallergic agents, also have markedly low toxicity, and are highly safe.

Compounds have hitherto been required which have a stronger antiallergic action, particularly an action of inhibiting both immediate and delayed type allergic reactions while maintaining the safeness of these benzopyran derivatives in terms of toxicity.

Japanese Unexamined Patent Application, First Publication No. Hei 9-315967 (U.S. Pat. No. 5,981,495) discloses, as a benzopyran derivative other than those described above, a benzopyran derivative represented by the general formula (IV):

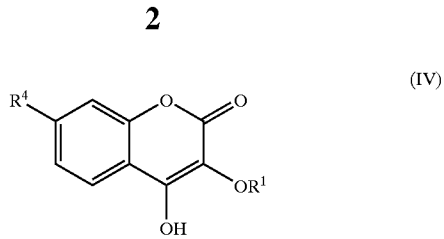

(IV)

wherein $R^1$ is an alkyl group having 1–10 carbon atoms or an alkenyl group having 2–10 carbon atoms, and $R^4$ is an alkoxy group having 1–4 carbon atoms substituted with a hydroxy group.

This benzopyran derivative is useful as a treatment for heart disease. However, it was not known that the compound described in this publication has an excellent antiallergic action.

In Donald T. Witiak et al., J. Med. Chem., Vol. 31, p. 1437–1445, 1988, and U.S. Pat. No. 4,845,121, a benzopyran derivative represented by the general formula (V):

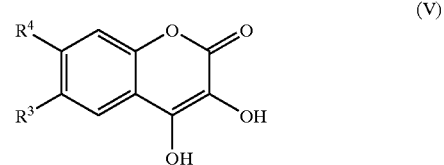

(V)

wherein $R^3$ and $R^4$ are hydrogen atoms, halogen atoms, hydroxy groups, and alkyl groups having 1 to 6 carbon atoms, with the exception that both $R^3$ and $R^4$ are hydrogen atoms, is disclosed as being useful as an antithrombotic agent. However, it was not known that the compounds described in these publications are effective in treating both immediate and delayed type allergies and are also markedly useful as drugs with fewer side effects.

BRIEF SUMMARY OF THE INVENTION

An object to be achieved by the present invention is to provide a compound which is highly safe in terms of toxicity and has a stronger antiallergic action, and particularly has an action of inhibiting both immediate and delayed type allergic reactions.

To achieve the above object, the present invention provides an antiallergic agent including a benzopyran derivative represented by the general formula (I):

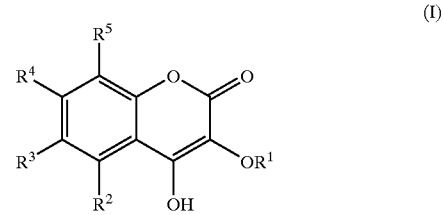

(I)

wherein $R^1$ is an alkyl group having 1–10 carbon atoms or an alkenyl group having 2–10 carbon atoms, and one of $R^2$, $R^3$, $R^4$, and $R^5$ is an alkoxy group substituted with a hydroxy group or an alkoxy group substituted with a carboxy group, and the others are hydrogen atoms, or physiologically acceptable salts thereof as the active ingredient.

In addition, to achieve the above object, the present invention provides a benzopyran derivative represented by the general formula (II):

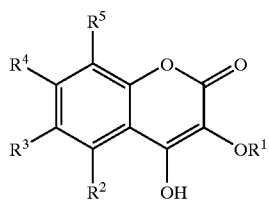

(II)

wherein $R^1$ is an alkyl group having 1–10 carbon atoms or an alkenyl group having 2–10 carbon atoms, and one of $R^2$, $R^3$, $R^4$, and $R^5$ is an alkoxy group substituted with a carboxy group, and the others are hydrogen atoms.

The antiallergic agent including the benzopyran derivative represented by the general formula (I) or physiologically acceptable salts thereof as the active ingredient of the present invention is highly safe in terms of toxicity, and has an antiallergic action which is stronger than that of various benzopyran derivatives as reported previously by the present inventors. It also exerts an excellent effect against both immediate and delayed type allergic diseases such as asthma.

Also, the benzopyran derivative represented by the general formula (II) of the present invention is highly safe in terms of toxicity, and is useful as a drug, particularly as an antiallergic agent.

DETAILED DESCRIPTION OF THE INVENTION

Figure 1:
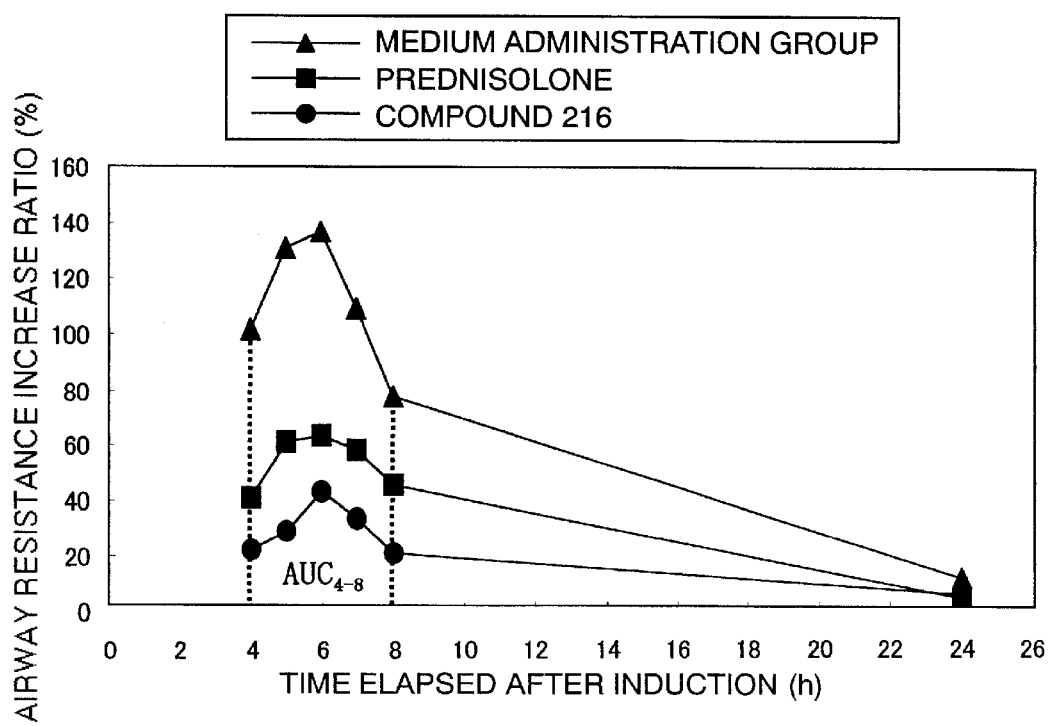
FIG. 1 is a graph showing the relationship between the airway resistance increase ratio up to 4–8 hours after inducing a delayed type asthmatic reaction and time in the asthmatic reaction inducing medium administration group (group wherein a test drug is not administered after inducing the asthmatic reaction), the positive control prednisolone administration group, and compound (216) administration group, and also shows the area under the curve ($AUC_{4-8}$).

In the benzopyran derivative represented by the general formula (I) and the benzopyran derivative represented by the general formula (II) of the present invention, the alkyl group having 1–10 carbon atoms of $R^1$ may be a straight chain alkyl group or a branched alkyl group, and examples of the alkyl group include a methyl group, ethyl group, propyl group, isopropyl group, n-butyl group, s-butyl group, t-butyl group, n-pentyl group, n-hexyl group, 2-methylpentyl group, n-heptyl group, 1-ethylpentyl group, 4-methylpentyl group, 1-ethylbutyl group, n-octyl group, 1-ethylhexyl group, n-decyl group, and n-dodecyl group.

Similarly, the alkenyl group having 2–10 carbon atoms of $R^1$ may be a straight chain alkenyl group or a branched alkenyl group, and examples of the alkenyl group include a vinyl group, propenyl group, pentenyl group, hexenyl group, heptenyl group, octenyl group, nonyl group, decenyl group, 3-methyl-2-butenyl group, and geranyl group. Among these alkenyl groups, an alkenyl group having 4–8 carbon atoms is particularly preferred.

In the benzopyran derivative represented by the general formula (I) and the benzopyran derivative represented by the general formula (II) of the present invention, examples of the alkoxy group substituted with a hydroxy group represented by one of $R^2$, $R^3$, $R^4$, and $R^5$ include a 2-hydroxyethoxy group, 3-hydroxypropyloxy group, 4-hydroxybutoxy group, 2,3-dihydroxypropyloxy group, and 3,4-dihydroxybutoxy group. Among these groups, an alkoxy group having 1–4 carbon atoms is preferred, and an alkoxy group substituted with one or two hydroxy groups is particularly preferred.

Similarly, examples of the alkoxy group substituted with a carboxy group represented by one of $R^2$, $R^3$, $R^4$, and $R^5$ include a 1-hydroxycarbonylmethoxy group, 2-hydroxycarbonylethoxy group, 3-hydroxycarbonylpropyloxy group, and 4-hydroxycarbonylbutoxy group. Among these groups, an alkoxy group having 1–4 carbon atoms excluding a moiety of the carboxy group is preferred, and an alkoxy group substituted with one carboxy group is particularly preferred.

The following summarizes a process for the production of the benzopyran derivative represented by the general formula (I) or the benzopyran derivative represented by the general formula (II) used in the present invention.

The benzopyran derivatives represented by the general formulas (I) and (II) can be produced, for example, in the following manner in accordance with the following reaction:

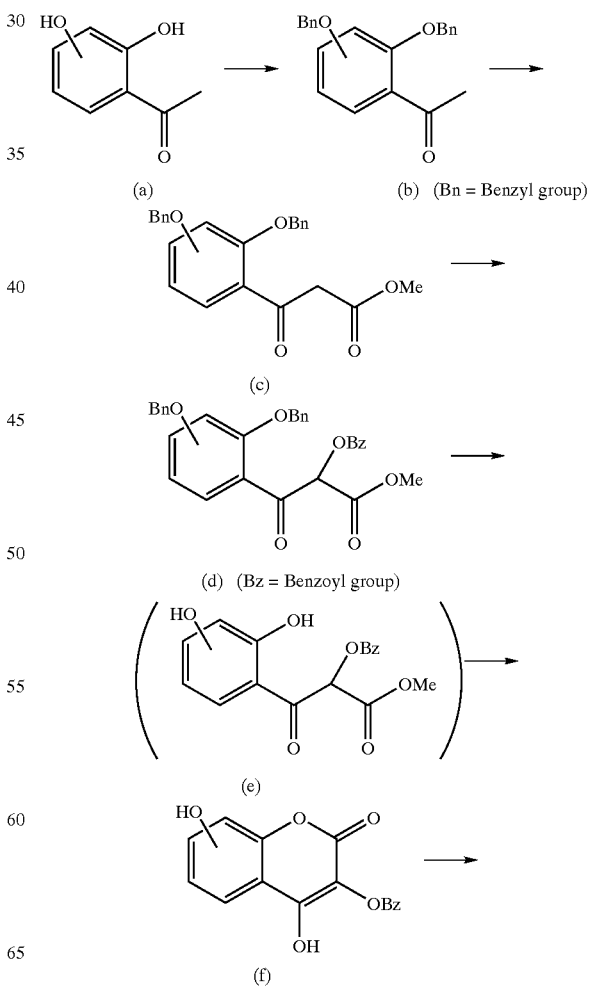

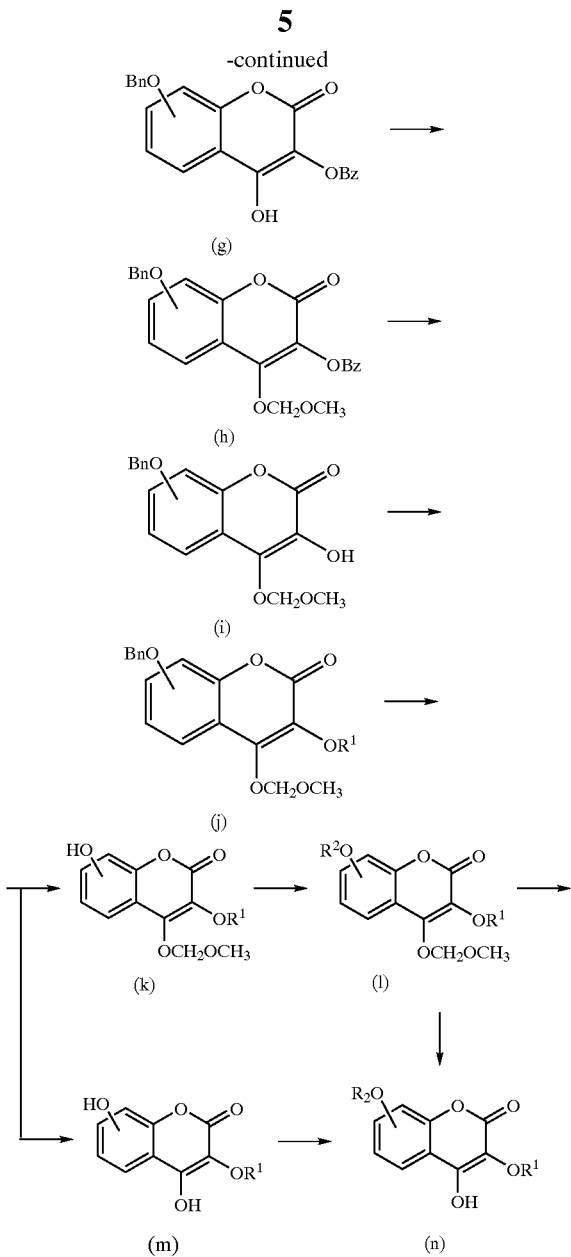

In the reaction scheme, first, the hydroxy group of dihydroxyacetophenone (a) is protected with a benzyl group to obtain compound (b). Next, a condensation reaction between compound (b) and dimethyl carbonate is carried out to obtain a keto ester compound (c) which is subsequently reacted with benzoyl peroxide to obtain compound (d). At this stage, the benzyl group used as a protecting group of the hydroxy group is deprotected by hydrocracking and then treated with an acid to obtain a benzoyloxy compound (f).

Furthermore, the hydroxy group on the aromatic ring of the thus-obtained benzoyloxy compound (f) was protected with the benzyl group to obtain compound (g), and then a methoxymethyl group was introduced at the 4-position to obtain compound (h). The benzoyl group was eliminated from compound, and the hydroxy group at the 3-position was alkylated to obtain compound (j). The alkylation of the hydroxy group can be carried out by a conventional alkylation reaction due to a reaction with a halogenated alkyl, a sulfate ester, or an aryl sulfonate ester. Then, the protecting group of the hydroxy group on the aromatic ring is deprotected with compound (k).

To obtain the benzopyran derivative represented by the general formula (I) wherein $R^2$ is an alkoxy group substituted with a hydroxy group, the hydroxy group on the aromatic ring of compound (k) or compound (m) may be alkoxylated with an alkylating agent wherein a portion of hydrogen atoms are substituted with a protected hydroxy group, and then the deprotection reaction of the protected hydroxy group may be carried out.

To explain the process for the production of the benzopyran derivatives represented by the general formulas (I) and (II) in more detail, a process for the production of the benzopyran derivative wherein the hydroxy group on the benzene ring is alkoxylated with a 2-hydroxyethyl group will be explained below.

First, an alkoxylation reaction is carried out by reacting compound (k) with brominated 2-acetoxyethyl in an organic solvent in the presence of a basic substance.

Examples of the basic substance as used herein include inorganic salts such as sodium hydrogencarbonate, sodium carbonate, potassium hydrogencarbonate, potassium carbonate, sodium hydroxide, and potassium hydroxide; metal alcoholates such as sodium methoxide, sodium ethoxide, sodium t-butoxide, and potassium t-butoxide; and metal hydrides such as sodium hydride and potassium hydride.

Examples of the organic solvent as used herein include hydrocarbon solvents such as benzene, toluene, and xylene; ether solvents such as diethyl ether, tetrahydrofuran, and 1,2-dimethoxyethane; and amide solvents such as N,N-dimethylformamide, N,N-dimethylacetamide, and 1-methyl-2-pyrrolidinone.

The reaction temperature in the above reaction is preferably 0–100° C., and particularly preferably 20–50° C. The reaction time in the above reaction is usually 1–5 hours.

If necessary, the acetyl group as the protecting group is deprotected. This reaction may be carried out by the deacetylation reaction under conventional basic conditions. In such a manner, the desired benzopyran derivative wherein the hydroxy group on the aromatic ring is alkylated with a 2-hydroxyethyl group can be produced.

To obtain the benzopyran derivative represented by the general formula (I), which has an alkoxy group substituted with two hydroxy groups, an isopropylidene group can also be used as the protecting group of two hydroxy groups. When using an alkylating agent protected with the isopropylidene group, the alkylation reaction of the hydroxy group of the benzopyran derivative can be carried out in the same manner as described above. After the completion of the alkylation reaction of the hydroxy group, the deprotection method may be carried out by a conventional deprotection method of the isopropylidene group, and, for example, the reaction is carried out in an aqueous acetic acid solution or hydrochloric acid-dioxane at room temperature or with heating, thus making it possible to produce the desired benzopyran derivative which has an alkoxy group having two hydroxy groups.

To obtain the benzopyran derivatives of the general formulas (I) and (II) wherein $R^2$ is an alkoxy group substituted with a carboxy group, the hydroxy group on the aromatic ring of compound (k) or compound (m) may be alkoxylated by an alkylating agent wherein a portion of hydrogen atoms are substituted with a protected carboxy group, and then a deprotection reaction may be carried out. Next, the process for the production of a benzopyran derivative wherein the hydroxy group on the benzene ring is alkoxylated by a hydroxycarbonylmethyl group will be explained.

First, alkoxylation is carried out by reacting the hydroxy group of compound (k) or compound (m) with ethyl bromoacetate in an organic solvent in the presence of a basic substance.

Examples of the basic substance used in the above reaction include inorganic salts such as sodium hydrogencarbonate, sodium carbonate, potassium hydrogencarbonate, potassium carbonate, sodium hydroxide, and potassium hydroxide; metal alcoholates such as sodium methoxide, sodium ethoxide, sodium t-butoxide, and potassium t-butoxide; and metal hydrides such as sodium hydride and potassium hydride.

Examples of the organic solvent used in the above reaction include hydrocarbon solvents such as benzene, toluene, and xylene; ether solvents such as diethyl ether, tetrahydrofuran, and 1,2-dimethoxyethane; and amide solvents such as N,N-dimethylformamide, N,N-dimethylacetamide, and 1-methyl-2-pyrrolidinone.

The reaction temperature in the above reaction is preferably 0–100° C., and particularly preferably 20–50° C. The reaction time in the above reaction is usually 1–5 hours.

If necessary, the carboxy group having a protecting group is deprotected. This reaction may be carried out by the deprotection reaction under conventional basic conditions. In such a manner, the desired benzopyran derivative wherein the hydroxy group on the aromatic ring is alkoxylated with a hydroxycarbonyl group can be produced.

In the benzopyran derivatives represented by the general formulas (I) and (II), where $R^1$ is an alkenyl group, the hydroxy group may be alkenyloxylated using a halogenated alkenyl or an arylsulfonate ester in the presence of a basic substance by conventional techniques in place of alkoxylation of the hydroxy group at the 3-position in the above process.

Specific examples of the benzopyran derivative represented by the general formula (I) and the benzopyran derivative represented by the general formula (II) used in the present invention include the following compounds:
3-methoxy-4-hydroxy-5-(2-hydroxyethoxy)-2H-1-benzopyran-2-one (compound (1)), 3-ethoxy-4-hydroxy-5-(2-hydroxyethoxy)-2H-1-benzopyran-2-one (compound (2)), 3-propyloxy-4-hydroxy-5-(2-hydroxyethoxy)-2H-1-benzopyran-2-one (compound (3)), 3-isopropyloxy-4-hydroxy-5-(2-hydroxyethoxy)-2H-1-benzopyran-2-one (compound (4)), 3-butoxy-4-hydroxy-5-(2-hydroxyethoxy)-2H-1-benzopyran-2-one (compound (5)), 3-(s-butoxy)-4-hydroxy-5-(2-hydroxyethoxy)-2H-1-benzopyran-2-one (compound (6)), 3-pentyloxy-4-hydroxy-5-(2-hydroxyethoxy)-2H-1-benzopyran-2-one (compound (7)), 3-hexyloxy-4-hydroxy-5-(2-hydroxyethoxy)-2H-1-benzopyran-2-one (compound (8)), 3-(2-methylpentyloxy)-4-hydroxy-5-(2-hydroxyethoxy)-2H-1-benzopyran-2-one (compound (9)), 3-heptyloxy-4-hydroxy-5-(2-hydroxyethoxy)-2H-1-benzopyran-2-one (compound (10)), 3-(1-ethylpentyloxy)-4-hydroxy-5-(2-hydroxyethoxy)-2H-1-benzopyran-2-one (compound (11)), 3-(4-ethylpentyloxy)-4-hydroxy-5-(2-hydroxyethoxy)-2H-1-benzopyran-2-one (compound (12)), 3-(1-ethylbutoxy)-4-hydroxy-5-(2-hydroxyethoxy)-2H-1-benzopyran-2-one (compound (13)), 3-octyloxy-4-hydroxy-5-(2-hydroxyethoxy)-2H-1-benzopyran-2-one (compound (14)), 3-(1-ethylhexyloxy)-4-hydroxy-5-(2-hydroxyethoxy)-2H-1-benzopyran-2-one (compound (15)), 3-decyloxy-4-hydroxy-5-(2-hydroxyethoxy)-2H-1-benzopyran-2-one (compound (16)), 3-vinyloxy-4-hydroxy-5-(2-hydroxyethoxy)-2H-1-benzopyran-2-one (compound (17)), 3-(1-propenyloxy)-4-hydroxy-5-(2-hydroxyethoxy)-2H-1-benzopyran-2-one (compound (18)), 3-(1-butenyloxy)-4-hydroxy-5-(2-hydroxyethoxy)-2H-1-benzopyran-2-one (compound (19)), 3-(1-hexenyloxy)-4-hydroxy-5-(2-hydroxyethoxy)-2H-1-benzopyran-2-one (compound (20)), 3-(1-octenyloxy)-4-hydroxy-5-(2-hydroxyethoxy)-2H-1-benzopyran-2-one (compound (21)), 3-(1-decenyloxy)-4-hydroxy-5-(2-hydroxyethoxy)-2H-1-benzopyran-2-one (compound (22)), 3-(3-methyl-2-butenyloxy)-4-hydroxy-5-(2-hydroxyethoxy)-2H-1-benzopyran-2-one (compound (23)), 3-geranyloxy-4-hydroxy-5-(2-hydroxyethoxy)-2H-1-benzopyran-2-one (compound (24)), 3-prenyloxy-4-hydroxy-5-(2-hydroxyethoxy)-2H-1-benzopyran-2-one (compound (25)), 3-methoxy-4-hydroxy-5-(3-hydroxypropyloxy)-2H-1-benzopyran-2-one (compound (26)), 3-ethoxy-4-hydroxy-5-(3-hydroxypropyloxy)-2H-1-benzopyran-2-one (compound (27)), 3-butoxy-4-hydroxy-5-(3-hydroxypropyloxy)-2H-1-benzopyran-2-one (compound (28)), 3-hexyloxy-4-hydroxy-5-(3-hydroxypropyloxy)-2H-1-benzopyran-2-one (compound (29)), 3-(2-methylpentyloxy)-4-hydroxy-5-(3-hydroxypropyloxy)-1-benzopyran-2-one (compound (30)), 3-octyloxy-4-hydroxy-5-(3-hydroxypropyloxy)-2H-1-benzopyran-2-one (compound (31)), 3-decyloxy-4-hydroxy-5-(3-hydroxypropyloxy)-2H-1-benzopyran-2-one (compound (32)), 3-(1-propenyloxy)-4-hydroxy-5-(3-hydroxypropyloxy)-2H-1-benzopyran-2-one (compound (33)), 3-(1-octenyloxy)-4-hydroxy-5-(3-hydroxypropyloxy)-2H-1-benzopyran-2-one (compound (34)), 3-geranyloxy-4-hydroxy-5-(3-hydroxypropyloxy)-2H-1-benzopyran-2-one (compound (35)), 3-ethoxy-4-hydroxy-5-(4-hydroxybutoxy)-2H-1-benzopyran-2-one (compound (36)), 3-4-hydroxy-5-(4-hydroxybutoxy)-2H-1-benzopyran-2-one (compound (37)), 3-(s-butoxy)-4-hydroxy-5-(4-hydroxybutoxy)-2H-1-benzopyran-2-one (compound (38)), 3-hexyloxy-4-hydroxy-5-(4-hydroxybutoxy)-2H-1-benzopyran-2-one (compound (39)), 3-(1-ethylpentyloxy)-4-hydroxy-5-(4-hydroxybutoxy)-2H-1-benzopyran-2-one (compound (40)), 3-octyloxy-4-hydroxy-5-(4-hydroxybutoxy)-2H-1-benzopyran-2-one (compound (41)), 3-(1-butenyloxy)-4-hydroxy-5-(4-hydroxybutoxy)-2H-1-benzopyran-2-one (compound (42)), 3-prenyloxy-4-hydroxy-5-(4-hydroxybutoxy)-2H-1-benzopyran-2-one (compound (43)), 3-ethoxy-4-hydroxy-5-(2,3-dihydroxypropyloxy)-2H-1-benzopyran-2-one (compound (44)), 3-butoxy-4-hydroxy-5-(2,3-dihydroxypropyloxy)-2H-1-benzopyran-2-one (compound (45)), 3-hexyloxy-4-hydroxy-5-(2,3-dihydroxypropyloxy)-2H-1-benzopyran-2-one (compound (46)), 3-octyloxy-4-hydroxy-5-(2,3-dihydroxypropyloxy)-2H-1-benzopyran-2-one (compound (47)), 3-decyloxy-4-hydroxy-5-(2,3-dihydroxypropyloxy)-2H-1-benzopyran-2-one (compound (48)), 3-(1-hexenyloxy)-4-hydroxy-5-(2,3-dihydroxypropyloxy)-2H-1-benzopyran-2-one (compound (49)), 3-(3-methyl-2-butenyloxy)-4-hydroxy-5-(2,3-dihydroxypropyloxy)-2H-1-benzopyran-2-one (compound (50)), 3-methoxy-4-hydroxy-5-(3,4-dihydroxybutoxy)-2H-1-benzopyran-2-one (compound (51)), 3-ethoxy-4-hydroxy-5-(3,4-dihydroxybutoxy)-2H-1-benzopyran-2-one (compound (52)), 3-hexyloxy-4-hydroxy-5-(3,4-dihydroxybutoxy)-2H-1-benzopyran-2-one (compound (53)), 3-octyloxy-4-hydroxy-5-(3,4-dihydroxybutoxy)-2H-1-benzopyran-2-one (compound (54)), 3-(1-propenyloxy)-4-hydroxy-5-(3,4-dihydroxybutoxy)-2H-1-benzopyran-2-one (compound (55)), 3-(1-octenyloxy)-4-hydroxy-5-(3,4-dihydroxybutoxy)-2H-1-benzopyran-2-one (compound (56)), 3-geranyloxy-4-hydroxy-5-(3,4-dihydroxybutoxy)-

2H-1-benzopyran-2-one (compound (57)), 3-methoxy-4-hydroxy-5-hydroxycarbonylmethoxy-2H-1-benzopyran-2-one (compound (58)), 3-ethoxy-4-hydroxy-5-hydroxycarbonylmethoxy-2H-1-benzopyran-2-one (compound (59)), 3-propyloxy-4-hydroxy-5-hydroxycarbonylmethoxy-2H-1-benzopyran-2-one (compound (60)), 3-isopropyloxy-4-hydroxy-5-hydroxycarbonylmethoxy-2H-1-benzopyran-2-one (compound (61)), 3-butoxy-4-hydroxy-5-hydroxycarbonylmethoxy-2H-1-benzopyran-2-one (compound (62)), 3-(s-butoxy)-4-hydroxy-5-hydroxycarbonylmethoxybenzopyran-2-one (compound (63)), 3-pentyloxy-4-hydroxy-5-hydroxycarbonylmethoxy-2H-1-benzopyran-2-one (compound (64)), 3-hexyloxy-4-hydroxy-5-hydroxycarbonylmethoxy-2H-1-benzopyran-2-one (compound (65)), 3-(2-methylpentyloxy)-4-hydroxy-5-hydroxycarbonylmethoxy-2H-1-benzopyran-2-one (compound (66)), 3-heptyloxy-4-hydroxy-5-hydroxycarbonylmethoxy-2H-1-benzopyran-2-one (compound (67)), 3-(1-ethylpentyloxy)-4-hydroxy-5-hydroxycarbonylmethoxy-2H-1-benzopyran-2-one (compound (68)), 3-(4-methylpentyloxy)-4-hydroxy-5-hydroxycarbonylmethoxy-2H-1-benzopyran-2-one (compound (69)), 3-(1-ethylbutoxy)-4-hydroxy-5-hydroxycarbonylmethoxy-2H-1-benzopyran-2-one (compound (70)), 3-octyloxy-4-hydroxy-5-hydroxycarbonylmethoxy-2H-1-benzopyran-2-one (compound (71)), 3-(1-ethylhexyloxy)-4-hydroxy-5-hydroxycarbonylmethoxy-2H-1-benzopyran-2-one (compound (72)), 3-decyloxy-4-hydroxy-5-hydroxycarbonylmethoxy-2H-1-benzopyran-2-one (compound (73)), 3-vinyloxy-4-hydroxy-5-hydroxycarbonylmethoxy-2H-1-benzopyran-2-one (compound (74)), 3-(1-propenyloxy)-4-hydroxy-5-hydroxycarbonylmethoxy-2H-1-benzopyran-2-one (compound (75)), 3-(1-butenyloxy)-4-hydroxy-5-hydroxycarbonylmethoxy-2H-1-benzopyran-2-one (compound (76)), 3-(1-hexenyloxy)-4-hydroxy-5-hydroxycarbonylmethoxy-2H-1-benzopyran-2-one (compound (77)), 3-(1-octenyloxy)-4-hydroxy-5-hydroxycarbonylmethoxy-2H-1-benzopyran-2-one (compound (78)), 3-(1-decenyloxy)-4-hydroxy-5-hydroxycarbonylmethoxy-2H-1-benzopyran-2-one (compound (79)), 3-(3-methyl-2-butenyloxy)-4-hydroxy-5-hydroxycarbonylmethoxy-2H-1-benzopyran-2-one (compound (80)), 3-geranyloxy-4-hydroxy-5-hydroxycarbonylmethoxy-2H-1-benzopyran-2-one (compound (81)), 3-prenyloxy-4-hydroxy-5-hydroxycarbonylmethoxy-2H-1-benzopyran-2-one (compound (82)), 3-methoxy-4-hydroxy-5-(2-hydroxycarbonylethoxy)-2H-1-benzopyran-2-one (compound (83)), 3-ethoxy-4-hydroxy-5-(2-hydroxycarbonylethoxy)-2H-1-benzopyran-2-one (compound (84)), 3-butoxy-4-hydroxy-5-(2-hydroxycarbonylethoxy)-2H-1-benzopyran-2-one (compound (85)), 3-hexyloxy-4-hydroxy-5-(2-hydroxycarbonylethoxy)-2H-1-benzopyran-2-one (compound (86)), 3-octyloxy-4-hydroxy-5-(2-hydroxycarbonylethoxy)-2H-1-benzopyran-2-one (compound (87)), 3-(1-propenyloxy)-4-hydroxy-5-(2-hydroxycarbonylethoxy)-2H-1-benzopyran-2-one (compound (88)), 3-(1-octenyloxy)-4-hydroxy-5-(2-hydroxycarbonylethoxy)-2H-1-benzopyran-2-one (compound (89)), 3-geranyloxy-4-hydroxy-5-(2-hydroxycarbonylethoxy)-2H-1-benzopyran-2-one (compound (90)), 3-ethoxy-4-hydroxy-5-(3-hydroxycarbonylpropyloxy)-2H-1-benzopyran-2-one (compound (91)), 3-butoxy-4-hydroxy-5-(3-hydroxycarbonylpropyloxy)-2H-1-benzopyran-2-one (compound (92)), 3-hexyloxy-4-hydroxy-5-(3-hydroxycarbonylpropyloxy)-2H-1-benzopyran-2-one (compound (93)), 3-octyloxy-4-hydroxy-5-(3-hydroxycarbonylpropyloxy)-2H-1-benzopyran-2-one (compound (94)), 3-(1-butenyloxy)-4-hydroxy-5-(3-hydroxycarbonylpropyloxy)-2H-1-benzopyran-2-one (compound (95)), 3-prenyloxy-4-hydroxy-5-(3-hydroxycarbonylpropyloxy)-2H-1-benzopyran-2-one (compound (96)), 3-ethoxy-4-hydroxy-5-(4-hydroxycarbonylbutoxy)-2H-1-benzopyran-2-one (compound (97)), 3-butoxy-4-hydroxy-5-(4-hydroxycarbonylbutoxy)-2H-1-benzopyran-2-one (compound (98)), 3-hexyloxy-4-hydroxy-5-(4-hydroxycarbonylbutoxy)-2H-1-benzopyran-2-one (compound (99)), 3-octyloxy-4-hydroxy-5-(4-hydroxycarbonylbutoxy)-2H-1-benzopyran-2-one (compound (100)), 3-(1-octenyloxy)-4-hydroxy-5-(4-hydroxycarbonylbutoxy)-2H-1-benzopyran-2-one (compound (101)), 3-methoxy-4-hydroxy-6-(2-hydroxyethoxy)-2H-1-benzopyran-2-one (compound (102)), 3-ethoxy-4-hydroxy-6-(2-hydroxyethoxy)-2H-1-benzopyran-2-one (compound (103)), 3-propyloxy-4-hydroxy-6-(2-hydroxyethoxy)-2H-1-benzopyran-2-one (compound (104)), 3-isopropyloxy-4-hydroxy-6-(2-hydroxyethoxy)-2H-1-benzopyran-2-one (compound (105)), 3-butoxy-4-hydroxy-6-(2-hydroxyethoxy)-2H-1-benzopyran-2-one (compound (106)), 3-(s-butoxy)-4-hydroxy-5-(2-hydroxyethoxy)-2H-1-benzopyran-2-one (compound (107)), 3-pentyloxy-4-hydroxy-6-(2-hydroxyethoxy)-2H-1-benzopyran-2-one (compound (108)), 3-hexyloxy-4-hydroxy-6-(2-hydroxyethoxy)-2H-1-benzopyran-2-one (compound (109)), 3-(2-methylpentyloxy)-4-hydroxy-6-(2-hydroxyethoxy)-2H-1-benzopyran-2-one (compound (110)), 3-heptyloxy-4-hydroxy-6-(2-hydroxyethoxy)-2H-1-benzopyran-2-one (compound (111)), 3-(1-ethylpentyloxy)-4-hydroxy-6-(2-hydroxyethoxy)-2H-1-benzopyran-2-one (compound (112)), 3-(4-methylpentyloxy)-4-hydroxy-6-(2-hydroxyethoxy)-2H-1-benzopyran-2-one (compound (113)), 3-(1-ethylbutoxy)-4-hydroxy-6-(2-hydroxyethoxy)-2H-1-benzopyran-2-one (compound (114)), 3-octyloxy-4-hydroxy-6-(2-hydroxyethoxy)-2H-1-benzopyran-2-one (compound (115)), 3-(1-ethylhexyloxy)-4-hydroxy-6-(2-hydroxyethoxy)-2H-1-benzopyran-2-one (compound (116)), 3-decyloxy-4-hydroxy-6-(2-hydroxyethoxy)-2H-1-benzopyran-2-one (compound (117)), 3-vinyloxy-4-hydroxy-6-(2-hydroxyethoxy)-2H-1-benzopyran-2-one (compound (118)), 3-(1-propenyloxy)-4-hydroxy-6-(2-hydroxyethoxy)-2H-1-benzopyran-2-one (compound (119)), 3-(1-butenyloxy)-4-hydroxy-6-(2-hydroxyethoxy)-2H-1-benzopyran-2-one (compound (120)), 3-(1-hexenyloxy)-4-hydroxy-6-(2-hydroxyethoxy)-2H-1-benzopyran-2-one (compound (121)), 3-(1-octenyloxy)-4-hydroxy-6-(2-hydroxyethoxy)-2H-1-benzopyran-2-one (compound (122)), 3-(1-decenyloxy)-4-hydroxy-6-(2-hydroxyethoxy)-2H-1-benzopyran-2-one (compound (123)), 3-(3-methyl-2-butenyloxy)-4-hydroxy-6-(2-hydroxyethoxy)-2H-1-benzopyran-2-one (compound (124)), 3-geranyloxy-4-hydroxy-6-(2-hydroxyethoxy)-2H-1-benzopyran-2-one (compound (125)), 3-prenyloxy-4-hydroxy-6-(2-hydroxyethoxy)-2H-1-benzopyran-2-one (compound (126)), 3-methoxy-4-hydroxy-6-(3-hydroxypropyloxy)-2H-1-benzopyran-2-one (compound (127)), 3-ethoxy-4-hydroxy-6-(3-hydroxypropyloxy)-2H-1-benzopyran-2-one (compound (128)), 3-(butoxy)-4- hydroxy-6-(3-hydroxypropyloxy)-2H-1-benzopyran-2-one (compound (129)), 3-hexyloxy-4-hydroxy-6-(3-hydroxypropyloxy)-2H-1-benzopyran-2-one (compound (130)), 3-(2-methylpentyloxy)-4-hydroxy-6-(3-hydroxypropyloxy)-2H-1-benzopyran-2-one (compound (131)), 3-octyloxy-4-hydroxy-6-(3-hydroxypropyloxy)-2H-1-benzopyran-2-one (compound (132)), 3-decyloxy-4-hydroxy-6-(3-hydroxypropyloxy)-2H-1-benzopyran-2-one (compound (133)), 3-(1-propenyloxy)-4-hydroxy-6-(3-hydroxypropyloxy)-2H-1-benzopyran-2-one (compound (134)), 3-(1-octenyloxy)-4-hydroxy-6-(3-hydroxypropyloxy)-2H-1-benzopyran-2-one (compound (135)), 3-geranyloxy-4-hydroxy-6-(3-hydroxypropyloxy)-2H-1-benzopyran-2-one (compound (136)), 3-ethoxy-4-hydroxy-6-(4-hydroxybutoxy)-2H-1-benzopyran-2-one (compound (137)), 3-butoxy-4-hydroxy-6-(4-hydroxybutoxy)-2H-1-benzopyran-2-one (compound (138)), 3-(s-butoxy)-4-hydroxy-6-(4-hydroxybutoxy)-2H-1-benzopyran-2-one (compound (139)), 3-hexyloxy-4-hydroxy-6-(4-hydroxybutoxy)-2H-1-benzopyran-2-one (compound (140)), 3-(1-ethylpentyloxy)-4-hydroxy-6-(4-hydroxybutoxy)-2H-1-benzopyran-2-one (compound (141)), 3-octyloxy-4-hydroxy-6-(4-hydroxybutoxy)-2H-1-benzopyran-2-one (compound (142)), 3-(1-butenyloxy)-4-hydroxy-6-(4-hydroxybutoxy)-2H-1-benzopyran-2-one (compound (143)), 3-prenyloxy-4-hydroxy-6-(4-hydroxybutoxy)-2H-1-benzopyran-2-one (compound (144)), 3-ethoxy-4-hydroxy-6-(2,3-dihydroxypropyloxy)-2H-1-benzopyran-2-one (compound (145)), 3-butoxy-4-hydroxy-6-(2,3-dihydroxypropyloxy)-2H-1-benzopyran-2-one (compound (146)), 3-hexyloxy-4-hydroxy-6-(2,3-dihydroxypropyloxy)-2H-1-benzopyran-2-one (compound (147)), 3-octyloxy-4-hydroxy-6-(2,3-dihydroxypropyloxy)-2H-1-benzopyran-2-one (compound (148)), 3-decyloxy-4-hydroxy-6-(2,3-dihydroxypropyloxy)-2H-1-benzopyran-2-one (compound (149)), 3-(1-hexenyloxy)-4-hydroxy-6-(2,3-dihydroxypropyloxy)-2H-1-benzopyran-2-one (compound (150)), 3-(3-methyl-2-butenyloxy)-4-hydroxy-6-(2,3-dihydroxypropyloxy)-2H-1-benzopyran-2-one (compound (151)), 3-methoxy-4-hydroxy-6-(3,4-dihydroxybutoxy)-2H-1-benzopyran-2-one (compound (152)), 3-ethoxy-4-hydroxy-6-(3,4-dihydroxybutoxy)-2H-1-benzopyran-2-one (compound (153)), 3-hexyloxy-4-hydroxy-6-(3,4-dihydroxybutoxy)-2H-1-benzopyran-2-one (compound (154)), 3-octyloxy-4-hydroxy-6-(3,4-dihydroxybutoxy)-2H-1-benzopyran-2-one (compound (155)), 3-(1-propenyloxy)-4-hydroxy-6-(3,4-dihydroxybutoxy)-2H-1-benzopyran-2-one (compound (156)), 3-(1-octenyloxy)-4-hydroxy-6-(3,4-dihydroxybutoxy)-2H-1-benzopyran-2-one (compound (157)), 3-geranyloxy-4-hydroxy-6-(3,4-dihydroxybutoxy)-2H-1-benzopyran-2-one (compound (158)), 3-methoxy-4-hydroxy-6-hydroxycarbonylmethoxy-2H-1-benzopyran-2-one (compound (159)), 3-ethoxy-4-hydroxy-6-hydroxycarbonylmethoxy-2H-1-benzopyran-2-one (compound (160)), 3-propyloxy-4-hydroxy-6-hydroxycarbonylmethoxy-2H-1-benzopyran-2-one (compound (161)), 3-isopropyloxy-4-hydroxy-6-hydroxycarbonylmethoxy-2H-1-benzopyran-2-one (compound (162)), 3-butoxy-4-hydroxy-6-hydroxycarbonylmethoxy-2H-1-benzopyran-2-one (compound (163)), 3-(s-butoxy)-4-hydroxy-6-hydroxycarbonylmethoxybenzopyran-2-one (compound (164)), 3-pentyloxy-4-hydroxy-6-hydroxycarbonylmethoxy-2H-1-benzopyran-2-one (compound (165)), 3-hexyloxy-4-hydroxy-6-hydroxycarbonylmethoxy-2H-1-benzopyran-2-one (compound (166)), 3-(2-methylpentyloxy)-4-hydroxy-6-hydroxycarbonylmethoxy-2H-1-benzopyran-2-one (compound (167)), 3-heptyloxy-4-hydroxy-6-hydroxycarbonylmethoxy-2H-1-benzopyran-2-one (compound (168)), 3-(1-ethylpentyloxy)-4-hydroxy-6-hydroxycarbonylmethoxy-2H-1-benzopyran-2-one (compound (169)), 3-(4-ethylpentyloxy)-4-hydroxy-6-hydroxycarbonylmethoxy-2H-1-benzopyran-2-one (compound (170)), 3-(1-ethylbutoxy)-4-hydroxy-6-hydroxycarbonylmethoxy-2H-1-benzopyran-2-one (compound (171)), 3-octyloxy-4-hydroxy-6-hydroxycarbonylmethoxy-2H-1-benzopyran-2-one (compound (172)), 3-(1-ethylhexyloxy)-4-hydroxy-6-hydroxycarbonylmethoxy-2H-1-benzopyran-2-one (compound (173)), 3-decyloxy-4-hydroxy-6-hydroxycarbonylmethoxy-2H-1-benzopyran-2-one (compound (174)), 3-vinyloxy-4-hydroxy-6-hydroxycarbonylmethoxy-2H-1-benzopyran-2-one (compound (175)), 3-(1-propenyloxy)-4-hydroxy-6-hydroxycarbonylmethoxy-2H-1-benzopyran-2-one (compound (176)), 3-(1-butenyloxy)-4-hydroxy-6-hydroxycarbonylmethoxy-2H-1-benzopyran-2-one (compound (177)), 3-(1-hexenyloxy)-4-hydroxy-6-hydroxycarbonylmethoxy-2H-1-benzopyran-2-one (compound (178)), 3-(1-octenyloxy)-4-hydroxy-6-hydroxycarbonylmethoxy-2H-1-benzopyran-2-one (compound (179)), 3-(1-decenyloxy)-4-hydroxy-6-hydroxycarbonylmethoxy-2H-1-benzopyran-2-one (compound (180)), 3-(3-methyl-2-butenyloxy)-4-hydroxy-6-hydroxycarbonylmethoxy-2H-1-benzopyran-2-one (compound (181)), 3-geranyloxy-4-hydroxy-6-hydroxycarbonylmethoxy-2H-1-benzopyran-2-one (compound (182)), 3-prenyloxy-4-hydroxy-6-hydroxycarbonylmethoxy-2H-1-benzopyran-2-one (compound (183)), 3-methoxy-4-hydroxy-6-(2-hydroxycarbonylethoxy)-2H-1-benzopyran-2-one (compound (184)), 3-ethoxy-4-hydroxy-6-(2-hydroxycarbonylethoxy)-2H-1-benzopyran-2-one (compound (185)), 3-butoxy-4-hydroxy-6-(2-hydroxycarbonylethoxy)-2H-1-benzopyran-2-one (compound (186)), 3-hexyloxy-4-hydroxy-6-(2-hydroxycarbonylethoxy)-2H-1-benzopyran-2-one (compound (187)), 3-octyloxy-4-hydroxy-6-(2-hydroxycarbonylethoxy)-2H-1-benzopyran-2-one (compound (188)), 3-(1-propenyloxy)-4-hydroxy-6-(2-hydroxycarbonylethoxy)-2H-1-benzopyran-2-one (compound (189)), 3-(1-octenyloxy)-4-hydroxy-6-(2-hydroxycarbonylethoxy)-2H-1-benzopyran-2-one (compound (190)), 3-geranyloxy-4-hydroxy-6-(2-hydroxycarbonylethoxy)-2H-1-benzopyran-2-one (compound (191)), 3-ethoxy-4-hydroxy-6-(3-hydroxycarbonylpropyloxy)-2H-1-benzopyran-2-one (compound (192)), 3-butoxy-4-hydroxy-6-(3-hydroxycarbonylpropyloxy)-2H-1-benzopyran-2-one (compound (193)), 3-hexyloxy-4-hydroxy-6-(3-hydroxycarbonylpropyloxy)-2H-1-benzopyran-2-one (compound (194)), 3-octyloxy-4-hydroxy-6-(3-hydroxycarbonylpropyloxy)-2H-1-benzopyran-2-one (compound (195)), 3-(1-butenyloxy)-4-hydroxy-6-(3-hydroxycarbonylpropyloxy)-2H-1-benzopyran-2-one (compound (196)), 3-prenyloxy-4-hydroxy-6-(3-hydroxycarbonylpropyloxy)-2H-1-benzopyran-2-one (compound (197)), 3-ethoxy-4-hydroxy-6-(4-hydroxycarbonylbutoxy)-2H-1-benzopyran-2-one (compound (198)), 3-butoxy-4-hydroxy-6-(4-hydroxycarbonylbutoxy)-2H-1-benzopyran-2-one (compound (199)), 3-hexyloxy-4-hydroxy-6-(4-hydroxycarbonylbutoxy)-2H-1-benzopyran-2-one (compound (200)), 3-octyloxy-4-hydroxy-6-(4-hydroxycarbonylbutoxy)-2H-1-benzopyran-2-one (compound (201)), 3-(1-octenyloxy)-4-hydroxy-6-(4-hydroxycarbonylbutoxy)-2H-1-benzopyran-2-one (compound (202)), 3-methoxy-4-hydroxy-7-(2-hydroxyethoxy)-2H-1-benzopyran-2-one (compound (203)), 3-ethoxy-4-hydroxy-7-(2-hydroxyethoxy)-2H-1-benzopyran-2-one (compound (204)), 3-propyloxy-4-hydroxy-7-(2-hydroxyethoxy)-2H-1-benzopyran-2-one (compound (205)), 3-isopropyloxy-4-hydroxy-7-(2-hydroxyethoxy)-2H-1-benzopyran-2-one (compound (206)), 3-butoxy-4-hydroxy-7-(2-hydroxyethoxy)-2H-1-benzopyran-2-one (compound (207)), 3-(s-butoxy)-4-hydroxy-7-(2-hydroxyethoxy)-2H-1-benzopyran-2-one (compound (208)), 3-pentyloxy-4-hydroxy-7-(2-hydroxyethoxy)-2H-1-benzopyran-2-one (compound (209)), 3-hexyloxy-4-hydroxy-7-(2-hydroxyethoxy)-2H-1-benzopyran-2-one (compound (210)), 3-(2-methylpentyloxy)-4-hydroxy-7-(2-hydroxyethoxy)-2H-1-benzopyran-2-one (compound (211)), 3-heptyloxy-4-hydroxy-7-(2-hydroxyethoxy)-2H-1-benzopyran-2-one (compound (212)), 3-(1-ethylpentyloxy)-4-hydroxy-7-(2-hydroxyethoxy)-2H-1-benzopyran-2-one (compound (213)), 3-(4-ethylpentyloxy)-4-hydroxy-7-(2-hydroxyethoxy)-2H-1-benzopyran-2-one (compound (214)), 3-(1-ethylbutoxy)-4-hydroxy-7-(2-hydroxyethoxy)-2H-1-benzopyran-2-one (compound (215)), 3-octyloxy-4-hydroxy-7-(2-hydroxyethoxy)-2H-1-benzopyran-2-one (compound (216)), 3-(1-ethylhexyloxy)-4-hydroxy-7-(2-hydroxyethoxy)-2H-1-benzopyran-2-one (compound (217)), 3-decyloxy-4-hydroxy-7-(2-hydroxyethoxy)-2H-1-benzopyran-2-one (compound (218)), 3-vinyloxy-4-hydroxy-7-(2-hydroxyethoxy)-2H-1-benzopyran-2-one (compound (219)), 3-(1-propenyloxy)-4-hydroxy-7-(2-hydroxyethoxy)-2H-1-benzopyran-2-one (compound (220)), 3-(1-butenyloxy)-4-hydroxy-7-(2-hydroxyethoxy)-2H-1-benzopyran-2-one (compound (221)), 3-(1-hexenyloxy)-4-hydroxy-7-(2-hydroxyethoxy)-2H-1-benzopyran-2-one (compound (222)), 3-(1-octenyloxy)-4-hydroxy-7-(2-hydroxyethoxy)-2H-1-benzopyran-2-one (compound (223)), 3-(1-decenyloxy)-4-hydroxy-7-(2-hydroxyethoxy)-2H-1-benzopyran-2-one (compound (224)), 3-(3-methyl-2-butenyloxy)-4-hydroxy-7-(2-hydroxyethoxy)-2H-1-benzopyran-2-one (compound (225)), 3-geranyloxy-4-hydroxy-7-(2-hydroxyethoxy)-2H-1-benzopyran-2-one (compound (226)), 3-prenyloxy-4-hydroxy-7-(2-hydroxyethoxy)-2H-1-benzopyran-2-one (compound (227)), 3-methoxy-4-hydroxy-7-(3-hydroxypropyloxy)-2H-1-benzopyran-2-one (compound (228)), 3-ethoxy-4-hydroxy-7-(3-hydroxypropyloxy)-2H-1-benzopyran-2-one (compound (229)), 3-(s-butoxy)-4-hydroxy-7-(3-hydroxypropyloxy)-2H-1-benzopyran-2-one (compound (230)), 3-hexyloxy-4-hydroxy-7-(3-hydroxypropyloxy)-2H-1-benzopyran-2-one (compound (231)), 3-(2-methylpentyloxy)-4-hydroxy-7-(3-hydroxypropyloxy)-2H-1-benzopyran-2-one (compound (232)), 3-octyloxy-4-hydroxy-7-(3-hydroxypropyloxy)-2H-1-benzopyran-2-one (compound (233)), 3-decyloxy-4-hydroxy-7-(3-hydroxypropyloxy)-2H-1-benzopyran-2-one (compound (234)), 3-(1-propenyloxy)-4-hydroxy-7-(3-hydroxypropyloxy)-2H-1-benzopyran-2-one (compound (235)), 3-(1-octenyloxy)-4-hydroxy-7-(3-hydroxypropyloxy)-2H-1-benzopyran-2-one (compound (236)), 3-geranyloxy-4-hydroxy-7-(3-hydroxypropyloxy)-2H-1-benzopyran-2-one (compound (237)), 3-ethoxy-4-hydroxy-7-(4-hydroxybutoxy)-2H-1-benzopyran-2-one (compound (238)), 3-butoxy-4-hydroxy-7-(4-hydroxybutoxy)-2H-1-benzopyran-2-one (compound (239)), 3-(s-butoxy)-4-hydroxy-7-(4-hydroxybutoxy)-2H-1-benzopyran-2-one (compound (240)), 3-hexyloxy-4-hydroxy-7-(4-hydroxybutoxy)-2H-1-benzopyran-2-one (compound (241)), 3-(1-ethylpentyloxy)-4-hydroxy-7-(4-hydroxybutoxy)-2H-1-benzopyran-2-one (compound (242)), 3-octyloxy-4-hydroxy-7-(4-hydroxybutoxy)-2H-1-benzopyran-2-one (compound (243)), 3-(1-butenyloxy)-4-hydroxy-7-(4-hydroxybutoxy)-2H-1-benzopyran-2-one (compound (244)), 3-prenyloxy-4-hydroxy-7-(4-hydroxybutoxy)-2H-1-benzopyran-2-one (compound (245)), 3-ethoxy-4-hydroxy-7-(2,3-dihydroxypropyloxy)-2H-1-benzopyran-2-one (compound (246)), 3-butoxy-4-hydroxy-7-(2,3-dihydroxypropyloxy)-2H-1-benzopyran-2-one (compound (247)), 3-hexyloxy-4-hydroxy-7-(2,3-dihydroxypropyloxy)-2H-1-benzopyran-2-one (compound (248)), 3-octyloxy-4-hydroxy-7-(2,3-dihydroxypropyloxy)-2H-1-benzopyran-2-one (compound (249)), 3-decyloxy-4-hydroxy-7-(2,3-dihydroxypropyloxy)-2H-1-benzopyran-2-one (compound (250)), 3-(1-hexenyloxy)-4-hydroxy-7-(2,3-dihydroxypropyloxy)-2H-1-benzopyran-2-one (compound (251)), 3-(3-methyl-2-butenyloxy)-4-hydroxy-7-(2,3-dihydroxypropyloxy)-2H-1-benzopyran-2-one (compound (252)), 3-methoxy-4-hydroxy-7-(3,4-dihydroxybutoxy)-2H-1-benzopyran-2-one (compound (253)), 3-ethoxy-4-hydroxy-7-(3,4-dihydroxybutoxy)-2H-1-benzopyran-2-one (compound (254)), 3-hexyloxy-4-hydroxy-7-(3,4-dihydroxybutoxy)-2H-1-benzopyran-2-one (compound (255)), 3-octyloxy-4-hydroxy-7-(3,4-dihydroxybutoxy)-2H-1-benzopyran-2-one (compound (256)), 3-(1-propenyloxy)-4-hydroxy-7-(3,4-dihydroxybutoxy)-2H-1-benzopyran-2-one (compound (257)), 3-(1-octenyloxy)-4-hydroxy-7-(3,4-dihydroxybutoxy)-2H-1-benzopyran-2-one (compound (258)), 3-geranyloxy-4-hydroxy-7-(3,4-dihydroxybutoxy)-2H-1-benzopyran-2-one (compound (259)), 3-methoxy-4-hydroxy-7-hydroxycarbonylmethoxy-2H-1-benzopyran-2-one (compound (260)), 3-ethoxy-4-hydroxy-7-hydroxycarbonylmethoxy-2H-1-benzopyran-2-one (compound (261)), 3-propyloxy-4-hydroxy-7-hydroxycarbonylmethoxy-2H-1-benzopyran-2-one (compound (262)), 3-isopropyloxy-4-hydroxy-7-hydroxycarbonylmethoxy-2H-1-benzopyran-2-one (compound (263)), 3-butoxy-4-hydroxy-7-hydroxycarbonylmethoxy-2H-1-benzopyran-2-one (compound (264)), 3-(s-butoxy)-4-hydroxy-7-hydroxycarbonylmethoxybenzopyran-2-one (compound (265)), 3-pentyloxy-4-hydroxy-7-hydroxycarbonylmethoxy-2H-1-benzopyran-2-one (compound (266)), 3-hexyloxy-4-hydroxy-7-hydroxycarbonylmethoxy-2H-1-benzopyran-2-one (compound (267)), 3-(2-methylpentyloxy)-4-hydroxy-7-hydroxycarbonylmethoxy-2H-1-benzopyran-2-one (compound (268)), 3-heptyloxy-4-hydroxy-7-hydroxycarbonylmethoxy-2H-1-benzopyran-2-one (compound (269)), 3-(1-ethylpentyloxy)-4-hydroxy-7-hydroxycarbonylmethoxy-2H-1-benzopyran-2-one (compound (270)), 3-(4-ethylpentyloxy)-4-hydroxy-7-hydroxycarbonylmethoxy-2H-1-benzopyran-2-one (compound (271)), 3-(1-ethylbutoxy)-4-hydroxy-7-hydroxycarbonylmethoxy-2H-1-benzopyran-2-one (compound (272)), 3-octyloxy-4-hydroxy-7-hydroxycarbonylmethoxy-2H-1-benzopyran-2-one (compound (273)), 3-(1-ethylhexyloxy)-4-hydroxy-7-hydroxycarbonylmethoxy-2H-1-benzopyran-2-one (compound (274)), 3-decyloxy-4-hydroxy-7-hydroxycarbonylmethoxy-2H-1-benzopyran-2-one (compound (275)), 3-vinyloxy-4-hydroxy-7- hydroxycarbonylmethoxy-2H-1-benzopyran-2-one (compound (276)), 3-(1-propenyloxy)-4-hydroxy-7-hydroxycarbonylmethoxy-2H-1-benzopyran-2-one (compound (277)), 3-(1-butenyloxy)-4-hydroxy-7-hydroxycarbonylmethoxy-2H-1-benzopyran-2-one (compound (278)), 3-(1-hexenyloxy)-4-hydroxy-7-hydroxycarbonylmethoxy-2H-1-benzopyran-2-one (compound (279)), 3-(1-octenyloxy)-4-hydroxy-7-hydroxycarbonylmethoxy-2H-1-benzopyran-2-one (compound (280)), 3-(1-decenyloxy)-4-hydroxy-7-hydroxycarbonylmethoxy-2H-1-benzopyran-2-one (compound (281)), 3-(3-methyl-2-butenyloxy)-4-hydroxy-7-hydroxycarbonylmethoxy-2H-1-benzopyran-2-one (compound (282)), 3-geranyloxy-4-hydroxy-7-hydroxycarbonylmethoxy-2H-1-benzopyran-2-one (compound (283)), 3-prenyloxy-4-hydroxy-7-hydroxycarbonylmethoxy-2H-1-benzopyran-2-one (compound (284)), 3-methoxy-4-hydroxy-7-(2-hydroxycarbonylethoxy)-2H-1-benzopyran-2-one (compound (285)), 3-ethoxy-4-hydroxy-7-(2-hydroxycarbonylethoxy)-2H-1-benzopyran-2-one (compound (286)), 3-butoxy-4-hydroxy-7-(2-hydroxycarbonylethoxy)-2H-1-benzopyran-2-one (compound (287)), 3-hexyloxy-4-hydroxy-7-(2-hydroxycarbonylethoxy)-2H-1-benzopyran-2-one (compound (288)), 3-octyloxy-4-hydroxy-7-(2-hydroxycarbonylethoxy)-2H-1-benzopyran-2-one (compound (289)), 3-(1-propenyloxy)-4-hydroxy-7-(2-hydroxycarbonylethoxy)-2H-1-benzopyran-2-one (compound (290)), 3-(1-octenyloxy)-4-hydroxy-7-(2-hydroxycarbonylethoxy)-2H-1-benzopyran-2-one (compound (291)), 3-geranyloxy-4-hydroxy-7-(2-hydroxycarbonylethoxy)-2H-1-benzopyran-2-one (compound (292)), 3-ethoxy-4-hydroxy-7-(3-hydroxycarbonylpropyloxy)-2H-1-benzopyran-2-one (compound (293)), 3-butoxy-4-hydroxy-7-(3-hydroxycarbonylpropyloxy)-2H-1-benzopyran-2-one (compound (294)), 3-hexyloxy-4-hydroxy-7-(3-hydroxycarbonylpropyloxy)-2H-1-benzopyran-2-one (compound (295)), 3-octyloxy-4-hydroxy-7-(3-hydroxycarbonylpropyloxy)-2H-1-benzopyran-2-one (compound (296)), 3-(1-butenyloxy)-4-hydroxy-7-(3-hydroxycarbonylpropyloxy)-2H-1-benzopyran-2-one (compound (297)), 3-prenyloxy-4-hydroxy-7-(3-hydroxycarbonylpropyloxy)-2H-1-benzopyran-2-one (compound (298)), 3-ethoxy-4-hydroxy-7-(4-hydroxycarbonylbutoxy)-2H-1-benzopyran-2-one (compound (299)), 3-butoxy-4-hydroxy-7-(4-hydroxycarbonylbutoxy)-2H-1-benzopyran-2-one (compound (300)), 3-hexyloxy-4-hydroxy-7-(4-hydroxycarbonylbutoxy)-2H-1-benzopyran-2-one (compound (301)), 3-octyloxy-4-hydroxy-7-(4-hydroxycarbonylbutoxy)-2H-1-benzopyran-2-one (compound (302)), 3-(1-octenyloxy)-4-hydroxy-7-(4-hydroxycarbonylbutoxy)-2H-1-benzopyran-2-one (compound (303)), 3-methoxy-4-hydroxy-8-(2-hydroxyethoxy)-2H-1-benzopyran-2-one (compound (304)), 3-ethoxy-4-hydroxy-8-(2-hydroxyethoxy)-2H-1-benzopyran-2-one (compound (305)), 3-propyloxy-4-hydroxy-8-(2-hydroxyethoxy)-2H-1-benzopyran-2-one (compound (306)), 3-isopropyloxy-4-hydroxy-8-(2-hydroxyethoxy)-2H-1-benzopyran-2-one (compound (307)), 3-butoxy-4-hydroxy-8-(2-hydroxyethoxy)-2H-1-benzopyran-2-one (compound (308)), 3-(s-butoxy)-4-hydroxy-8-(2-hydroxyethoxy)-2H-1-benzopyran-2-one (compound (309)), 3-pentyloxy-4-hydroxy-8-(2-hydroxyethoxy)-2H-1-benzopyran-2-one (compound (310)), 3-hexyloxy-4-hydroxy-8-(2-hydroxyethoxy)-2H-1-benzopyran-2-one (compound (311)), 3-(2-methylpentyloxy)-4-hydroxy-8-(2-hydroxyethoxy)-2H-1-benzopyran-2-one (compound (312)), 3-heptyloxy-4-hydroxy-8-(2-hydroxyethoxy)-2H-1-benzopyran-2-one (compound (313)), 3-(1-ethylpentyloxy)-4-hydroxy-8-(2-hydroxyethoxy)-2H-1-benzopyran-2-one (compound (314)), 3-(4-ethylpentyloxy)-4-hydroxy-8-(2-hydroxyethoxy)-2H-1-benzopyran-2-one (compound (315)), 3-(1-ethylbutoxy)-4-hydroxy-8-(2-hydroxyethoxy)-2H-1-benzopyran-2-one (compound (316)), 3-octyloxy-4-hydroxy-8-(2-hydroxyethoxy)-2H-1-benzopyran-2-one (compound (317)), 3-(1-ethylhexyloxy)-4-hydroxy-8-(2-hydroxyethoxy)-2H-1-benzopyran-2-one (compound (318)), 3-decyloxy-4-hydroxy-8-(2-hydroxyethoxy)-2H-1-benzopyran-2-one (compound (319)), 3-vinyloxy-4-hydroxy-8-(2-hydroxyethoxy)-2H-1-benzopyran-2-one (compound (320)), 3-(1-propenyloxy)-4-hydroxy-8-(2-hydroxyethoxy)-2H-1-benzopyran-2-one (compound (321)), 3-(1-butenyloxy)-4-hydroxy-8-(2-hydroxyethoxy)-2H-1-benzopyran-2-one (compound (322)), 3-(1-hexenyloxy)-4-hydroxy-8-(2-hydroxyethoxy)-2H-1-benzopyran-2-one (compound (323)), 3-(1-octenyloxy)-4-hydroxy-8-(2-hydroxyethoxy)-2H-1-benzopyran-2-one (compound (324)), 3-(1-decenyloxy)-4-hydroxy-8-(2-hydroxyethoxy)-2H-1-benzopyran-2-one (compound (325)), 3-(3-methyl-2-butenyloxy)-4-hydroxy-8-(2-hydroxyethoxy)-2H-1-benzopyran-2-one (compound (326)), 3-geranyloxy-4-hydroxy-8-(2-hydroxyethoxy)-2H-1-benzopyran-2-one (compound (327)), 3-prenyloxy-4-hydroxy-8-(2-hydroxyethoxy)-2H-1-benzopyran-2-one (compound (328)), 3-methoxy-4-hydroxy-8-(3-hydroxypropyloxy)-2H-1-benzopyran-2-one (compound (329)), 3-ethoxy-4-hydroxy-8-(3-hydroxypropyloxy)-2H-1-benzopyran-2-one (compound (330)), 3-butoxy-4-hydroxy-8-(3-hydroxypropyloxy)-2H-1-benzopyran-2-one (compound (331)), 3-hexyloxy-4-hydroxy-8-(2-hydropropyloxy)-2H-1-benzopyran-2-one (compound (332)), 3-(2-methylpentyloxy)-4-hydroxy-8-(3-hydroxypropyloxy)-2H-1-benzopyran-2-one (compound (333)), 3-octyloxy-4-hydroxy-8-(3-hydroxypropyloxy)-2H-1-benzopyran-2-one (compound (334)), 3-decyloxy-4-hydroxy-8-(3-hydroxypropyloxy)-2H-1-benzopyran-2-one (compound (335)), 3-(1-propenyloxy)-4-hydroxy-8-(3-hydroxypropyloxy)-2H-1-benzopyran-2-one (compound (336)), 3-(1-octenyloxy)-4-hydroxy-8-(3-hydroxypropyloxy)-2H-1-benzopyran-2-one (compound (337)), 3-geranyloxy-4-hydroxy-8-(3-hydroxypropyloxy)-2H-1-benzopyran-2-one (compound (338)), 3-ethoxy-4-hydroxy-8-(4-hydroxybutoxy)-2H-1-benzopyran-2-one (compound (339)), 3-butoxy-4-hydroxy-8-(4-hydroxybutoxy)-2H-1-benzopyran-2-one (compound (340)), 3-(s-butoxy)-4-hydroxy-8-(4-hydroxybutoxy)-2H-1-benzopyran-2-one (compound (341)), 3-hexyloxy-4-hydroxy-8-(4-hydroxybutoxy)-2H-1-benzopyran-2-one (compound (342)), 3-(1-ethylpentyloxy)-4-hydroxy-8-(4-hydroxybutoxy)-2H-1-benzopyran-2-one (compound (343)), 3-octyloxy-4-hydroxy-8-(4-hydroxybutoxy)-2H-1-benzopyran-2-one (compound (344)), 3-(1-butenyloxy)-4-hydroxy-8-(4-hydroxybutoxy)-2H-1-benzopyran-2-one (compound (345)), 3-prenyloxy-4-hydroxy-8-(4-hydroxybutoxy)-2H-1-benzopyran-2-one (compound (346)), 3-ethoxy-4-hydroxy-8-(2,3-dihydroxypropyloxy)-2H-1-benzopyran-2-one (compound (347)), 3-butoxy-4-hydroxy-8-(2,3-dihydroxypropyloxy)-2H-1-benzopyran-2-one (compound (348)), 3-hexyloxy-4-hydroxy-8-(2,3-dihydroxypropyloxy)-2H-1-benzopyran-2-one (compound (349)), 3-octyloxy-4-hydroxy-8-(2,3-dihydroxypropyloxy)-2H-1-benzopyran-2-one (compound (350)), 3-decyloxy-4-hydroxy-8-(2,3-dihydroxypropyloxy)-2H-1-benzopyran-2-one (compound (351)), 3-(1-hexenyloxy)-4-hydroxy-8-(2,3-dihydroxypropyloxy)-2H-1-benzopyran-2-one (compound (352)), 3-(3-methyl-2-butenyloxy)-4-hydroxy-8-(2,3-dihydroxypropyloxy)-2H-1-benzopyran-2-one (compound (353)), 3-methoxy-4-hydroxy-8-(3,4-dihydroxybutoxy)-2H-1-benzopyran-2-one (compound (354)), 3-ethoxy-4-hydroxy-8-(3,4-dihydroxybutoxy)-2H-1-benzopyran-2-one (compound (355)), 3-hexyloxy-4-hydroxy-8-(3,4-dihydroxybutoxy)-2H-1-benzopyran-2-one (compound (356)), 3-octyloxy-4-hydroxy-8-(3,4-dihydroxybutoxy)-2H-1-benzopyran-2-one (compound (357)), 3-(1-propenyloxy)-4-hydroxy-8-(3,4-dihydroxybutoxy)-2H-1-benzopyran-2-one (compound (358)), 3-(1-octenyloxy)-4-hydroxy-8-(3,4-dihydroxybutoxy)-2H-1-benzopyran-2-one (compound (359)), 3-geranyloxy-4-hydroxy-8-(3,4-dihydroxybutoxy)-2H-1-benzopyran-2-one (compound (360)), 3-methoxy-4-hydroxy-8-hydroxycarbonylmethoxy-2H-1-benzopyran-2-one (compound (361)), 3-ethoxy-4-hydroxy-8-hydroxycarbonylmethoxy-2H-1-benzopyran-2-one (compound (362)), 3-propyloxy-4-hydroxy-8-hydroxycarbonylmethoxy-2H-1-benzopyran-2-one (compound (363)), 3-isopropyloxy-4-hydroxy-8-hydroxycarbonylmethoxy-2H-1-benzopyran-2-one (compound (364)), 3-butoxy-4-hydroxy-8-hydroxycarbonylmethoxy-2H-1-benzopyran-2-one (compound (365)), 3-(s-butoxy)-4-hydroxy-8-hydroxycarbonylmethoxybenzopyran-2-one (compound (366)), 3-pentyloxy-4-hydroxy-8-hydroxycarbonylmethoxy-2H-1-benzopyran-2-one (compound (367)), 3-hexyloxy-4-hydroxy-8-hydroxycarbonylmethoxy-2H-1-benzopyran-2-one (compound (368)), 3-(2-methylpentyloxy)-4-hydroxy-8-hydroxycarbonylmethoxy-2H-1-benzopyran-2-one (compound (369)), 3-heptyloxy-4-hydroxy-8-hydroxycarbonylmethoxy-2H-1-benzopyran-2-one (compound (370)), 3-(1-ethylpentyloxy)-4-hydroxy-8-hydroxycarbonylmethoxy-2H-1-benzopyran-2-one (compound (371)), 3-(4-ethylpentyloxy)-4-hydroxy-8-hydroxycarbonylmethoxy-2H-1-benzopyran-2-one (compound (372)), 3-(1-ethylbutoxy)-4-hydroxy-8-hydroxycarbonylmethoxy-2H-1-benzopyran-2-one (compound (373)), 3-octyloxy-4-hydroxy-8-hydroxycarbonylmethoxy-2H-1-benzopyran-2-one (compound (374)), 3-(1-ethylhexyloxy)-4-hydroxy-8-hydroxycarbonylmethoxy-2H-1-benzopyran-2-one (compound (375)), 3-decyloxy-4-hydroxy-8-hydroxycarbonylmethoxy-2H-1-benzopyran-2-one (compound (376)), 3-vinyloxy-4-hydroxy-8-hydroxycarbonylmethoxy-2H-1-benzopyran-2-one (compound (377)), 3-(1-propenyloxy)-4-hydroxy-8-hydroxycarbonylmethoxy-2H-1-benzopyran-2-one (compound (378)), 3-(1-butenyloxy)-4-hydroxy-8-hydroxycarbonylmethoxy-2H-1-benzopyran-2-one (compound (379)), 3-(1-hexenyloxy)-4-hydroxy-8-hydroxycarbonylmethoxy-2H-1-benzopyran-2-one (compound (380)), 3-(1-octenyloxy)-4-hydroxy-8-hydroxycarbonylmethoxy-2H-1-benzopyran-2-one (compound (381)), 3-(1-decenyloxy)-4-hydroxy-8-hydroxycarbonylmethoxy-2H-1-benzopyran-2-one (compound (382)), 3-(3-methyl-2-butenyloxy)-4-hydroxy-8-hydroxycarbonylmethoxy-2H-1-benzopyran-2-one (compound (383)), 3-geranyloxy-4-hydroxy-8-hydroxycarbonylmethoxy-2H-1-benzopyran-2-one (compound (384)), 3-prenyloxy-4-hydroxy-8-hydroxycarbonylmethoxy-2H-1-benzopyran-2-one (compound (385)), 3-methoxy-4-hydroxy-8-(2-hydroxycarbonylethoxy)-2H-1-benzopyran-2-one (compound (386)), 3-ethoxy-4-hydroxy-8-(2-hydroxycarbonylethoxy)-2H-1-benzopyran-2-one (compound (387)), 3-butoxy-4-hydroxy-8-(2-hydroxycarbonylethoxy)-2H-1-benzopyran-2-one (compound (388)), 3-hexyloxy-4-hydroxy-8-(2-hydroxycarbonylethoxy)-2H-1-benzopyran-2-one (compound (389)), 3-octyloxy-4-hydroxy-8-(2-hydroxycarbonylethoxy)-2H-1-benzopyran-2-one (compound (390)), 3-(1-propenyloxy)-4-hydroxy-8-(2-hydroxycarbonylethoxy)-2H-1-benzopyran-2-one (compound (391)), 3-(1-octenyloxy)-4-hydroxy-8-(2-hydroxycarbonylethoxy)-2H-1-benzopyran-2-one (compound (392)), 3-geranyloxy-4-hydroxy-8-(2-hydroxycarbonylethoxy)-2H-1-benzopyran-2-one (compound (393)), 3-ethoxy-4-hydroxy-8-(3-hydroxycarbonylpropyloxy)-2H-1-benzopyran-2-one (compound (394)), 3-butoxy-4-hydroxy-8-(3-hydroxycarbonylpropyloxy)-2H-1-benzopyran-2-one (compound (395)), 3-hexyloxy-4-hydroxy-8-(3-hydroxycarbonylpropyloxy)-2H-1-benzopyran-2-one (compound (396)), 3-octyloxy-4-hydroxy-8-(3-hydroxycarbonylpropyloxy)-2H-1-benzopyran-2-one (compound (397)), 3-(1-butenyloxy)-4-hydroxy-8-(3-hydroxycarbonylpropyloxy)-2H-1-benzopyran-2-one (compound (398)), 3-prenyloxy-4-hydroxy-8-(3-hydroxycarbonylpropyloxy)-2H-1-benzopyran-2-one (compound (399)), 3-ethoxy-4-hydroxy-8-(4-hydroxycarbonylbutoxy)-2H-1-benzopyran-2-one (compound (400)), 3-butoxy-4-hydroxy-8-(4-hydroxycarbonylbutoxy)-2H-1-benzopyran-2-one (compound (401)), 3-hexyloxy-4-hydroxy-8-(4-hydroxycarbonylbutoxy)-2H-1-benzopyran-2-one (compound (402)), 3-octyloxy-4-hydroxy-8-(4-hydroxycarbonylbutoxy)-2H-1-benzopyran-2-one (compound (403)), and 3-(1-octenyloxy)-4-hydroxy-8-(4-hydroxycarbonylbutoxy)-2H-1-benzopyran-2-one (compound (404)).

As used herein, the term "physiologically acceptable salts" refers to alkali addition salts of the compounds described above, and examples thereof include nontoxic salts such as sodium salts, potassium salts, magnesium salts, calcium salts, and ammonium salts. The physiologically acceptable salts of the benzopyran derivatives represented by the general formula (II) can be produced from the benzopyran derivatives represented by the general formula (II) obtained by the method described above, using known techniques.

Since benzopyran derivatives represented by the general formula (II) and physiologically acceptable salts thereof used in the present invention have low toxicity and have an action of inhibiting both immediate and delayed type allergic reactions as will be described hereinafter in the Examples, they are markedly useful as antiallergic agents for the treatment or prevention of various allergic diseases.

As used herein, "allergic diseases" refer to those resulting from excess activation of the biological immune mechanism caused by extrinsic or intrinsic antigens, and examples thereof include immediate type asthma, delayed type asthma, bronchial asthma, pediatric asthma, nasal obstruction, allergic dermatitis, urticaria, eczema, allergic conjunctivitis, allergic rhinitis, hay fever, food allergy, allergic gastroenteritis, allergic colitis, drug allergy, contact dermatitis, and autoimmune disease.

The antiallergic agent which includes the benzopyran derivatives represented by the general formula (II) and physiologically acceptable salts thereof as the active ingredient can be administered orally or parenterally (for example, intravenous injection, subcutaneous injection, percutaneous absorption, and rectal administration). Such a pharmaceutical agent can be made into various administration forms according to the purpose, such as tablets, capsules, granules, fine subtilaes, powders, troches, sublingual tablets, suppositories, ointments, injections, emulsions, suspensions, medicated syrups, and chewable preparations.

These administration forms can be prepared in accordance with known techniques making use of nontoxic additives which are commonly used in these types of drugs, such as excipients, bonding agents, disintegrators, lubricants, preservatives, anti-oxidative agents, isotonic agents, buffering agents, coating agents, sweetening agents, dissolving agents, bases, dispersing agents, stabilizing agents, and coloring agents. Specific examples of these nontoxic additives are listed below.

Firstly, examples of the excipient include starch and derivatives of starch (for example, dextrin and carboxymethyl starch), cellulose and derivatives of cellulose (for example, methyl cellulose and hydroxypropylmethyl cellulose), saccharides (for example, lactose, sucrose, and glucose), silicic acid and silicates (for example, naturally occurring aluminum silicate, and magnesium silicate), carbonates (for example, calcium carbonate, magnesium carbonate, and sodium hydrogencarbonate), aluminum magnesium hydroxide, synthetic hydrotalcite, polyoxyethylene derivatives, glycerin monostearate, and sorbitan monooleate.

Examples of the bonding agent include starch and starch derivatives (for example, alpha starches and dextrin), cellulose and derivatives of cellulose (for example, ethyl cellulose, sodium carboxymethyl cellulose, and hydroxypropylmethyl cellulose), gum arabic, tragacanth, gelatin, saccharides (for example, glucose and sucrose), ethanol, and polyvinyl alcohols.

Examples of the disintegrator include starch and starch derivatives (for example, carboxymethyl starch and hydroxypropyl starch), cellulose and cellulose derivatives (for example, sodium carboxymethyl cellulose, crystal cellulose, and hydroxypropylmethyl cellulose), carbonates (for example, calcium carbonate and calcium hydrogencarbonate), tragacanth, gelatins, and agar.

Examples of the lubricant include stearic acid, calcium stearate, magnesium stearate, talc, silicic acid and its salts (for example, light silicic anhydrides and naturally occurring aluminum silicates), titanium oxide, calcium hydrogen phosphate, dry aluminum hydroxide gel, and macrogol.

Examples of the preservative include p-hydroxybenzoates, sulfites (for example, sodium sulfites and sodium pyrosulfites), phosphates (for example, sodium phosphates, calcium polyphosphates, sodium polyphosphates, and sodium methaphosphate), alcohols (for example, chlorobutanol and benzyl alcohol), benzalkonium chloride, benzethonium chloride, phenol, cresol, chlorocresol, dihydroacetic acid, sodium dihydroacetate, glycerin sorbic acid, and saccharides.

Examples of the anti-oxidative agent include sulfites (for example, sodium sulfite and sodium hydrogen sulfite, rongalite, erythorbic acid, L-ascorbic acid, cysteine, thioglycerol, butylhydroxyanisol, dibutylhydroxytoluene, propyl gallate, ascorbyl palmitate, and dl-α-tocopherol.

Examples of the isotonic agent include sodium chloride, sodium nitrate, potassium nitrate, dextrin, glycerin, and glucose. Examples of the buffering agent include sodium carbonate, hydrochloric acid, boric acid, and phosphates (for example, sodium hydrogenphosphate).

Examples of the coating agent include cellulose derivatives (for example, hydroxypropyl cellulose, cellulose acetate phthalate, and hydroxypropylmethyl cellulose phthalate), shellac, polyvinylpyrrolidone, polyvinylpyridines (for example, poly-2-vinylpyridine and poly-2-vinyl-5-ethylpyridine), polyvinylacetyl diethylaminoacetate, polyvinyl alcohol phthalate, methacrylate, and methacrylate copolymers.

Examples of the sweetening agent include saccharides (for example, glucose, sucrose, and lactose), sodium saccharin, and sugar alcohols. Examples of the dissolving agents include ethylenediamine, nicotinamide, sodium saccharin, citric acid, citrates, sodium benzoic acid, soaps, polyvinylpyrrolidone, polysolvates, sorbitan fatty acid esters, glycerin, propylene glycol, and benzyl alcohols.

Examples of the base include fats (for example, lard), vegetable oils (for example, olive oil and sesame oil), animal oil, lanolin acid, vaseline, paraffin, wax, resins, bentonite, glycerin, glycol oils, and higher alcohols (for example, stearyl alcohol and cetanol).

Examples of the dispersing agent include gum arabic, tragacanth, cellulose derivatives (for example, methyl cellulose), stearic acid polyesters, sorbitan sesquioleate, aluminum monostearate, sodium alginate, polysolvates, and sorbitan fatty acid esters. Examples of the stabilizing agent include sulfites (for example, sodium hydrogen sulfite), nitrogen, and carbon dioxide.

Though the content of the benzopyran derivatives represented by the general formula (II) in these pharmaceutical preparations varies depending on the administration forms, it may be contained preferably in a concentration of from 0.01 to 100% by weight.

The dosage of the antiallergic agent of the present invention can be varied over a broad range depending on each warm-blooded animal, including humans, to be treated, the extent of each disease, and the doctor's judgment. In general, however, it may be administered in a dosage of from 0.01 to 50 mg, and preferably from 0.05 to 10 mg, as the active ingredient per day per kg body weight in the case of oral administration or in a dosage of from 0.01 to 10 mg, and preferably from 0.01 to 5 mg, as the active ingredient per day per kg body weight in the case of parenteral administration. The daily dosage described above may be used in one portion or in divided portions and changed arbitrarily in accordance with the extent of the disease and the doctor's judgment.

EXAMPLES

The following Examples are intended to illustrate the preparation of the compounds of this invention and the pharmaceutical compositions of these compounds; however, these examples are intended to illustrate the invention and not to be construed as limiting the scope of the invention. First, Preparation Examples of novel benzopyran derivatives used in the present invention are described, and then the results of the pharmacological tests of the compounds of the present invention are described.

Reference Example 1

Synthesis of 3-ethoxy-4-hydroxy-5-(2-acetoxyethoxy)-2H-1-benzopyran-2-one 2.24 g (0.02 mol) of potassium t-butoxide was dissolved in 4 ml of dimethylformamide (hereinafter abbreviated to DMF). To the solution, 2.22 g (0.01 mol) of a solution prepared by dissolving 3-ethoxy-4,5-dihydroxy-2H-1-benzopyran-2-one in 16 ml of DMF was added dropwise at 15–25° C., followed by continuous stirring for 30 minutes.

To this reaction solution, 1.67 g (0.01 mol) of 2-bromoethyl acetate was added, and the mixture was continuously stirred at the same temperature for 3 hours. The reaction solution was added to 105 ml of 3N-hydrochloric acid, and after extracting twice with 50 ml of ethyl acetate, the extract was dried over magnesium sulfate. After filtering the ethyl acetate solution, the filtrate was concentrated under reduced pressure to yield 4.86 g of a crude product. The resulting crude product was purified by silica gel column chromatography (eluent: hexane/ethyl acetate=2/1) to yield 1.89 g of the titled compound (yield: 71%)

$^1$H-NMR(CDCl$_3$, δ-TMS): 9.31(bs, 1H), 6.70–7.40(m, 3H), 4.43(t, 2H, J=5.0 Hz), 4.22(t, 2H, J=5.0 Hz), 4.10(q, 2H, J=6.0 Hz), 2.12(s, 3H), 1.27(t, 3H, J=7.0 Hz)

IR(KBr, cm$^{-1}$): 3300, 3005, 1725, 1600, 1230

Elemental analysis for C$_{15}$H$_{16}$O$_7$ Calculated (%): C58.44; H5.23; O36.33 Found (%): C58.39; H5.22; O36.39

Example 1

Synthesis of 3-ethoxy-4-hydroxy-5-(2-hydroxyethoxy)-2H-1-benzopyran-2-one (Compound (2))

3.08 g (0.01 mol) of 3-ethoxy-4-hydroxy-5-(2-acetoxyethoxy)-2H-1-benzopyran-2-one was added to 20 ml of 1N-sodium hydroxide-ethanol solution, followed by stirring at room temperature for 30 minutes.

The reaction solution was neutralized with 105 ml of 0.2N hydrochloric acid and then extracted with ethyl acetate. The organic layer was concentrated under reduced pressure, and the resulting crude product was purified by silica gel column chromatography (eluent: hexane/acetone=2/1) and then recrystallized (solvent for recrystallization: ethyl acetate/hexane=3/10) to yield 2.36 g of the titled compound (yield: 88%).

$^1$H-NMR(DMSO-d$_6$, δ-TMS): 9.27(bs, 1H), 6.70–7.40 (m, 3H), 4.86(bs, 1H), 4.16(t, 2H, J=5.0 Hz), 4.08(q, 2H, J=6.0 Hz), 3.77(t, 2H, J=5.0 Hz), 1.25(t, 3H, J=7.0 Hz)

IR(KBr, cm$^{-1}$): 3300, 3005, 1670, 1600, 1230

Elemental analysis for C$_{13}$H$_{14}$O$_6$ Calculated (%): C58.64; H5.30; O36.06 Found (%): C58.59; H5.40; O36.01

Example 2

Synthesis of 3-butoxy-4-hydroxy-5-(2-hydroxyethoxy)-2H-1-benzopyran-2-one (compound (5))

In the same manner as in Reference Example 1, except that an equimolar amount of 3-butoxy-4,5-dihydroxy-2H-1-benzopyran-2-one was used in place of 3-ethoxy-4,5-dihydroxy-2H-1-benzopyran-2-one in Reference Example 1, 3-butoxy-4-hydroxy-5-(2-acetoxyethoxy)-2H-1-benzopyran-2-one was obtained.

In the same manner as in Example 1, except that an equimolar amount of 3-butoxy-4-hydroxy-5-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.27(bs, 1H), 6.70–7.40 (m, 3H), 4.86(bs, 1H), 4.07(t, 2H, J=6.0 Hz), 3.88(t, 2H, J=5.0 Hz), 3.77(t, 2H, J=6.0 Hz), 1.30–1.80(m, 4H), 0.86(t, 3H, J=7.0 Hz)

IR(KBr, cm$^{-1}$): 3300, 3005, 1670, 1600, 1230

Elemental analysis for C$_{15}$H$_{18}$O$_6$ Calculated (%): C61.21; H6.17; O32.62 Found (%): C61.15; H6.26; O32.59

Example 3

Synthesis of 3-hexyloxy-4-hydroxy-5-(2-hydroxyethoxy)-2H-1-benzopyran-2-one (compound (8))

In the same manner as in Reference Example 1, except that an equimolar amount of 3-hexyloxy-4,5-dihydroxy-2H-1-benzopyran-2-one was used in place of 3-ethoxy-4,5-dihydroxy-2H-1-benzopyran-2-one in Reference Example 1, 3-hexyloxy-4-hydroxy-5-(2-acetoxyethoxy)-2H-1-benzopyran-2-one was obtained.

In the same manner as in Example 1, except that an equimolar amount of 3-hexyloxy-4-hydroxy-5-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.29(bs, 1H), 6.70–7.40 (m, 3H), 4.90(bs, 1H), 4.07(t, 2H, J=6.0 Hz), 3.87(t, 2H, J=5.0 Hz), 3.75(t, 2H, J=6.0 Hz), 1.30–1.80(m, 8H), 0.86(t, 3H, J=7.0 Hz)

IR(KBr, cm$^{-1}$): 3300, 3005, 1670, 1600, 1230

Elemental analysis for C$_{17}$H$_{22}$O$_6$ Calculated (%): C63.34; H6.88; O29.79 Found (%): C63.40; H6.91; O29.69

Example 4

Synthesis of 3-(4-methylpentyloxy)-4-hydroxy-5-(2-hydroxyethoxy)-2H-1-benzopyran-2-one (Compound (12))

In the same manner as in Reference Example 1, except that an equimolar amount of 3-(4-methylpentyloxy)-4,5-dihydroxy-2H-1-benzopyran-2-one was used in place of 3-ethoxy-4,5-dihydroxy-2H-1-benzopyran-2-one in Reference Example 1, 3-(4-methylpentyloxy)-4-hydroxy-5-(2-acetoxyethoxy)-2H-1-benzopyran-2-one was obtained.

In the same manner as in Example 1, except that an equimolar amount of 3-(4-methylpentyloxy)-4-hydroxy-5-(2-acetoxyethoxy)-2H-1-benzopyran-2-one was used in place 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.31(bs, 1H), 6.70–7.40 (m, 3H), 4.86(bs, 1H), 4.05(t, 2H, J=6.0 Hz), 3.85(t, 2H, J=5.0 Hz), 3.78(t, 2H, J=6.0 Hz), 1.20–1.80(m, 5H), 0.87(d, 6H, J=3.0 Hz)

IR(KBr, cm$^{-1}$): 3300, 3000, 1660, 1600, 1230

Elemental analysis for C$_{17}$H$_{22}$O$_6$ Calculated (%): C63.34; H6.88; O29.79 Found (%): C63.30; H6.81; O29.89

Example 5

Synthesis of 3-octyloxy-4-hydroxy-5-(2-hydroxyethoxy)-2H-1-benzopyran-2-one (compound (14))

In the same manner as in Reference Example 1, except that an equimolar amount of 3-octyloxy-4,5-dihydroxy-2H-1-benzopyran-2-one was used in place of 3-ethoxy-4,5-dihydroxy-2H-1-benzopyran-2-one in Reference Example 1, 3-octyloxy-4-hydroxy-5-(2-acetoxyethoxy)-2H-1-benzopyran-2-one was obtained.

In the same manner as in Example 1, except that an equimolar amount of 3-octyloxy-4-hydroxy-5-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.31(bs, 1H), 6.70–7.40 (m, 3H), 4.90(bs, 1H), 4.06(t, 2H, J=6.0 Hz), 3.89(t, 2H, J=5.0 Hz), 3.76(t, 2H, J=6.0 Hz), 1.20–1.80(m, 12H), 0.87(t, 3H, J=6.0 Hz)

IR(KBr, cm$^{-1}$): 3300, 3005, 1660, 1610, 1230

Elemental analysis for C$_{19}$H$_{26}$O$_6$ Calculated (%): C65.12; H7.48; O27.40 Found (%): C65.02; H7.50; O27.48

Example 6

Synthesis of 3-geranyloxy-4-hydroxy-5-(2-hydroxyethoxy)-2H-1-benzopyran-2-one
(Compound (24))

In the same manner as in Reference Example 1, except that an equimolar amount of 3-geranyloxy-4,5-dihydroxy-2H-1-benzopyran-2-one was used in place of 3-ethoxy-4,5-dihydroxy-2H-1-benzopyran-2-one in Reference Example 1, 3-geranyloxy-4-hydroxy-5-(2-acetoxyethoxy)-2H-1-benzopyran-2-one was obtained.

In the same manner as in Example 1, except that an equimolar amount of 3-geranyloxy-4-hydroxy-5-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.30(bs, 1H), 6.70–7.40 (m, 3H), 5.40(m, 1H), 5.25(m, 1H), 5.10(m, 1H), 4.88(bs, 1H), 4.23(m, 2H), 4.05(t, 2H, J=6.0 Hz), 3.78(t, 2H, J=6.0 Hz), 1.50–2.15(m, 13H)

IR(KBr, cm$^{-1}$): 3300, 3005, 1660, 1610, 1230

Elemental analysis for C$_{21}$H$_{26}$O$_6$ Calculated (%): C67.36; H7.00; O25.64 Found (%): C67.31; H6.97; O25.72

Example 7

Synthesis of 3-butoxy-4-hydroxy-5-(3-hydroxypropyloxy)-2H-1-benzopyran-2-one
(Compound (28))

In the same manner as in Reference Example 1, except that an equimolar amount of 3-butoxy-4,5-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-butoxy-4-hydroxy-5-(3-acetoxypropoxy)-2H-1-benzopyran-2-one was obtained.

In the same manner as in Example 1, except that an equimolar amount of 3-butoxy-4-hydroxy-5-(3-acetoxypropoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.27(bs, 1H), 6.70–7.40 (m, 3H), 4.89(bs, 1H), 3.90–4.00(m, 4H), 3.70(t, 2H, J=6.0 Hz), 1.30–1.95(m, 6H), 0.85(t, 3H, J=7.0 Hz)

IR(KBr, cm$^{-1}$): 3300, 3005, 1670, 1600, 1230

Elemental analysis for C$_{16}$H$_{20}$O$_6$ Calculated (%): C62.32; H6.54; O31.14 Found (%): C62.36; H6.63; O31.01

Example 8

Synthesis of 3-hexyloxy-4-hydroxy-5-(3-hydroxypropyloxy)-2H-1-benzopyran-2-one
(Compound (29))

In the same manner as in Reference Example 1, except that an equimolar amount of 3-hexyloxy-4,5-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-hexyloxy-4-hydroxy-5-(3-acetoxypropoxy)-2H-1-benzopyran-2-one was obtained.

In the same manner as in Example 1, except that an equimolar amount of 3-hexyloxy-4-hydroxy-5-(3-acetoxypropoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.29(bs, 1H), 6.70–7.40 (m, 3H), 4.90(bs, 1H), 3.90–4.00(m, 4H), 3.70(t, 2H, J=6.0 Hz), 1.20–1.95(m, 10H), 0.87(t, 3H, J=7.0 Hz)

IR(KBr, cm$^{-1}$): 3300, 3005, 1670, 1600, 1230

Elemental analysis for C$_{18}$H$_{24}$O$_6$ Calculated (%): C64.27; H7.19; O28.54 Found (%): C64.35; H7.22; O28.43

Example 9

Synthesis of 3-octyloxy-4-hydroxy-5-(3-hydroxypropyloxy)-2H-1-benzopyran-2-one
(compound (31))

In the same manner as in Reference Example 1, except that an equimolar amount of 3-octyloxy-4,5-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-octyloxy-4-hydroxy-5-(3-acetoxypropoxy)-2H-1-benzopyran-2-one was obtained.

In the same manner as in Example 1, except that an equimolar amount of 3-octyloxy-4-hydroxy-5-(3-acetoxypropoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.30(bs, 1H), 6.70–7.40 (m, 3H), 4.87(bs, 1H), 3.90–4.00(m, 4H), 3.72(t, 2H, J=6.0 Hz), 1.20–1.95(m, 14H), 0.89(t, 3H, J=7.0 Hz)

IR(KBr, cm$^{-1}$): 3300, 3005, 1670, 1600, 1230

Elemental analysis for C$_{20}$H$_{28}$O$_6$ Calculated (%): C65.91; H7.74; O26.34 Found (%): C65.84; H7.83; O26.33

Example 10

Synthesis of 3-ethoxy-4-hydroxy-5-(3-hydroxybutoxy)-2H-1-benzopyran-2-one
(Compound (36))

In the same manner as in Reference Example 1, except that 3-bromobutyl acetate was used in place of 2-bromoethyl acetate in Reference Example 1, 3-ethoxy-4-hydroxy-5-(3-acetoxybutoxy)-2H-1-benzopyran-2-one was obtained.

In the same manner as in Example 1, except that an equimolar amount of 3-ethoxy-4-hydroxy-5-(3-acetoxybutoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.28(bs, 1H), 6.70–7.40 (m, 3H), 4.83(bs, 1H), 4.19(t, 2H, J=5.0 Hz), 4.00(q, 2H, J=6.0 Hz), 3.78(t, 2H, J=5.0 Hz), 1.40–1.75(m, 4H), 1.23(t, 3H, J=7.0 Hz)

IR(KBr, cm$^{-1}$): 3300, 3005, 1670, 1600, 1230

Elemental analysis for C$_{15}$H$_{18}$O$_6$ Calculated (%): C61.21; H6.17; O32.62 Found (%): C61.10; H6.21; O32.69

Example 11

Synthesis of 3-butoxy-4-hydroxy-5-(3-hydroxybutoxy)-2H-1-benzopyran-2-one (Compound (37))

In the same manner as in Reference Example 1, except that an equimolar amount of 3-butoxy-4,5-dihydroxy-2H-1-benzopyran-2-one was used in place of 3-ethoxy-4,5-dihydroxy-2H-1-benzopyran-2-one, and 3-bromobutyl acetate was used in place of 2-bromoethyl acetate in Reference Example 1, 3-butoxy-4-hydroxy-5-(3-acetoxybutoxy)-2H-1-benzopyran-2-one was obtained.

In the same manner as in Example 1, except that an equimolar amount of 3-butoxy-4-hydroxy-5-(3-acetoxybutoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.31(bs, 1H), 6.70–7.40 (m, 3H), 4.85(bs, 1H), 3.90–4.00(m, 4H), 3.73(t, 2H, J=6.0 Hz), 1.30–1.95(m, 8H), 0.85(t, 3H, J=7.0 Hz)

IR(KBr, cm$^{-1}$): 3300, 3005, 1670, 1600, 1230

Elemental analysis for C$_{17}$H$_{22}$O$_6$ Calculated (%): C63.34; H6.88; O29.78 Found (%): C63.36; H6.97; O29.67

Reference Example 2

Synthesis of 3-hexyloxy-4-hydroxy-5-(2,2-dimethyl-1,3-dioxolane-4-methoxy)-2H-1-benzopyran-2-one 2.24 g (0.02 mol) of potassium t-butoxide was dissolved in 4 ml of DMF. To the solution, 2.78 g (0.01 mol) of a solution prepared by dissolving 3-hexyloxy-4,5-dihydroxy-2H-1-benzopyran-2-one in 16 ml of DMF was added dropwise at 15–25° C., followed by continuous stirring for 30 minutes.

To this reaction solution, 2.86 g (0.01 mol) of 2,2-dimethyl-1,3-dioxolan-4-ylmethylparatoluene sulfonate was added, and the mixture was continuously stirred at the same temperature for 3 hours. The reaction solution was added to 105 ml of hydrochloric acid having a concentration of 3 mol/L, and after extracting twice with 50 ml of ethyl acetate, the extract was dried over magnesium sulfate. After filtering the ethyl acetate solution, the filtrate was concentrated under reduced pressure to yield a crude product. The resulting crude product was purified by silica gel column chromatography (eluent: hexane/ethyl acetate=2/1) to yield 2.35 g of the titled compound (yield: 60%)

$^1$H-NMR(CDCl$_3$, δ-TMS) 9.20(bs, 1H), 6.70–7.40(m, 3H), 4.52(t, 2H, J=5.2 Hz), 3.90–4.21(m, 5H), 1.75(m, 2H), 1.48(s, 3H), 1.42(s, 3H), 1.20–1.41(m, 6H), 0.87(t, 3H, J=7.0 Hz)

IR(KBr, cm$^{-1}$): 3300, 3005, 1725, 1600, 1230

Elemental analysis for C$_{21}$H$_{28}$O$_7$ Calculated (%): C64.27; H7.19; O28.54 Found (%): C64.23; H7.28; O28.49

Example 12

Synthesis of 3-hexyloxy-4-hydroxy-5-(2,3-dihydroxypropyloxy)-2H-1-benzopyran-2-one (Compound (46))

3.92 g (0.01 mol) of 3-hexyloxy-4-hydroxy-5-(2,2-dimethyl-1,3-dioxolane-4-methoxy)-2H-1-benzopyran-2-one was added to 40 ml of a 80% acetic acid solution, followed by continuous stirring at 60° C. for 4 hours. The reaction solution was concentrated under reduced pressure, and after adding 40 ml of water to the concentrated solution, the mixture was extracted with ethyl acetate. The organic layer was concentrated under reduced pressure, and the resulting crude product was recrystallized from methanol to obtain 1.87 g of the titled compound (yield: 53%)

$^1$H-NMR(DMSO-d$_6$, δ-TMS): 9.33(bs, 1H), 6.70–7.40 (m, 3H), 5.00(s, 1H), 4.70(s, 1H), 3.81–4.11(m, 5H), 3.45(s, 2H), 1.69(m, 2H), 1.18–1.40(m, 6H), 0.86(t, 3H, J=7.0 Hz)

IR(KBr, cm$^{-1}$): 3420, 3005, 1680, 1610, 1260

Elemental analysis for C$_{18}$H$_{24}$O$_7$ Calculated (%): C61.35; H6.86; O31.78 Found (%): C61.28; H6.88; O31.84

Example 13

Synthesis of 3-butoxy-4-hydroxy-5-(2,3-dihydroxypropyloxy)-2H-1-benzopyran-2-one (compound (45))

In the same manner as in Reference Example 2, except that an equimolar amount of 3-butoxy-4,5-dihydroxy-2H-1-benzopyran-2-one was used in place of 3-hexyloxy-4,5-dihydroxy-2H-1-benzopyran-2-one in Reference Example 2, 3-butoxy-4-hydroxy-5-(2,2-dimethyl-1,3-dioxolane-4-methoxy)-2H-1-benzopyran-2-one was obtained.

In the same manner as in Example 12, except that an equimolar amount of 3-butoxy-4-hydroxy-5-(2,2-dimethyl-1,3-dioxolane-4-methoxy)-2H-1-benzopyran-2-one was used in place of 3-hexyloxy-4-hydroxy-5-(2,2-dimethyl-1,3-dioxolane-4-methoxy)-2H-1-benzopyran-2-one in Example 12, the titled compound was obtained.

$^1$H-NMR(DMSO-d$_6$, δ-TMS): 9.31(bs, 1H), 6.70–7.40 (m, 3H), 5.01(s, 1H), 4.70(s, 1H), 3.81–4.11(m, 5H), 3.45(s, 2H), 1.18–1.40(m, 4H), 0.86(t, 3H, J=7.0 Hz)

IR(KBr, cm$^{-1}$): 3420, 3005, 1680, 1610, 1260

Elemental analysis for C$_{16}$H$_{20}$O$_7$ Calculated (%) C59.25; H6.22; O34.53 Found (%): C59.21; H6.15; O34.64

Reference Example 3

Synthesis of 3-hexyloxy-4-hydroxy-5-ethoxycarbonylmethoxy-2H-1-benzopyran-2-one In the same manner as in Reference Example 2, except that an equimolar amount of ethyl bromoacetate was used in place of 2,2-dimethyl-1,3-dioxolan-4-ylmethylparatoluene sulfonate in Reference Example 2, the titled compound was obtained.

$^1$H-NMR(DMSO-d$_6$, δ-TMS): 9.27(bs, 1H), 6.70–7.40 (m, 3H), 4.90(s, 2H), 3.81–4.11(m, 4H), 1.69(m, 2H), 1.20–1.40(m, 9H), 0.86(t, 3H, J=7.0 Hz)

IR(KBr, cm$^{-1}$):3.420, 3005, 1750, 1610, 1260

Elemental analysis for C$_{19}$H$_{24}$O$_7$ Calculated (%): C62.62; H6.64; O30.73 Found (%): C62.53; H6.71; O30.76

Example 14

Synthesis of 3-hexyloxy-4-hydroxy-5-hydroxycarbonylmethoxy-2H-1-benzopyran-2-one (compound (65))

25 ml of ethanol was added to 3.64 g (0.01 mol) of 3-hexyloxy-4-hydroxy-5-ethoxycarbonylmethoxy-2H-1-benzopyran-2-one, and 25 ml of an aqueous 1 mol/L sodium hydroxide solution was added under ice cooling, followed by continuous stirring at room temperature for 4 hours. The reaction solution was added to 26 ml of hydrochloric acid having a concentration of 1 mol/L, and after extracting twice with 50 ml of ethyl acetate, the extract was dried over magnesium sulfate. After filtering the ethyl acetate solution, the filtrate was concentrated under reduced pressure, and the resulting crude product was recrystallized from methanol to obtain 2.4 g of the titled compound (yield: 74%)

$^1$H-NMR(DMSO-$d_6$, δ-TMS): 11.02(bs, 1H), 9.27(bs, 1H), 6.70–7.40(m, 3H), 4.88(s, 2H), 3.88(t, 2H, J=5.0 Hz), 1.69(m, 2H), 1.20–1.40(m, 6H), 0.86(t, 3H, J=7.0 Hz)

IR(KBr, cm$^{-1}$): 3420, 3005, 1750, 1610, 1260

Elemental analysis for $C_{17}H_{20}O_7$ Calculated (%): C60.71; H5.99; O33.30 Found (%): C60.67; H6.11; O33.22

Example 15

Synthesis of 3-ethoxy-4-hydroxy-5-hydroxycarbonylmethoxy-2H-1-benzopyran-2-one (compound (59))

In the same manner as in Reference Example 3, except that an equimolar amount of 3-ethoxy-4,5-dihydroxy-2H-1-benzopyran-2-one was used in place of 3-hexyloxy-4,5-dihydroxy-2H-1-benzopyran-2-one in Reference Example 3, 3-ethoxy-4-hydroxy-5-ethoxycarbonylmethoxy-2H-1-benzopyran-2-one was obtained.

In the same manner as in Example 14, except that an equimolar amount of 3-ethoxy-4-hydroxy-5-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.12(bs, 1H), 9.29(bs, 1H), 6.70–7.40(m, 3H), 4.88(s, 2H), 4.08(q, 2H, J=6.0 Hz), 1.25(t, 3H, J=7.0 Hz)

IR(KBr, cm$^{-1}$): 3420, 3005, 1750, 1610, 1260

Elemental analysis for $C_{13}H_{12}O_7$ Calculated (%): C55.72; H4.32; O39.97 Found (%): C55.64; H4.26; O40.10

Example 16

Synthesis of 3-butoxy-4-hydroxy-5-hydroxycarbonylmethoxy-2H-1-benzopyran-2-one (compound (62))

In the same manner as in Reference Example 3, except that an equimolar amount of 3-butoxy-4,5-dihydroxy-2H-1-benzopyran-2-one was used in place of 3-hexyloxy-4,5-dihydroxy-2H-1-benzopyran-2-one in Reference Example 3, 3-butoxy-4-hydroxy-5-ethoxycarbonylmethoxy-2H-1-benzopyran-2-one was obtained.

In the same manner as in Example 14, except that an equimolar amount of 3-butoxy-4-hydroxy-5-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.08(bs, 1H), 9.30(bs, 1H), 6.70–7.40(m, 3H), 4.88(s, 2H), 3.98(t, 2H, J=6.0 Hz), 1.30–1.95(m, 4H), 0.85(t, 3H, J=7.0 Hz)

IR(KBr, cm$^{-1}$): 3420, 3005, 1750, 1610, 1260

Elemental analysis for $C_{15}H_{16}O_7$ Calculated (%): C58.44; H5.23; O36.33 Found (%): C58.45; H5.29; O36.26

Example 17

Synthesis of 3-octyloxy-4-hydroxy-5-hydroxycarbonylmethoxy-2H-1-benzopyran-2-one (compound (71))

In the same manner as in Reference Example 3, except that an equimolar amount of 3-octyloxy-4,5-dihydroxy-2H-1-benzopyran-2-one was used in place of 3-hexyloxy-4,5-dihydroxy-2H-1-benzopyran-2-one in Reference Example 3, 3-octyloxy-4-hydroxy-5-ethoxycarbonylmethoxy-2H-1-benzopyran-2-one was obtained.

In the same manner as in Example 14, except that an equimolar amount of 3-octyloxy-4-hydroxy-5-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.06(bs, 1H), 9.26(bs, 1H), 6.70–7.40(m, 3H), 4.87(s, 2H), 3.99(t, 2H, J=6.0 Hz), 1.30–1.95(m, 12H), 0.85(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.69; H6.53; O30.78

Example 18

Synthesis of 3-geranyloxy-4-hydroxy-5-hydroxycarbonylmethoxy-2H-1-benzopyran-2-one (compound (81))

In the same manner as in Reference Example 3, except that an equimolar amount of 3-geranyloxy-4,5-dihydroxy-2H-1-benzopyran-2-one was used in place of 3-hexyloxy-4,5-dihydroxy-2H-1-benzopyran-2-one in Reference Example 3, 3-geranyloxy-4-hydroxy-5-ethoxycarbonylmethoxy-2H-1-benzopyran-2-one was obtained.

In the same manner as in Example 14, except that an equimolar amount of 3-geranyloxy-4-hydroxy-5-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.11(bs, 1H), 9.28(bs, 1H), 6.70–7.40(m, 3H), 5.40(m, 1H), 5.25(m, 1H), 5.10(m, 1H), 4.87(s, 2H), 4.23(m, 2H), 4.05(t, 2H, J=6.0 Hz), 3.78(t, 2H, J=6.0 Hz), 1.50–2.15(m, 13H)

IR(KBr, cm$^{-1}$): 3420, 3005, 1750, 1610, 1260

Elemental analysis for $C_{21}H_{24}O_7$ Calculated (%): C64.93; H6.23; O28.84 Found (%): C64.87; H6.31; O28.82

Example 19

Synthesis of 3-butoxy-4-hydroxy-5-(2-hydroxycarbonylethoxy)-2H-1-benzopyran-2-one (Compound (85))

In the same manner as in Reference Example 3, except that an equimolar amount of 3-butoxy-4,5-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-butoxy-4-hydroxy-5-(2-ethoxycarbonylethoxy)-2H-1-benzopyran-2-one was obtained.

In the same manner as in Example 14, except an equimolar amount of 3-butoxy-4-hydroxy-5-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.10(bs, 1H), 9.27(bs, 1H), 6.70–7.40(m, 3H), 4.45(t, 2H, J=5.0 Hz), 3.98(t, 2H, J=6.0 Hz), 3.18(t, 2H, J=5.0 Hz), 1.30–1.95(m, 4H), 0.87(t, 3H, J=7.0 Hz)

IR(KBr, cm$^{-1}$): 3420, 3005, 1750, 1610, 1260

Elemental analysis for $C_{16}H_{18}O_7$ Calculated (%): C59.62; H5.63; O34.75 Found (%): C59.66; H5.51; O34.83

Example 20

Synthesis of 3-hexyloxy-4-hydroxy-5-(2-hydroxycarbonylethoxy)-2H-1-benzopyran-2-one (compound (86))

In the same manner as in Reference Example 3, except that an equimolar amount of ethyl 3-bromopropionate was used in place of ethyl bromoacetate in Reference Example 3, 3-hexyloxy-4-hydroxy-5-(2-ethoxycarbonylethoxy)-2H-1-benzopyran-2-one was obtained.

In the same manner as in Example 14, except that an equimolar amount of 3-hexyloxy-4-hydroxy-5-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.13(bs, 1H), 9.27(bs, 1H), 6.70–7.40(m, 3H), 4.45(t, 2H, J=5.0 Hz), 3.98(t, 2H, J=6.0 Hz), 3.18(t, 2H, J=5.0 Hz), 1.69(m, 2H), 1.30–1.95(m, 8H), 0.88(t, 3H, J=7.0 Hz)

IR(KBr, cm$^{-1}$): 3420, 3005, 1750, 1610, 1260

Elemental analysis for $C_{18}H_{22}O_7$ Calculated (%): C61.70; H6.33; O31.97 Found (%): C61.58; H6.37; O32.05

Example 21

Synthesis of 3-octyloxy-4-hydroxy-5-(2-hydroxycarbonylethoxy)-2H-1-benzopyran-2-one (compound (87))

In the same manner as in Reference Example 3, except that an equimolar amount of 3-octyloxy-4,5-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-octyloxy-4-hydroxy-5-(2-ethoxycarbonylethoxy)-2H-1-benzopyran-2-one was obtained.

In the same manner as in Example 14, except that an equimolar amount of 3-octyloxy-4-hydroxy-5-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.12(bs, 1H), 9.28(bs, 1H), 6.70–7.40(m, 3H), 4.41(t, 2H, J=5.0 Hz), 3.98(t, 2H, J=6.0 Hz), 3.19(t, 2H, J=5.0 Hz), 1.69(m, 2H), 1.30–1.95(m, 12H), 0.88(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.51; H6.82; O29.67

Example 22

Synthesis of 3-hexyloxy-4-hydroxy-5-(3-hydroxycarbonylpropyloxy)-2H-1-benzopyran-2-one (Compound (93))

In the same manner as in Reference Example 3, except that an equimolar amount of ethyl 4-bromobutanoate was used in place of ethyl bromoacetate in Reference Example 3, 3-hexyloxy-4-hydroxy-5-(3-ethoxycarbonylpropoxy)-2H-1-benzopyran-2-one was obtained.

In the same manner as in Example 14, except that an equimolar amount of 3-hexyloxy-4-hydroxy-5-(3-ethoxycarbonylpropoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.12(bs, 1H), 9.28(bs, 1H), 6.70–7.40(m, 3H), 4.41(t, 2H, J=5.0 Hz), 3.98(t, 2H, J=6.0 Hz), 2.23(t, 2H, J=5.0 Hz), 1.30–2.00(m, 10H), 0.88(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.53; H6.67; O30.80

Example 23

Synthesis of 3-hexyloxy-4-hydroxy-5-(4-hydroxycarbonylbutoxy)-2H-1-benzopyran-2-one (compound (99))

In the same manner as in Reference Example 3, except that an equimolar amount of ethyl 5-bromopentanoate was used in place of ethyl bromoacetate in Reference Example 3, 3-hexyloxy-4-hydroxy-5-(4-ethoxycarbonylbutoxy)-2H-1-benzopyran-2-one was obtained.

In the same manner as in Example 14, except that an equimolar amount of 3-hexyloxy-4-hydroxy-5-(4-ethoxycarbonylbutoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.11(bs, 1H), 9.29(bs, 1H), 6.70–7.40(m, 3H), 4.40(t, 2H, J=5.0 Hz), 3.99(t, 2H, J=6.0 Hz), 2.23(t, 2H, J=5.0 Hz), 1.30–2.00(m, 12H), 0.88(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.46; H6.85; O29.69

Example 24

Synthesis of 3-ethoxy-4-hydroxy-6-(2-hydroxyethoxy)-2H-1-benzopyran-2-one (Compound (103))

In the same manner as in Reference Example 1, except that an equimolar amount of 3-ethoxy-4,6-hydroxy-2H-1-benzopyran-2-one was used in place of 3-ethoxy-4,5-dihydroxy-2H-1-benzopyran-2-one in Reference Example 1, 3-ethoxy-4-hydroxy-6-(2-acetoxyethoxy)-2H-1-benzopyran-2-one was obtained.

In the same manner as in Example 1, except that an equimolar amount of 3-butoxy-4-hydroxy-6-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.98(bs, 1H), 6.80–7.40 (m, 3H), 4.87(bs, 1H), 4.14(t, 2H, J=5.0 Hz), 4.08(q, 2H, J=6.0 Hz), 3.77(t, 2H, J=5.0 Hz), 1.25(t, 3H, J=7.0 Hz)

IR(KBr, cm$^{-1}$): 3300, 3005, 1670, 1600, 1230

Elemental analysis for $C_{13}H_{14}O_6$ Calculated (%): C58.64; H5.30; O36.06 Found (%): C58.68; H5.22; O36.10

Example 25

Synthesis of 3-butoxy-4-hydroxy-6-(2-hydroxyethoxy)-2H-1-benzopyran-2-one (compound (106))

In the same manner as in Reference Example 1, except that an equimolar amount of 3-butoxy-4,6-dihydroxy-2H-1- benzopyran-2-one was used in place of 3-ethoxy-4,5-dihydroxy-2H-1-benzopyran-2-one in Reference Example 1, 3-butoxy-4-hydroxy-6-(2-acetoxyethoxy)-2H-1-benzopyran-2-one was obtained.

In the same manner as in Example 1, except that an equimolar amount of 3-butoxy-4-hydroxy-6-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 9.96(bs, 1H), 6.80–7.20 (m, 3H), 4.85(bs, 1H), 4.09(t, 2H, J=6.0 Hz), 3.84(t, 2H, J=5.0 Hz), 3.77(t, 2H, J=6.0 Hz), 1.30–1.80(m, 4H), 0.88(t, 3H, J=7.0 Hz)

IR(KBr, cm$^{-1}$): 3300, 3005, 1670, 1600, 1230

Elemental analysis for $C_{15}H_{18}O_6$ Calculated (%): C61.21; H6.17; O32.62 Found (%): C61.30; H6.23; O32.47

Example 26

Synthesis of 3-hexyloxy-4-hydroxy-6-(2-hydroxyethoxy)-2H-1-benzopyran-2-one (compound (109))

In the same manner as in Reference Example 1, except that an equimolar amount of 3-hexyloxy-4,6-dihydroxy-2H-1-benzopyran-2-one was used in place of 3-ethoxy-4,5-dihydroxy-2H-1-benzopyran-2-one in Reference Example 1, 3-hexyloxy-4-hydroxy-6-(2-acetoxyethoxy)-2H-1-benzopyran-2-one was obtained.

In the same manner as in Example 1, except that an equimolar amount of 3-hexyloxy-4-hydroxy-6-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 10.02(bs, 1H), 6.80–7.20 (m, 3H), 4.91(bs, 1H), 4.07(t, 2H, J=6.0 Hz), 3.90(t, 2H, J=5.0 Hz), 3.75(t, 2H, J=6.0 Hz), 1.30–1.80(m, 8H), 0.87(t, 3H, J=7.0 Hz)

IR(KBr, cm$^{-1}$): 3300, 3005, 1670, 1600, 1230

Elemental analysis for $C_{17}H_{22}O_6$ Calculated (%): C63.34; H6.88; O29.79 Found (%): C63.28; H6.82; O29.90

Example 27

Synthesis of 3-(4-methylpentyloxy)-4-hydroxy-6-(2-hydroxyethoxy)-2H-1-benzopyran-2-one (compound (11))

In the same manner as in Reference Example 1, except that an equimolar amount of 3-(4-methylpentyloxy)-4,6-dihydroxy-2H-1-benzopyran-2-one was used in place of 3-ethoxy-4,5-dihydroxy-2H-1-benzopyran-2-one in Reference Example 1, 3-(4-methylpentyloxy)-4-hydroxy-6-(2-acetoxyethoxy)-2H-1-benzopyran-2-one was obtained.

In the same manner as in Example 1, except that an equimolar amount of 3-(4-methylpentyloxy)-4-hydroxy-6-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 9.98(bs, 1H), 6.80–7.20 (m, 3H), 4.85(bs, 1H), 4.07(t, 2H, J=6.0 Hz), 3.83(t, 2H, J=5.0 Hz), 3.77(t, 2H, J=6.0 Hz), 1.20–1.80(m, 5H), 0.87(d, 6H, J=3.0 Hz)

IR(KBr, cm$^{-1}$): 3300, 3000, 1660, 1600, 1230

Elemental analysis for $C_{17}H_{22}O_6$ Calculated (%): C63.34; H6.88; O29.79 Found (%): C63.45; H6.91; O29.64

Example 28

Synthesis of 3-octyloxy-4-hydroxy-6-(2-hydroxyethoxy)-2H-1-benzopyran-2-one (compound (115))

In the same manner as in Reference Example 1, except that an equimolar amount of 3-octyloxy-4,6-dihydroxy-2H-1-benzopyran-2-one was used in place of 3-ethoxy-4,5-dihydroxy-2H-1-benzopyran-2-one in Reference Example 1, 3-octyloxy-4-hydroxy-6-(2-acetoxyethoxy)-2H-1-benzopyran-2-one was obtained.

In the same manner as in Example 1, except that an equimolar amount of 3-octyloxy-4-hydroxy-6-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 9.96(bs, 1H), 6.80–7.20 (m, 3H), 4.89(bs, 1H), 4.06(t, 2H, J=6.0 Hz), 3.87(t, 2H, J=5.0 Hz), 3.79(t, 2H, J=6.0 Hz), 1.20–1.80(m, 12H), 0.88(t, 3H, J=6.0 Hz)

IR(KBr, cm$^{-1}$): 3300, 3005, 1660, 1610, 1230

Elemental analysis for $C_{19}H_{26}O_6$ Calculated (%): C65.12; H7.48; O27.40 Found (%): C64.99; H7.54; O27.47

Example 29

Synthesis of 3-geranyloxy-4-hydroxy-6-(2-hydroxyethoxy)-2H-1-benzopyran-2-one (compound (125))

In the same manner as in Reference Example 1, except that an equimolar amount of 3-geranyloxy-4,6-dihydroxy-2H-1-benzopyran-2-one was used in place of 3-ethoxy-4,5-dihydroxy-2H-1-benzopyran-2-one in Reference Example 1, 3-geranyloxy-4-hydroxy-6-(2-acetoxyethoxy)-2H-1-benzopyran-2-one was obtained.

In the same manner as in Example 1, except that an equimolar amount of 3-geranyloxy-4-hydroxy-6-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 9.98(bs, 1H), 6.80–7.20 (m, 3H), 5.39(m, 1H), 5.26(m, 1H), 5.10(m, 1H), 4.89(bs, 1H), 4.23(m, 2H), 4.04(t, 2H, J=6.0 Hz), 3.76(t, 2H, J=6.0 Hz), 1.50–2.15(m, 13H)

IR(KBr, cm$^{-1}$): 3300, 3005, 1660, 1610, 1230

Elemental analysis for $C_{21}H_{26}O_6$ Calculated (%): C67.36; H7.00; O25.64 Found (%): C67.42; H6.91; O25.67

Example 30

Synthesis of 3-butoxy-4-hydroxy-6-(3-hydroxypropyloxy)-2H-1-benzopyran-2-one (Compound (129))

In the same manner as in Reference Example 1, except that an equimolar amount of 3-butoxy-4,6-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-butoxy-4-hydroxy-6-(3-acetoxypropoxy)-2H-1-benzopyran-2-one was obtained.

In the same manner as in Example 1, except that an equimolar amount of 3-butoxy-4-hydroxy-6-(3-acetoxypropoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.99(bs, 1H), 6.80–7.20 (m, 3H), 4.89(bs, 1H), 3.90–4.00(m, 4H), 3.71(t, 2H, J=6.0 Hz), 1.30–1.95(m, 6H), 0.87(t, 3H, J=7.0 Hz)

IR(KBr, cm$^{-1}$): 3300, 3005, 1670, 1600, 1230

Elemental analysis for $C_{16}H_{20}O_6$ Calculated (%): C62.32; H6.54; O31.14 Found (%): C62.37; H6.42; O31.21

Example 31

Synthesis of 3-hexyloxy-4-hydroxy-6-(3-hydroxypropyloxy)-2H-1-benzopyran-2-one (compound (130))

In the same manner as in Reference Example 1, except that an equimolar amount of 3-hexyloxy-4,6-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-hexyloxy-4-hydroxy-6-(3-acetoxypropoxy)-2H-1-benzopyran-2-one was obtained.

In the same manner as in Example 1, except that an equimolar amount of 3-hexyloxy-4-hydroxy-6-(3-acetoxypropoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.02(bs, 1H), 6.80–7.20 (m, 3H), 4.87(bs, 1H), 3.90–4.00(m, 4H), 3.70(t, 2H, J=6.0 Hz), 1.20–1.95(m, 10H), 0.86(t, 3H, J=7.0 Hz)

IR(KBr, cm$^{-1}$): 3300, 3005, 1670, 1600, 1230

Elemental analysis for $C_{18}H_{24}O_6$ Calculated (%): C64.27; H7.19; O28.54 Found (%): C64.31; H7.26; O28.43

Example 32

Synthesis of 3-octyloxy-4-hydroxy-6-(3-hydroxypropyloxy)-2H-1-benzopyran-2-one (Compound (132))

In the same manner as in Reference Example 1, except that an equimolar amount of 3-octyloxy-4,6-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-octyloxy-4-hydroxy-6-(3-acetoxypropoxy)-2H-1-benzopyran-2-one was obtained.

In the same manner as in Example 1, except that an equimolar amount of 3-octyloxy-4-hydroxy-6-(3-acetoxypropoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.99(bs, 1H), 6.80–7.20 (m, 3H), 4.89(bs, 1H), 3.90–4.00(m, 4H), 3.71(t, 2H, J=6.0 Hz), 1.20–1.95(m, 14H), 0.89(t, 3H, J=7.0 Hz)

IR(KBr, cm$^{-1}$):3300, 3005, 1670, 1600, 1230

Elemental analysis for $C_{20}H_{28}O_6$ Calculated (%): C65.91; H7.74; O26.34 Found (%): C66.02; H7.69; O26.29

Example 33

Synthesis of 3-ethoxy-4-hydroxy-6-(4-hydroxybutoxy)-2H-1-benzopyran-2-one (compound (137))

In the same manner as in Reference Example 1, except that an equimolar amount of 3-ethoxy-4,6-dihydroxy-2H-1-benzopyran-2-one was used in place of 3-ethoxy-4,5-dihydroxy-2H-1-benzopyran-2-one, and 4-bromobutyl acetate was used in place of 2-bromoethyl acetate in Reference Example 1, 3-ethoxy-4-hydroxy-6-(4-acetoxybutoxy)-2H-1-benzopyran-2-one was obtained.

In the same manner as in Example 1, except that an equimolar amount of 3-ethoxy-4-hydroxy-6-(4-acetoxybutoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.98(bs, 1H), 6.80–7.20 (m, 3H), 4.84(bs, 1H), 4.17(t, 2H, J=5.0 Hz), 3.99(q, 2H, J=6.0 Hz), 3.78(t, 2H, J=5.0 Hz), 1.40–1.75(m, 4H), 1.22(t, 3H, J=7.0 Hz)

IR(KBr, cm$^{-1}$): 3300, 3005, 1670, 1600, 1230

Elemental analysis for $C_{15}H_{18}O_6$ Calculated (%): C61.21; H6.17; O32.62 Found (%): C61.15; H6.28; O32.57

Example 34

Synthesis of 3-butoxy-4-hydroxy-6-(4-hydroxybutoxy)-2H-1-benzopyran-2-one (Compound (138))

In the same manner as in Reference Example 1, except that an equimolar amount of 3-butoxy-4,6-dihydroxy-2H-1-benzopyran-2-one was used in place of 3-ethoxy-4,5-dihydroxy-2H-1-benzopyran-2-one, and 4-bromobutyl acetate was used in place of 2-bromoethyl acetate in Reference Example 1, 3-butoxy-4-hydroxy-6-(4-acetoxybutoxy)-2H-1-benzopyran-2-one was obtained.

In the same manner as in Example 1, except that an equimolar amount of 3-butoxy-4-hydroxy-6-(4-acetoxybutoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 9.97(bs, 1H), 6.80–7.20 (m, 3H), 4.86(bs, 1H), 3.90–4.00(m, 4H), 3.72(t, 2H, J=6.0 Hz), 1.30–1.95(m, 8H), 0.86(t, 3H, J=7.0 Hz)

IR(KBr, cm$^{-1}$): 3300, 3005, 1670, 1600, 1230

Elemental analysis for $C_{17}H_{22}O_6$ Calculated (%): C63.34; H6.88; O29.78 Found (%): C63.23; H6.93; O29.84

Reference Example 4

Synthesis of 3-hexyloxy-4-hydroxy-6-(2,2-dimethyl-1,3-dioxolane-4-methoxy)-2H-1-benzopyran-2-one In the same manner as in Reference Example 2, except that an equimolar amount of 3-hexyloxy-4,6-dihydroxy-2H-1-benzopyran-2-one was used in place of 3-hexyloxy-4,5-dihydroxy-2H-1-benzopyran-2-one in Reference Example 2, the titled compound was obtained.

$^1$H-NMR(CDCl$_3$, δ-TMS) 9.99(bs, 1H), 6.80–7.20(m, 3H), 4.51(t, 2H, J=5.2 Hz), 3.90–4.21(m, 5H), 1.75(m, 2H), 1.48(s, 3H), 1.42(s, 3H), 1.20–1.41(m, 6H), 0.88(t, 3H, J=7.0 Hz)

IR(KBr, cm$^{-1}$): 3300, 3005, 1725, 1600, 1230

Elemental analysis for $C_{21}H_{28}O_7$ Calculated (%): C64.27; H7.19; O28.54 Found (%): C64.34; H7.21; O28.45

Example 35

Synthesis of 3-hexyloxy-4-hydroxy-6-(2,3-dihydroxypropyloxy)-2H-1-benzopyran-2-one (compound (147))

In the same manner as in Example 12, except that an equimolar amount of 3-hexyloxy-4-hydroxy-6-(2,2- dimethyl-1,3-dioxolane-4-methoxy)-2H-1-benzopyran-2-one obtained in Reference Example 4 was used in place of 3-hexyloxy-4-hydroxy-5-(2,2-dimethyl-1,3-dioxolane-4-methoxy)-2H-1-benzopyran-2-one in Example 12, the titled compound was obtained.

$^1$H-NMR(DMSO-d$_6$, δ-TMS): 10.03(bs, 1H), 6.80–7.20 (m, 3H), 4.98(s, 1H), 4.71(s, 1H), 3.81–4.11(m, 5H), 3.45(s, 2H), 1.70(m, 2H), 1.18–1.40(m, 6H), 0.86(t, 3H, J=7.0 Hz)

IR(KBr, cm$^{-1}$): 3420, 3005, 1680, 1610, 1260

Elemental analysis for $C_{18}H_{24}O_7$ Calculated (%): C61.35; H6.86; O31.78 Found (%): C61.40; H6.74; O31.86

Example 36

Synthesis of 3-butoxy-4-hydroxy-6-(2,3-dihydroxypropyloxy)-2H-1-benzopyran-2-one (compound (146))

In the same manner as in Reference Example 2, except that an equimolar amount of 3-butoxy-4,6-dihydroxy-2H-1-benzopyran-2-one was used in place of 3-hexyloxy-4,5-dihydroxy-2H-1-benzopyran-2-one in Reference Example 2, 3-butoxy-4-hydroxy-6-(2,2-dimethyl-1,3-dioxolane-4-ethoxy)-2H-1-benzopyran-2-one was obtained.

In the same manner as in Example 2, except that 3-butoxy-4-hydroxy-6-(2,2-dimethyl-1,3-dioxolane-4-ethoxy)-2H-1-benzopyran-2-one was used in place of 3-butoxy-4-hydroxy-5-(2,2-dimethyl-1,3-dioxolane-4-ethoxy)-2H-1-benzopyran-2-one in Example 2, the titled compound was obtained.

$^1$H-NMR(DMSO-d$_6$, δ-TMS): 9.97(bs, 1H), 6.80–7.20 (m, 3H), 5.01(s, 1H), 4.69(s, 1H), 3.81–4.11(m, 5H), 3.44(s, 2H), 1.18–1.40(m, 4H), 0.86(t, 3H, J=7.0 Hz)

IR(KBr, cm$^{-1}$): 3420, 3005, 1680, 1610, 1260

Elemental analysis for $C_{16}H_{20}O_7$ Calculated (%): C59.25; H6.22; O34.53 Found (%): C59.18; H6.20; O34.62

Reference Example 5

Synthesis of 3-hexyloxy-4-hydroxy-6-ethoxycarbonylmethoxy-2H-1-benzopyran-2-one

In the same manner as in Reference Example 3, except that an equimolar amount of 3-hexyloxy-4,6-dihydroxy-2H-1-benzopyran-2-one was used in place of 3-hexyloxy-4,5-dihydroxy-2H-1-benzopyran-2-one in Reference Example 3 the titled compound was obtained.

$^1$H-NMR(DMSO-d$_6$, δ-TMS): 9.99(bs, 1H), 6.80–7.20 (m, 3H), 4.91(s, 2H), 3.81–4.11(m, 4H), 1.69(m, 2H), 1.20–1.40(m, 9H), 0.88(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.71; H6.60; O30.69

Example 37

Synthesis of 3-hexyloxy-4-hydroxy-6-hydroxycarbonylmethoxy-2H-1-benzopyran-2-one (compound (166))

In the same manner as in Example 14, except that an equimolar amount of 3-hexyloxy-4-hydroxy-6-ethoxycarbonylmethoxy-2H-1-benzopyran-2-one obtained in Reference Example 5 was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.02(bs, 1H), 9.99(bs, 1H), 6.80–7.20(m, 3H), 4.87(s, 2H), 3.89(t, 2H, J=5.0 Hz), 1.69(m, 2H), 1.20–1.40(m, 6H), 0.86(t, 3H, J=7.0 Hz)

IR(KBr, cm$^{-1}$): 3420, 3005, 1750, 1610, 1260

Elemental analysis for $C_{17}H_{20}O_7$ Calculated (%): C60.71; H5.99; O33.30 Found (%): C60.79; H6.10; O33.11

Example 38

Synthesis of 3-ethoxy-4-hydroxy-6-hydroxycarbonylmethoxy-2H-1-benzopyran-2-one (compound (160))

In the same manner as in Reference Example 3, except that an equimolar amount of 3-ethoxy-4,6-dihydroxy-2H-1-benzopyran-2-one was used in place of 3-hexyloxy-4,5-dihydroxy-2H-1-benzopyran-2-one in Reference Example 3, 3-ethoxy-4-hydroxy-6-ethoxycarbonylmethoxy-2H-1-benzopyran-2-one was obtained.

In the same manner as in Example 14, except that an equimolar amount of 3-ethoxy-4-hydroxy-6-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.11(bs, 1H), 10.01(bs, 1H), 6.80–7.20(m, 3H), 4.86(s, 2H), 4.08(q, 2H, J=6.0 Hz), 1.26(t, 3H, J=7.0 Hz)

IR(KBr, cm$^{-1}$): 3420, 3005, 1750, 1610, 1260

Elemental analysis for $C_{13}H_{12}O_7$ Calculated (%): C55.72; H4.32; O39.97 Found (%): C55.76; H4.13; O40.11

Example 39

Synthesis of 3-butoxy-4-hydroxy-6-hydroxycarbonylmethoxy-2H-1-benzopyran-2-one (compound (163))

In the same manner as in Reference Example 3, except that an equimolar amount of 3-butoxy-4,6-dihydroxy-2H-1-benzopyran-2-one was used in place of 3-hexyloxy-4,5-dihydroxy-2H-1-benzopyran-2-one in Reference Example 3, 3-butoxy-4-hydroxy-6-ethoxycarbonylmethoxy-2H-1-benzopyran-2-one was obtained.

In the same manner as in Example 14, except that an equimolar amount of 3-butoxy-4-hydroxy-6-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.08(bs, 1H), 9.98(bs, 1H), 6.80–7.20(m, 3H), 4.89(s, 2H), 3.96(t, 2H, J=6.0 Hz), 1.30–1.95(m, 4H), 0.86(t, 3H, J=7.0 Hz)

IR(KBr, cm$^{-1}$): 3420, 3005, 1750, 1610, 1260

Elemental analysis for $C_{15}H_{16}O_7$ Calculated (%): C58.44; H5.23; O36.33 Found (%): C58.35; H5.25; O36.40

Example 40

Synthesis of 3-octyloxy-4-hydroxy-6-hydroxycarbonylmethoxy-2H-1-benzopyran-2-one (compound (172))

In the same manner as in Reference Example 3, except that an equimolar amount of 3-octyloxy-4,6-dihydroxy-2H-1-benzopyran-2-one was used in place of 3-hexyloxy-4,5-dihydroxy-2H-1-benzopyran-2-one in Reference Example 3, 3-octyloxy-4-hydroxy-6-ethoxycarbonylmethoxy-2H-1-benzopyran-2-one was obtained.

In the same manner as in Example 14, except that an equimolar amount of 3-octyloxy-4-hydroxy-6- ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.10(bs, 1H), 9.98(bs, 1H), 6.80–7.20(m, 3H), 4.87(s, 2H), 3.97(t, 2H, J=6.0 Hz), 1.30–1.95(m, 12H), 0.85(t, 3H, J=7.0 Hz)

IR(KBr, cm$^{-1}$):3420, 3005, 1750, 1610, 1260

Elemental analysis for C$_{19}$H$_{24}$O$_7$ Calculated (%): C62.62; H6.64; O30.73 Found (%): C62.56; H6.80; O30.64

Example 41

Synthesis of 3-geranyloxy-4-hydroxy-6-hydroxycarbonylmethoxy-2H-1-benzopyran-2-one (compound (182))

In the same manner as in Reference Example 3, except that an equimolar amount of 3-geranyloxy-4,6-dihydroxy-2H-1-benzopyran-2-one was used in place of 3-hexyloxy-4,5-dihydroxy-2H-1-benzopyran-2-one in Reference Example 3, 3-geranyloxy-4-hydroxy-6-ethoxycarbonylmethoxy-2H-1-benzopyran-2-one was obtained.

In the same manner as in Example 14, except that an equimolar amount of 3-geranyloxy-4-hydroxy-6-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.16(bs, 1H), 9.96(bs, 1H), 6.80–7.20(m, 3H), 5.39(m, 1H), 5.24(m, 1H), 5.10(m, 1H), 4.87(s, 2H), 4.25(m, 2H), 4.05(t, 2H, J=6.0 Hz), 3.79(t, 2H, J=6.0 Hz), 1.50–2.15(m, 13H)

IR(KBr, cm$^{-1}$): 3420, 3005, 1750, 1610, 1260

Elemental analysis for C$_{21}$H$_{24}$O$_7$ Calculated (%): C64.93; H6.23; O28.84 Found (%): C64.95; H6.13; O28.92

Example 42

Synthesis of 3-butoxy-4-hydroxy-6-(2-hydroxycarbonylethoxy)-2H-1-benzopyran-2-one (compound (186))

In the same manner as in Reference Example 3, except that an equimolar amount of 3-ethoxy-4,6-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-ethoxy-4-hydroxy-6-(2-ethoxycarbonylethoxy-2H-1-benzopyran-2-one was obtained.

In the same manner as in Example 14, except that an equimolar amount of 3-ethoxy-4-hydroxy-6-(2-ethoxycarbonylethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.14(bs, 1H), 9.99(bs, 1H), 6.80–7.20(m, 3H), 4.43(t, 2H, J=5.0 Hz), 3.97(t, 2H, J=6.0 Hz), 3.18(t, 2H, J=5.0 Hz), 1.30–1.95(m, 4H), 0.88(t, 3H, J=7.0 Hz)

IR(KBr, cm$^{-1}$): 3420, 3005, 1750, 1610, 1260

Elemental analysis for C$_{16}$H$_{18}$O$_7$ Calculated (%): C59.62; H5.63; O34.75 Found (%): C59.59; H5.57; O34.84

Example 43

Synthesis of 3-hexyloxy-4-hydroxy-6-(2-hydroxycarbonylethoxy)-2H-1-benzopyran-2-one (compound (187))

In the same manner as in Reference Example 3, except that an equimolar amount of 3-hexyloxy-4,6-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-hexyloxy-4-hydroxy-6-(2-ethoxycarbonylethoxy-2H-1-benzopyran-2-one was obtained.

In the same manner as in Example 14, except that an equimolar amount of 3-hexyloxy-4-hydroxy-6-(2-ethoxycarbonylethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.12(bs, 1H), 9.98(bs, 1H), 6.80–7.20(m, 3H), 4.46(t, 2H, J=5.0 Hz), 3.98(t, 2H, J=6.0 Hz), 3.19(t, 2H, J=5.0 Hz), 1.69(m, 2H), 1.30–1.95(m, 8H), 0.87(t, 3H, J=7.0 Hz)

IR(KBr, cm$^{-1}$): 3420, 3005, 1750, 1610, 1260

Elemental analysis for C$_{18}$H$_{22}$O$_7$ Calculated (%): C61.70; H6.33; O31.97 Found (%): C61.83; H6.21; O31.96

Example 44

Synthesis of 3-octyloxy-4-hydroxy-6-(2-hydroxycarbonylethoxy)-2H-1-benzopyran-2-one (compound (188))

In the same manner as in Reference Example 3, except that an equimolar amount of 3-octyloxy-4,6-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-octyloxy-4-hydroxy-6-(2-ethoxycarbonylethoxy-2H-1-benzopyran-2-one was obtained.

In the same manner as in Example 14, except that an equimolar amount of 3-octyloxy-4-hydroxy-6-(2-ethoxycarbonylethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.12(bs, 1H), 9.96(bs, 1H), 6.80–7.20(m, 3H), 4.40(t, 2H, J=5.0 Hz), 3.98(t, 2H, J=6.0 Hz), 3.21(t, 2H, J=5.0 Hz), 1.68(m, 2H), 1.30–1.95(m, 12H), 0.88(t, 3H, J=7.0 Hz)

IR(KBr, cm$^{-1}$): 3420, 3005, 1750, 1610, 1260

Elemental analysis for C$_{20}$H$_{26}$O$_7$ Calculated (%): C63.48; H6.93; O29.60 Found (%): C63.40; H6.88; O29.72

Example 45

Synthesis of 3-hexyloxy-4-hydroxy-6-(3-hydroxycarbonylpropyloxy)-2H-1-benzopyran-2-one (compound (194))

In the same manner as in Reference Example 3, except that an equimolar amount of 3-hexyloxy-4,6-dihydroxy-2H-1-benzopyran-2-one was used in place of 3-hexyloxy-4,5-dihydroxy-2H-1-benzopyran-2-one, and ethyl 4-bromobutanoate was used in place of ethyl bromoacetate in Reference Example 3, 3-hexyloxy-4-hydroxy-6-(3-ethoxycarbonylpropyloxy)-2H-1-benzopyran-2-one was obtained.

In the same manner as in Example 14, except that an equimolar amount of 3-hexyloxy-4-hydroxy-6-(3-ethoxycarbonylpropyloxy-2H-1-benzopyran-2-one was used in place of 3-hexyloxy-4-hydroxy-5-ethoxycarbonylmethoxy-2H-1-benzopyran-2-one in Example 14, the titled compound was obtained.

¹H-NMR(DMSO-d$_6$, δ-TMS): 11.12(bs, 1H), 9.98(bs, 1H), 6.80–7.20(m, 3H), 4.41(t, 2H, J=5.0 Hz), 3.99(t, 2H, J=6.0 Hz), 2.24(t, 2H, J=5.0 Hz), 1.30–2.00(m, 10H), 0.88(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.59; H6.75; O30.66

Example 46

Synthesis of 3-hexyloxy-4-hydroxy-6-(4-hydroxycarbonylbutoxy)-2H-1-benzopyran-2-one (compound (200))

In the same manner as in Reference Example 3, except that an equimolar amount of 3-hexyloxy-4,6-dihydroxy-2H-1-benzopyran-2-one was used in place of 3-hexyloxy-4,5-dihydroxy-2H-1-benzopyran-2-one, and ethyl 5-bromopentanoate was used in place of ethyl bromoacetate in Reference Example, 3-hexyloxy-4-hydroxy-6-(5-ethoxycarbonylbutoxy-2H-1-benzopyran-2-one was obtained.

In the same manner as in Example 14, except that an equimolar amount of 3-hexyloxy-4-hydroxy-6-(5-ethoxycarbonylbutoxy-2H-1-benzopyran-2-one was used in place of 3-hexyloxy-4-hydroxy-5-ethoxycarbonylmethoxy-2H-1-benzopyran-2-one in Example 14, the titled compound was obtained.

¹H-NMR(DMSO-d$_6$, δ-TMS): 11.15(bs, 1H), 10.01(bs, 1H), 6.80–7.20(m, 3H), 4.40(t, 2H, J=5.0 Hz), 3.98(t, 2H, J=6.0 Hz), 2.23(t, 2H, J=5.0 Hz), 1.30–2.00(m, 12H), 0.88(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.51; H6.81; O29.68

Reference Example 6

Synthesis of 3-butoxy-4-hydroxy-7-(2-hydroxyethoxy)-2H-1-benzopyran-2-one (compound (207))

In the same manner as in Reference Example 1, except that an equimolar amount of 3-butoxy-4,7-dihydroxy-2H-1-benzopyran-2-one was used in place of 3-ethoxy-4,5-dihydroxy-2H-1-benzopyran-2-one in Reference Example 1, 3-butoxy-4-hydroxy-7-(2-acetoxyethoxy)-2H-1-benzopyran-2-one was obtained.

In the same manner as in Example 1, except that an equimolar amount of 3-butoxy-4-hydroxy-7-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

¹H-NMR(DMSO-d$_6$, δ-TMS): 11.45(bs, 1H), 7.72(d, 1H, J=7.2 Hz), 6.92(s, 2H), 4.86(bs, 1H), 4.07(t, 2H, J=6.8 Hz), 3.88(t, 2H, J=5.2 Hz), 3.78(t, 2H, J=5.2 Hz), 1.25–1.68(m, 4H), 0.86(t, 3H, J=7.2 Hz)

IR(KBr, cm$^{-1}$): 3300, 3005, 1670, 1600, 1230

Elemental analysis for $C_{15}H_{18}O_6$ Calculated (%): C61.21; H6.17; O32.62 Found (%): C61.38; H6.18; O32.44

Reference Example 7

Synthesis of 3-hexyloxy-4-hydroxy-7-(2-hydroxyethoxy)-2H-1-benzopyran-2-one (compound (210))

In the same manner as in Reference Example 1, except that an equimolar amount of 3-hexyloxy-4,7-dihydroxy-2H-1-benzopyran-2-one was used in place of 3-ethoxy-4,5-dihydroxy-2H-1-benzopyran-2-one in Reference Example 1, 3-hexyloxy-4-hydroxy-7-(2-acetoxyethoxy)-2H-1-benzopyran-2-one was obtained.

In the same manner as in Example 1, except that an equimolar amount of 3-butoxy-4-hydroxy-7-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

¹H-NMR(DMSO-d$_6$, δ-TMS): 11.49(bs, 1H), 7.71(d, 1H, J=7.2 Hz), 6.94(s, 2H), 4.86(bs, 1H), 4.07(t, 2H, J=6.8 Hz), 3.86(t, 2H, J=5.2 Hz), 3.74(t, 2H, J=5.2 Hz), 1.20–1.40(m, 8H), 0.86(t, 3H, J=7.2 Hz)

IR(KBr, cm$^{-1}$): 3300, 3005, 1670, 1600, 1230

Elemental analysis for $C_{17}H_{22}O_6$ Calculated (%): C63.34; H6.88; O29.79 Found (%): C63.39; H6.91; O29.70

Reference Example 8

Synthesis of 3-octyloxy-4-hydroxy-7-(2-hydroxyethoxy)-2H-1-benzopyran-2-one (compound (216))

In the same manner as in Reference Example 1, except that an equimolar amount of 3-octyloxy-4,7-dihydroxy-2H-1-benzopyran-2-one was used in place of 3-ethoxy-4,5-dihydroxy-2H-1-benzopyran-2-one in Reference Example 1, 3-octyloxy-4-hydroxy-7-(2-acetoxyethoxy)-2H-1-benzopyran-2-one was obtained.

In the same manner as in Example 1, except that an equimolar amount of 3-octyloxy-4-hydroxy-7-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

¹H-NMR(DMSO-d$_6$, δ-TMS): 11.50(bs, 1H), 7.70(d, 1H, J=7.2 Hz), 6.95(s, 2H), 4.91(bs, 1H), 4.07(t, 2H, J=6.8 Hz), 3.88(t, 2H, J=5.2 Hz), 3.73(t, 2H, J=5.2 Hz), 1.68(m, 2H), 1.25–1.40(m, 10H), 0.86(t, 3H, J=7.2 Hz)

IR(KBr, cm$^{-1}$): 3300, 3005, 1660, 1610, 1230

Elemental analysis for $C_{19}H_{26}O_6$ Calculated (%): C65.12; H7.48; O27.40 Found (%): C65.48; H7.18; O27.34

Reference Example 9

Synthesis of 3-geranyloxy-4-hydroxy-7-(2-hydroxyethoxy)-2H-1-benzopyran-2-one (compound (226))

In the same manner as in Reference Example 1, except that an equimolar amount of 3-geranyloxy-4,7-dihydroxy-2H-1-benzopyran-2-one was used in place of 3-ethoxy-4,5-dihydroxy-2H-1-benzopyran-2-one in Reference Example 1, 3-geranyloxy-4-hydroxy-7-(2-acetoxyethoxy)-2H-1-benzopyran-2-one was obtained.

In the same manner as in Example 1, except that an equimolar amount of 3-geranyloxy-4-hydroxy-7-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

¹H-NMR(DMSO-d$_6$, δ-TMS): 9.30(bs, 1H), 7.74(d, 1H, J=7.2 Hz), 6.93(s, 2H), 5.40(m, 1H), 5.25(m, 1H), 5.10(m, 1H), 4.88(bs, 1H), 4.21(m, 2H), 4.05(t, 2H, J=6.0 Hz), 3.77(t, 2H, J=6.0 Hz), 1.50–2.15(m, 13H)

IR(KBr, cm$^{-1}$): 3300, 3005, 1660, 1610, 1230

Elemental analysis for $C_{21}H_{26}O_6$ Calculated (%): C67.36; H7.00; O25.64 Found (%): C67.40; H7.10; O25.50

Reference Example 10

Synthesis of 3-octyloxy-4-hydroxy-7-(2,3-dihydroxypropyloxy)-2H-1-benzopyran-2-one (compound (249))

In the same manner as in Reference Example 2, except that an equimolar amount of 3-octyloxy-4,7-dihydroxy-2H-1-benzopyran-2-one was used in place of 3-hexyloxy-4,5-dihydroxy-2H-1-benzopyran-2-one in Reference Example 2, 3-octyloxy-4-hydroxy-7-(2,2-dimethyl-1,3-dioxolane-4-methoxy)-2H-1-benzopyran-2-one was obtained.

In the same manner as in Example 12, except that an equimolar amount of 3-octyloxy-4-hydroxy-7-(2,2-dimethyl-1,3-dioxolane-4-methoxy)-2H-1-benzopyran-2-one was used in place of 3-hexyloxy-4-hydroxy-5-(2,2-dimethyl-1,3-dioxolane-4-methoxy)-2H-l-benzopyran-2-one in Example 12, the titled compound was obtained.

$^1$H-NMR(DMSO-$d_6$, δ-TMS): 11.51(bs, 1H), 7.70(d, 1H, J=8.2 Hz), 6.95(m, 2H), 5.00(s, 1H), 4.70(s, 1H), 3.81–4.11 (m, 5H), 3.45(s, 2H), 1.18–1.40(m, 10H), 0.86(t, 3H, J=7.2 Hz)

IR(KBr, cm$^{-1}$): 3420, 3005, 1680, 1610, 1260

Elemental analysis for $C_{20}H_{28}O_7$ Calculated (%): C63.14; H7.42; O29.44 Found (%): C63.38; H7.58; O29.04

Reference Example 11

Synthesis of 3-hexyloxy-4-hydroxy-7-ethoxycarbonylmethoxy-2H-1-benzopyran-2-one

In the same manner as in Reference Example 3, except that 3-hexyloxy-4,7-dihydroxy-2H-1-benzopyran-2-one was used in place of 3-hexyloxy-4,5-dihydroxy-2H-1-benzopyran-2-one in Reference Example 3, the titled compound was obtained.

$^1$H-NMR(DMSO-$d_6$, δ-TMS): 11.50(bs, 1H), 7.72(t, 1H, J=7.0 Hz), 6.95(s, 2H), 4.91(s, 2H), 3.81–4.11(m, 4H), 1.69(m, 2H), 1.20–1.40(m, 9H), 0.88(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.68; H6.58; O30.64

Example 47

Synthesis of 3-hexyloxy-4-hydroxy-7-hydroxycarbonylmethoxy-2H-1-benzopyran-2-one (compound (267))

In the same manner as in Example 14, except that 3-hexyloxy-4-hydroxy-7-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.51(bs, 1H), 11.10(bs, 1H), 7.73(t, 1H, J=7.0 Hz), 6.94(s, 2H), 4.88(s, 2H), 3.89(t, 2H, J=5.0 Hz), 1.69(m, 2H), 1.20–1.40(m, 6H), 0.86(t, 3H, J=7.0 Hz)

IR(KBr, cm$^{-1}$): 3420, 3005, 1750, 1610, 1260

Elemental analysis for $C_{17}H_{20}O_7$ Calculated (%): C60.71; H5.99; O33.30 Found (%): C60.68; H6.07; O33.25

Example 48

Synthesis of 3-ethoxy-4-hydroxy-7-hydroxycarbonylmethoxy-2H-1-benzopyran-2-one (compound (261))

In the same manner as in Reference Example 3, except that an equimolar amount of 3-ethoxy-4,7-dihydroxy-2H-1-benzopyran-2-one was used in place of 3-hexyloxy-4,5-dihydroxy-2H-1-benzopyran-2-one in Reference Example 3, 3-ethoxy-4-hydroxy-7-ethoxycarbonylmethoxy-2H-1-benzopyran-2-one was obtained.

In the same manner as in Example 14, except that an equimolar amount of 3-ethoxy-4-hydroxy-7-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.51(bs, 1H), 11.14(bs, 1H), 7.73(t, 1H, J=7.0 Hz), 6.95(s, 2H), 4.86(s, 2H), 4.08(q, 2H, J=6.0 Hz), 1.26(t, 3H, J=7.0 Hz)

IR(KBr, cm$^{-1}$): 3420, 3005, 1750, 1610, 1260

Elemental analysis for $C_{13}H_{12}O_7$ Calculated (%): C55.72; H4.32; O39.97 Found (%): C55.68; H4.23; O40.09

Example 49

Synthesis of 3-butoxy-4-hydroxy-7-hydroxycarbonylmethoxy-2H-1-benzopyran-2-one (compound (264))

In the same manner as in Reference Example 3, except that an equimolar amount of 3-butoxy-4,7-dihydroxy-2H-1-benzopyran-2-one was used in place of 3-hexyloxy-4,5-dihydroxy-2H-1-benzopyran-2-one in Reference Example 3, 3-butoxy-4-hydroxy-7-ethoxycarbonylmethoxy-2H-1-benzopyran-2-one was obtained.

In the same manner as in Example 14, except that an equimolar amount of 3-butoxy-4-hydroxy-7-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.49(bs, 1H), 11.11(bs, 1H), 7.72(t, 1H, J=7.0 Hz), 6.94(s, 2H), 4.89(s, 2H), 3.96(t, 2H, J=6.0 Hz), 1.30–1.95(m, 4H), 0.88(t, 3H, J=7.0 Hz)

IR(KBr, cm$^{-1}$): 3420, 3005, 1750, 1610, 1260

Elemental analysis for $C_{15}H_{16}O_7$ Calculated (%): C58.44; H5.23; O36.33 Found (%): C58.51; H5.19; O36.30

Example 50

Synthesis of 3-octyloxy-4-hydroxy-7-hydroxycarbonylmethoxy-2H-1-benzopyran-2-one (compound (273))

In the same manner as in Reference Example 3, except that an equimolar amount of 3-octyloxy-4,7-dihydroxy-2H-1-benzopyran-2-one was used in place of 3-hexyloxy-4,5-dihydroxy-2H-1-benzopyran-2-one in Reference Example 3, 3-octyloxy-4-hydroxy-7-ethoxycarbonylmethoxy-2H-1-benzopyran-2-one was obtained.

In the same manner as in Example 14, except that an equimolar amount of 3-octyloxy-4-hydroxy-7-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.54(bs, 1H), 11.14(bs, 1H), 7.71(t, 1H, J=7.0 Hz), 6.94(s, 2H), 4.87(s, 2H), 3.98(t, 2H, J=6.0 Hz), 1.30–1.95(m, 12H), 0.86(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.60; H6.73; O30.67

Example 51

Synthesis of 3-geranyloxy-4-hydroxy-7-hydroxycarbonylmethoxy-2H-1-benzopyran-2-one (compound (283))

In the same manner as in Reference Example 3, except that an equimolar amount of 3-geranyloxy-4,7-dihydroxy-2H-1-benzopyran-2-one was used in place of 3-hexyloxy-4,5-dihydroxy-2H-1-benzopyran-2-one in Reference Example 3, 3-geranyloxy-4-hydroxy-7-ethoxycarbonylmethoxy-2H-1-benzopyran-2-one was obtained.

In the same manner as in Example 14, except that an equimolar amount of 3-geranyloxy-4-hydroxy-7-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.51(bs, 1H), 11.10(bs, 1H), 7.73(t, 1H, J=7.0 Hz), 6.95(s, 2H), 5.39(m, 1H), 5.24(m, 1H), 5.10(m, 1H), 4.87(s, 2H), 4.25(m, 2H), 4.05(t, 2H, J=6.0 Hz), 3.79(t, 2H, J=6.0 Hz), 1.50–2.15(m, 13H)

IR(KBr, cm$^{-1}$): 3420, 3005, 1750, 1610, 1260

Elemental analysis for $C_{21}H_{24}O_7$ Calculated (%): C64.93; H6.23; O28.84 Found (%): C65.01; H6.11; O28.88

Example 52

Synthesis of 3-butoxy-4-hydroxy-7-(2-hydroxycarbonylethoxy)-2H-1-benzopyran-2-one (compound (287))

In the same manner as in Reference Example 3, except that an equimolar amount of 3-butoxy-4,7-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-butoxy-4-hydroxy-7-(2-ethoxycarbonylethoxy)-2H-1-benzopyran-2-one was obtained.

In the same manner as in Example 14, except that an equimolar amount of 3-butoxy-4-hydroxy-7-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.54(bs, 1H), 11.09(bs, 1H), 7.72(t, 1H, J=7.0 Hz), 6.94(s, 2H), 4.42(t, 2H, J=5.0 Hz), 3.97(t, 2H, J=6.0 Hz), 3.17(t, 2H, J=5.0 Hz), 1.30–1.95 (m, 4H), 0.88(t, 3H, J=7.0 Hz)

IR(KBr, cm$^{-1}$): 3420, 3005, 1750, 1610, 1260

Elemental analysis for $C_{16}H_{18}O_7$ Calculated (%): C59.62; H5.63; O34.75 Found (%): C59.67; H5.51; O34.82

Example 53

Synthesis of 3-hexyloxy-4-hydroxy-7-(2-hydroxycarbonylethoxy)-2H-1-benzopyran-2-one (compound (288))

In the same manner as in Reference Example 3, except that an equimolar amount of 3-hexyloxy-4,7-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-hexyloxy-4-hydroxy-7-(2-ethoxycarbonylethoxy)-2H-1-benzopyran-2-one was obtained.

In the same manner as in Example 14, except that an equimolar amount of 3-hexyloxy-4-hydroxy-7-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.51(bs, 1H), 11.12(bs, 1H), 7.73(t, 1H, J=7.0 Hz), 6.94(s, 2H), 4.46(t, 2H, J=5.0 Hz), 3.98(t, 2H, J=6.0 Hz), 3.18(t, 2H, J=5.0 Hz), 1.69(m, 2H), 1.30–1.95(m, 8H), 0.88(t, 3H, J=7.0 Hz)

IR(KBr, cm$^{-1}$): 3420, 3005, 1750, 1610, 1260

Elemental analysis for $C_{18}H_{22}O_7$ Calculated (%): C61.70; H6.33; O31.97 Found (%): C61.65; H6.28; O32.07

Example 54

Synthesis of 3-octyloxy-4-hydroxy-7-(2-hydroxycarbonylethoxy)-2H-1-benzopyran-2-one (compound (289))

In the same manner as in Reference Example 3, except that an equimolar amount of 3-octyloxy-4,7-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-octyloxy-4-hydroxy-7-(2-ethoxycarbonylethoxy)-2H-1-benzopyran-2-one was obtained.

In the same manner as in Example 14, except that an equimolar amount of 3-octyloxy-4-hydroxy-7-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.49(bs, 1H), 11.10(bs, 1H), 7.73(t, 1H, J=7.0 Hz), 6.94(s, 2H), 4.40(t, 2H, J=5.0 Hz), 3.98(t, 2H, J=6.0 Hz), 3.21(t, 2H, J=5.0 Hz), 1.68(m, 2H), 1.30–1.95(m, 12H), 0.88(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.51; H6.97; O29.52

Example 55

Synthesis of 3-hexyloxy-4-hydroxy-7-(3-hydroxycarbonylpropyloxy)-2H-1-benzopyran-2-one (compound 295))

In the same manner as in Reference Example 3, except that an equimolar amount of 3-hexyloxy-4,7-dihydroxy-2H-1-benzopyran-2-one was used in place of 3-hexyloxy-4,5-dihydroxy-2H-1-benzopyran-2-one, and ethyl 3-bromobutanoate was used in place of ethyl bromoacetate in Reference Example 3, 3-hexyloxy-4-hydroxy-7-(2-ethoxycarbonylpropyloxy)-2H-1-benzopyran-2-one was obtained.

In the same manner as in Example 14, except that an equimolar amount of 3-hexyloxy-4-hydroxy-7-(2-ethoxycarbonylpropyloxy)-2H-l-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.54(bs, 1H), 11.12(bs, 1H), 7.73(t, 1H, J=7.0 Hz), 6.92(s, 2H), 4.41(t, 2H, J=5.0 Hz), 3.99(t, 2H, J=6.0 Hz), 2.24(t, 2H, J=5.0 Hz), 1.30–2.00 (m, 10H), 0.89(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.52; H6.79; O30.69

Example 56

Synthesis of 3-hexyloxy-4-hydroxy-7-(4-hydroxycarbonylbutoxy)-2H-1-benzopyran-2-one (compound (301))

In the same manner as in Reference Example 3, except that an equimolar amount of 3-hexyloxy-4,7-dihydroxy-2H-1-benzopyran-2-one was used in place of 3-hexyloxy-4,5-dihydroxy-2H-1-benzopyran-2-one, and ethyl 5-bromopentanoate was used in place of ethyl bromoacetate in Reference Example 3, 3-hexyloxy-4-hydroxy-7-(2-ethoxycarbonylbutoxy)-2H-1-benzopyran-2-one was obtained.

In the same manner as in Example 14, except that an equimolar amount of 3-hexyloxy-4-hydroxy-7-(2-ethoxycarbonylbutoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.53(bs, 1H), 11.12(bs, 1H), 7.71(t, 1H, J=7.0 Hz), 6.94(s, 2H), 4.40(t, 2H, J=5.0 Hz), 3.98(t, 2H, J=6.0 Hz), 2.23(t, 2H, J=5.0 Hz), 1.30–2.00 (m, 12H), 0.88(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.56; H6.82; O29.62

Example 57

Synthesis of 3-ethoxy-4-hydroxy-8-(2-hydroxyethoxy)-2H-1-benzopyran-2-one (compound (305))

In the same manner as in Reference Example 1, except that an equimolar amount of 3-ethoxy-4,8-dihydroxy-2H-1-benzopyran-2-one was used in place of 3-ethoxy-4,5-dihydroxy-2H-1-benzopyran-2-one in Reference Example 1, 3-ethoxy-4-hydroxy-8-(2-acetoxyethoxy)-2H-1-benzopyran-2-one was obtained.

In the same manner as in Example 1, except that an equimolar amount of 3-ethoxy-4-hydroxy-8-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 10.39(bs, 1H), 6.70–7.60 (m, 3H), 4.88(bs, 1H), 4.16(t, 2H, J=5.0 Hz), 4.08(q, 2H, J=6.0 Hz), 3.77(t, 2H, J=5.0 Hz), 1.22(t, 3H, J=7.0 Hz)

IR(KBr, cm$^{-1}$): 3300, 3005, 1670, 1600, 1230

Elemental analysis for $C_{13}H_{14}O_6$ Calculated (%): C58.64; H5.30; O36.06 Found (%): C58.72; H5.19; O36.09

Example 58

Synthesis of 3-butoxy-4-hydroxy-8-(2-hydroxyethoxy)-2H-1-benzopyran-2-one (compound (308))

In the same manner as in Reference Example 1, except that an equimolar amount of 3-butoxy-4,8-dihydroxy-2H-1-benzopyran-2-one was used in place of 3-ethoxy-4,5-dihydroxy-2H-1-benzopyran-2-one in Reference Example 1, 3-butoxy-4-hydroxy-8-(2-acetoxyethoxy)-2H-1-benzopyran-2-one was obtained.

In the same manner as in Example 1, except that an equimolar amount of 3-butoxy-4-hydroxy-8-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 10.41(bs, 1H), 6.70–7.60 (m, 3H), 4.82(bs, 1H), 4.09(t, 2H, J=6.0 Hz), 3.82(t, 2H, J=5.0 Hz), 3.75(t, 2H, J=6.0 Hz), 1.30–1.80(m, 4H), 0.88(t, 3H, J=7.0 Hz)

IR(KBr, cm$^{-1}$): 3300, 3005, 1670, 1600, 1230

Elemental analysis for $C_{15}H_{18}O_6$ Calculated (%): C61.21; H6.17; O32.62 Found (%): C61.26; H6.09; O32.65

Example 59

Synthesis of 3-hexyloxy-4-hydroxy-8-(2-hydroxyethoxy)-2H-1-benzopyran-2-one (compound (311))

In the same manner as in Reference Example 1, except that an equimolar amount of 3-hexyloxy-4,8-dihydroxy-2H-1-benzopyran-2-one was used in place of 3-ethoxy-4,5-dihydroxy-2H-1-benzopyran-2-one in Reference Example 1, 3-hexyloxy-4-hydroxy-8-(2-acetoxyethoxy)-2H-1-benzopyran-2-one was obtained.

In the same manner as in Example 1, except that an equimolar amount of 3-hexyloxy-4-hydroxy-8-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 10.43(bs, 1H), 6.70–7.60 (m, 3H), 4.91(bs, 1H), 4.03(t, 2H, J=6.0 Hz), 3.90(t, 2H, J=5.0 Hz), 3.76(t, 2H, J=6.0 Hz), 1.30–1.80(m, 8H), 0.87(t, 3H, J=7.0 Hz)

IR(KBr, cm$^{-1}$): 3300, 3005, 1670, 1600, 1230

Elemental analysis for $C_{17}H_{22}O_6$ Calculated (%): C63.34; H6.88; O29.79 Found (%): C63.39; H6.94; O29.67

Example 60

Synthesis of 3-(4-methylpentyloxy)-4-hydroxy-8-(2-hydroxyethoxy)-2H-1-benzopyran-2-one (compound (315))

In the same manner as in Reference Example 1, except that an equimolar amount of 3-(4-methylpentyloxy)-4,8-dihydroxy-2H-1-benzopyran-2-one was used in place of 3-ethoxy-4,5-dihydroxy-2H-1-benzopyran-2-one in Reference Example 1, 3-(4-methylpentyloxy)-4-hydroxy-8-(2-acetoxyethoxy)-2H-1-benzopyran-2-one was obtained.

In the same manner as in Example 1, except that an equimolar amount of 3-(4-methylpentyloxy)-4-hydroxy-8-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-$d_6$, δ-TMS): 10.35(bs, 1H), 6.70–7.60 (m, 3H), 4.83(bs, 1H), 4.06(t, 2H, J=6.0 Hz), 3.84(t, 2H, J=5.0 Hz), 3.77(t, 2H, J=6.0 Hz), 1.20–1.80(m, 5H), 0.88(d, 6H, J=3.0 Hz)

IR(KBr, cm$^{-1}$): 3300, 3000, 1660, 1600, 1230

Elemental analysis for $C_{17}H_{22}O_6$ Calculated (%): C63.34; H6.88; O29.79 Found (%): C63.27; H6.96; O29.77

Example 61

Synthesis of 3-octyloxy-4-hydroxy-8-(2-hydroxyethoxy)-2H-1-benzopyran-2-one (compound (317))

In the same manner as in Reference Example 1, except that an equimolar amount of 3-octyloxy-4,8-dihydroxy-2H-

1-benzopyran-2-one was used in place of 3-ethoxy-4,5-dihydroxy-2H-1-benzopyran-2-one in Reference Example 1, 3-octyloxy-4-hydroxy-8-(2-acetoxyethoxy)-2H-1-benzopyran-2-one was obtained.

In the same manner as in Example 1, except that an equimolar amount of 3-octyloxy-4-hydroxy-8-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.43(bs, 1H), 6.70–7.60 (m, 3H), 4.87(bs, 1H), 4.05(t, 2H, J=6.0 Hz), 3.89(t, 2H, J=5.0 Hz), 3.79(t, 2H, J=6.0 Hz), 1.20–1.80(m, 12H), 0.87(t, 3H, J=6.0 Hz)

IR(KBr, cm$^{-1}$): 3300, 3005, 1660, 1610, 1230

Elemental analysis for C$_{19}$H$_{26}$O$_6$ Calculated (%): C65.12; H7.48; O27.40 Found (%): C65.03; H7.51; O27.46

Example 62

Synthesis of 3-geranyloxy-4-hydroxy-8-(2-hydroxyethoxy)-2H-1-benzopyran-2-one (compound (327))

In the same manner as in Reference Example 1, except that an equimolar amount of 3-geranyloxy-4,8-dihydroxy-2H-1-benzopyran-2-one was used in place of 3-ethoxy-4,5-dihydroxy-2H-1-benzopyran-2-one in Reference Example 1, 3-geranyloxy-4-hydroxy-8-(2-acetoxyethoxy)-2H-1-benzopyran-2-one was obtained.

In the same manner as in Example 1, except that an equimolar amount of 3-geranyloxy-4-hydroxy-8-(2-acetoxyethoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.40(bs, 1H), 6.70–7.60 (m, 3H), 5.36(m, 1H), 5.27(m, 1H), 5.09(m, 1H), 4.86(bs, 1H), 4.23(m, 2H), 4.04(t, 2H, J=6.0 Hz), 3.76(t, 2H, J=6.0 Hz), 1.50–2.15(m, 13H)

IR(KBr, cm$^{-1}$): 3300, 3005, 1660, 1610, 1230

Elemental analysis for C$_{21}$H$_{26}$O$_6$ Calculated (%): C67.36; H7.00; O25.64 Found (%): C67.30; H7.11; O25.59

Example 63

Synthesis of 3-butoxy-4-hydroxy-8-(3-hydroxypropyloxy)-2H-1-benzopyran-2-one (compound (331))

In the same manner as in Reference Example 1, except that an equimolar amount of 3-butoxy-4,8-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-ethoxy-4-hydroxy-8-(3-acetoxypropyloxy)-2H-1-benzopyran-2-one was obtained.

In the same manner as in Example 1, except that an equimolar amount of 3-ethoxy-4-hydroxy-8-(3-acetoxypropyloxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.39(bs, 1H), 6.70–7.60 (m, 3H), 4.88(bs, 1H), 3.90–4.00(m, 4H), 3.72(t, 2H, J=6.0 Hz), 1.30–1.95(m, 6H), 0.89(t, 3H, J=7.0 Hz)

IR(KBr, cm$^{-1}$): 3300, 3005, 1670, 1600, 1230

Elemental analysis for C$_{16}$H$_{20}$O$_6$ Calculated (%): C62.32; H6.54; O31.14 Found (%): C62.40; H6.57; O31.03

Example 64

Synthesis of 3-hexyloxyoxy-4-hydroxy-8-(3-hydroxypropyloxy)-2H-1-benzopyran-2-one (compound (332))

In the same manner as in Reference Example 1, except that an equimolar amount of 3-hexyloxy-4,8-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-hexyloxy-4-hydroxy-8-(3-acetoxypropyloxy)-2H-1-benzopyran-2-one was obtained.

In the same manner as in Example 1, except that an equimolar amount of 3-hexyloxy-4-hydroxy-8-(3-acetoxypropyloxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.43(bs, 1H), 6.70–7.60 (m, 3H), 4.87(bs, 1H), 3.90–4.00(m, 4H), 3.72(t, 2H, J=6.0 Hz), 1.20–1.95(m, 10H), 0.87(t, 3H, J=7.0 Hz)

IR(KBr, cm$^{-1}$): 3300, 3005, 1670, 1600, 1230

Elemental analysis for C$_{18}$H$_{24}$O$_6$ Calculated (%): C64.27; H7.19; O28.54 Found (%): C64.23; H7.14; O28.63

Example 65

Synthesis of 3-octyloxy-4-hydroxy-8-(3-hydroxypropyloxy)-2H-1-benzopyran-2-one (compound (334))

In the same manner as in Reference Example 1, except that an equimolar amount of 3-octyloxy-4,8-dihydroxy-2H-1-benzopyran-2-one was used in place of 3-ethoxy-4,5-dihydroxy-2H-1-benzopyran-2-one, and 3-bromopropyl acetate was used in place of 2-bromoethyl acetate in Reference Example 1, 3-octyloxy-4-hydroxy-8-(3-acetoxypropyloxy)-2H-1-benzopyran-2-one was obtained.

In the same manner as in Example 1, except that an equimolar amount of 3-octyloxy-4-hydroxy-8-(3-acetoxypropyloxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.37(bs, 1H), 6.70–7.60 (m, 3H), 4.89(bs, 1H), 3.90–4.00(m, 4H), 3.70(t, 2H, J=6.0 Hz), 1.20–1.95(m, 14H), 0.86(t, 3H, J=7.0 Hz)

IR(KBr, cm$^{-1}$): 3300, 3005, 1670, 1600, 1230

Elemental analysis for C$_{20}$H$_{28}$O$_6$ Calculated (%): C65.91; H7.74; O26.34 Found (%): C65.96; H7.79; O26.25

Example 66

Synthesis of 3-ethoxy-4-hydroxy-8-(4-hydroxybutoxy)-2H-1-benzopyran-2-one (compound (339))

In the same manner as in Reference Example 1, except that an equimolar amount of 3-ethoxy-4,8-dihydroxy-2H-1-benzopyran-2-one was used in place of 3-ethoxy-4,5-dihydroxy-2H-1-benzopyran-2-one, and 4-bromobutyl acetate was used in place of 2-bromoethyl acetate in Reference Example 1, 3-ethoxy-4-hydroxy-8-(4-acetoxybutoxy)-2H-1-benzopyran-2-one was obtained.

In the same manner as in Example 1, except that an equimolar amount of 3-ethoxy-4-hydroxy-8-(4-acetoxybutoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.43(bs, 1H), 6.70–7.60 (m, 3H), 4.81(bs, 1H), 4.19(t, 2H, J=5.0 Hz), 3.95(q, 2H, J=6.0 Hz), 3.78(t, 2H, J=5.0 Hz), 1.40–1.75(m, 4H), 1.22(t, 3H, J=7.0 Hz)

IR(KBr, cm$^{-1}$): 3300, 3005, 1670, 1600, 1230

Elemental analysis for $C_{15}H_{18}O_6$ Calculated (%): C61.21; H6.17; O32.62 Found (%): C61.32; H6.13; O32.55

Example 67

Synthesis of 3-butoxy-4-hydroxy-8-(4-hydroxybutoxy)-2H-1-benzopyran-2-one (compound (340))

In the same manner as in Reference Example 1, except that an equimolar amount of 3-butoxy-4,8-dihydroxy-2H-1-benzopyran-2-one was used in place of 3-ethoxy-4,5-dihydroxy-2H-1-benzopyran-2-one, and 4-bromobutyl acetate was used in place of 2-bromoethyl acetate in Reference Example 1, 3-butoxy-4-hydroxy-8-(4-acetoxybutoxy)-2H-1-benzopyran-2-one was obtained.

In the same manner as in Example 1, except that an equimolar amount of 3-butoxy-4-hydroxy-8-(4-acetoxybutoxy)-2H-1-benzopyran-2-one was used in place of 3-ethoxy-4-hydroxy-5-(2-acetoxyethoxy)-2H-1-benzopyran-2-one in Example 1, the titled compound was obtained.

$^1$H-NMR(DMSO-d$_6$, δ-TMS): 10.32(bs, 1H), 6.70–7.60 (m, 3H), 4.86(bs, 1H), 3.90–4.00(m, 4H), 3.74(t, 2H, J=6.0 Hz), 1.30–1.95(m, 8H), 0.88(t, 3H, J=7.0 Hz)

IR(KBr, cm$^{-1}$): 3300, 3005, 1670, 1600, 1230

Elemental analysis for $C_{17}H_{22}O_6$ Calculated (%): C63.34; H6.88; O29.78 Found (%): C63.28; H6.97; O29.75

Reference Example 12

Synthesis of 3-hexyloxy-4-hydroxy-8-(2,2-dimethyl-1,3-dioxolane-4-methoxy)-2H-1-benzopyran-2-one In the same manner as in Reference Example 2, except that 3-hexyloxy-4,8-dihydroxy-2H-1-benzopyran-2-one was used in place of 3-hexyloxy-4,5-dihydroxy-2H-1-benzopyran-2-one in Reference Example 2, the titled compound was obtained.

$^1$H-NMR(CDCl$_3$, δ-TMS) 10.45(bs, 1H), 6.70–7.50(m, 3H), 4.50(t, 2H, J=5.2 Hz), 3.90–4.21(m, 5H), 1.72(m, 2H), 1.48(s, 3H), 1.42(s, 3H), 1.20–1.41(m, 6H), 0.86(t, 3H, J=7.0 Hz)

IR(KBr, cm$^{-1}$): 3300, 3005, 1725, 1600, 1230

Elemental analysis for $C_{21}H_{28}O_7$ Calculated (%): C64.27; H7.19; O28.54 Found (%): C64.21; H7.31; O28.48

Example 68

Synthesis of 3-hexyloxy-4-hydroxy-8-(2,3-dihydroxypropyloxy)-2H-1-benzopyran-2-one (compound (349))

In the same manner as in Example 12, except that an equimolar amount of 3-hexyloxy-4-hydroxy-8-(2,2-dimethyl-1,3-dioxolane-4-methoxy)-2H-1-benzopyran-2-one obtained in Reference Example 12 was used in place of 3-hexyloxy-4-hydroxy-5-(2,2-dimethyl-1,3-dioxolane-4-methoxy)-2H-1-benzopyran-2-one in Example 12, the titled compound was obtained.

$^1$H-NMR(DMSO-d$_6$, δ-TMS): 10.43(bs, 1H), 6.70–7.50 (m, 3H), 4.95(s, 1H), 4.69(s, 1H), 3.81–4.11(m, 5H), 3.43(s, 2H), 1.70(m, 2H), 1.18–1.40(m, 6H), 0.88(t, 3H, J=7.0 Hz)

IR(KBr, cm$^{-1}$): 3420, 3005, 1680, 1610, 1260

Elemental analysis for $C_{18}H_{24}O_7$ Calculated (%): C61.35; H6.86; O31.78 Found (%): C61.26; H6.99; O31.75

Example 69

Synthesis of 3-butoxy-4-hydroxy-8-(2,3-dihydroxypropyloxy)-2H-1-benzopyran-2-one (compound (348))

In the same manner as in Reference Example 2, except that an equimolar amount of 3-butoxy-4,8-dihydroxy-2H-1-benzopyran-2-one was used in place of 3-hexyloxy-4,5-dihydroxy-2H-1-benzopyran-2-one in Reference Example 2, 3-butoxy-4-hydroxy-8-(2,2-dimethyl-1,3-dioxolane-4-methoxy)-2H-1-benzopyran-2-one was obtained.

In the same manner as in Example 12, except that an equimolar amount of 3-butoxy-4-hydroxy-8-(2,2-dimethyl-1,3-dioxolane-4-methoxy)-2H-1-benzopyran-2-one was used in place of 3-hexyloxy-4-hydroxy-5-(2,2-dimethyl-1,3-dioxolane-4-methoxy)-2H-1-benzopyran-2-one in Example 12, the titled compound was obtained.

$^1$H-NMR(DMSO-d$_6$, δ-TMS): 10.37(bs, 1H), 6.70–7.60 (m, 3H), 5.04(s, 1H), 4.70(s, 1H), 3.81–4.11(m, 5H), 3.44(s, 2H), 1.18–1.40(m, 4H), 0.89(t, 3H, J=7.0 Hz)

IR(KBr, cm$^{-1}$): 3420, 3005, 1680, 1610, 1260

Elemental analysis for $C_{16}H_{20}O_7$ Calculated (%): C59.25; H6.22; O34.53 Found (%): C59.22; H6.36; O34.42

Reference Example 13

Synthesis of 3-hexyloxy-4-hydroxy-8-ethoxycarbonylmethoxy-2H-1-benzopyran-2-one

In the same manner as in Reference Example 3, except that 3-hexyloxy-4,8-dihydroxy-2H-1-benzopyran-2-one was used in place of 3-hexyloxy-4,5-dihydroxy-2H-1-benzopyran-2-one in Reference Example 3, the titled compound was obtained.

$^1$H-NMR(DMSO-d$_6$, δ-TMS): 10.41(bs, 1H), 6.70–7.50 (m, 3H), 4.90(s, 2H), 3.81–4.11(m, 4H), 1.69(m, 2H), 1.20–1.40(m, 9H), 0.87(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.54; H6.59; O30.87

Example 70

Synthesis of 3-hexyloxy-4-hydroxy-8-hydroxycarbonylmethoxy-2H-1-benzopyran-2-one (compound (368))

In the same manner as in Example 14, except that an equimolar amount of 3-hexyloxy-4-hydroxy-8-ethoxycarbonylmethoxy-2H-1-benzopyran-2-one obtained in Reference Example 13 was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.12(bs, 1H), 10.40(bs, 1H), 6.80–7.70(m, 3H), 4.86(s, 2H), 3.89(t, 2H, J=5.0 Hz), 1.69(m, 2H), 1.20–1.40(m, 6H), 0.88(t, 3H, J=7.0 Hz)

IR(KBr, cm$^{-1}$): 3420, 3005, 1750, 1610, 1260

Elemental analysis for $C_{17}H_{20}O_7$ Calculated (%): C60.71; H5.99; O33.30 Found (%): C60.69; H6.07; O33.24

Example 71

Synthesis of 3-ethoxy-4-hydroxy-8-hydroxycarbonylmethoxy-2H-1-benzopyran-2-one (compound (362))

In the same manner as in Reference Example 3, except that an equimolar amount of 3-ethoxy-4,8-dihydroxy-2H-1-benzopyran-2-one obtained in Reference Example 13 was used in place of 3-hexyloxy-4,5-dihydroxy-2H-1-benzopyran-2-one in Reference Example 3, 3-ethoxy-4-hydroxy-8-ethoxycarbonylmethoxy-2H-1-benzopyran-2-one was obtained.

In the same manner as in Example 14, except that an equimolar amount of 3-ethoxy-4-hydroxy-8-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.14(bs, 1H), 10.36(bs, 1H), 6.80–7.60(m, 3H), 4.86(s, 2H), 4.08(q, 2H, J=6.0 Hz), 1.27(t, 3H, J=7.0 Hz)

IR(KBr, cm$^{-1}$): 3420, 3005, 1750, 1610, 1260

Elemental analysis for $C_{13}H_{12}O_7$ Calculated (%): C55.72; H4.32; O39.97 Found (%): C55.67; H4.28; O40.05

Example 72

Synthesis of 3-butoxy-4-hydroxy-8-hydroxycarbonylmethoxy-2H-1-benzopyran-2-one (compound (365))

In the same manner as in Reference Example 3, except that an equimolar amount of 3-butoxy-4,8-dihydroxy-2H-1-benzopyran-2-one was used in place of 3-hexyloxy-4,5-dihydroxy-2H-1-benzopyran-2-one in Reference Example 3, 3-butoxy-4-hydroxy-8-ethoxycarbonylmethoxy-2H-1-benzopyran-2-one was obtained.

In the same manner as in Example 14, except that an equimolar amount of 3-butoxy-4-hydroxy-8-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.14(bs, 1H), 10.37(bs, 1H), 6.80–7.60(m, 3H), 4.86(s, 2H), 3.98(t, 2H, J=6.0 Hz), 1.30–1.95(m, 4H), 0.87(t, 3H, J=7.0 Hz)

IR(KBr, cm$^{-1}$): 3420, 3005, 1750, 1610, 1260

Elemental analysis for $C_{15}H_{16}O_7$ Calculated (%): C58.44; H5.23; O36.33 Found (%): C58.50; H5.11; O36.39

Example 73

Synthesis of 3-octyloxy-4-hydroxy-8-hydroxycarbonylmethoxy-2H-1-benzopyran-2-one (compound (374))

In the same manner as in Reference Example 3, except that an equimolar amount of 3-octyloxy-4,8-dihydroxy-2H-1-benzopyran-2-one was used in place of 3-hexyloxy-4,5-dihydroxy-2H-1-benzopyran-2-one in Reference Example 3, 3-octyloxy-4-hydroxy-8-ethoxycarbonylmethoxy-2H-1-benzopyran-2-one was obtained.

In the same manner as in Example 14, except that an equimolar amount of 3-octyloxy-4-hydroxy-8-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.16(bs, 1H), 10.41(bs, 1H), 6.80–7.60(m, 3H), 4.89(s, 2H), 3.95(t, 2H, J=6.0 Hz), 1.30–1.95(m, 12H), 0.87(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.67; H6.71; O30.62

Example 74

Synthesis of 3-geranyloxy-4-hydroxy-8-hydroxycarbonylmethoxy-2H-1-benzopyran-2-one (compound (384))

In the same manner as in Reference Example 3, except that an equimolar amount of 3-geranyloxy-4,8-dihydroxy-2H-1-benzopyran-2-one was used in place of 3-hexyloxy-4,5-dihydroxy-2H-1-benzopyran-2-one in Reference Example 3, 3-octyloxy-4-hydroxy-8-ethoxycarbonylmethoxy-2H-1-benzopyran-2-one was obtained.

In the same manner as in Example 14, except that an equimolar amount of 3-geranyloxy-4-hydroxy-8-ethoxycarbonylmethoxy-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.19(bs, 1H), 10.36(bs, 1H), 6.80–7.60(m, 3H), 5.39(m, 1H), 5.24(m, 1H), 5.10(m, 1H), 4.87(s, 2H), 4.25(m, 2H), 4.05(t, 2H, J=6.0 Hz), 3.79(t, 2H, J=6.0 Hz), 1.50–2.15(m, 13H)

IR(KBr, cm$^{-1}$): 3420, 3005, 1750, 1610, 1260

Elemental analysis for $C_{21}H_{24}O_7$ Calculated (%): C64.93; H6.23; O28.84 Found (%): C64.87; H6.34; O28.79

Example 75

Synthesis of 3-butoxy-4-hydroxy-8-(2-hydroxycarbonylethoxy)-2H-1-benzopyran-2-one (compound (388))

In the same manner as in Reference Example 3, except that an equimolar amount of 3-butoxy-4,8-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-butoxy-4-hydroxy-8-(2-ethoxycarbonylethoxy)-2H-1-benzopyran-2-one was obtained.

In the same manner as in Example 14, except that an equimolar amount of 3-butoxy-4-hydroxy-8-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-d$_6$, δ-TMS): 11.19(bs, 1H), 10.39(bs, 1H), 6.80–7.60(m, 3H), 4.42(t, 2H, J=5.0 Hz), 3.98(t, 2H, J=6.0 Hz), 3.17(t, 2H, J=5.0 Hz), 1.30–1.95(m, 4H), 0.87(t, 3H, J=7.0 Hz)

IR(KBr, cm$^{-1}$): 3420, 3005, 1750, 1610, 1260

Elemental analysis for $C_{16}H_{18}O_7$ Calculated (%): C59.62; H5.63; O34.75 Found (%): C59.69; H5.44; O34.87

Example 76

Synthesis of 3-hexyloxy-4-hydroxy-8-(2-hydroxycarbonylethoxy)-2H-1-benzopyran-2-one (compound (389))

In the same manner as in Reference Example 3, except that an equimolar amount of 3-hexyloxy-4,8-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-hexyloxy-4-hydroxy-8-(2-ethoxycarbonylethoxy)-2H-1-benzopyran-2-one was obtained.

In the same manner as in Example 14, except that an equimolar amount of 3-hexyloxy-4-hydroxy-8-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.12(bs, 1H), 10.38(bs, 1H), 6.80–7.60(m, 3H), 4.46(t, 2H, J=5.0 Hz), 3.99(t, 2H, J=6.0 Hz), 3.20(t, 2H, J=5.0 Hz), 1.69(m, 2H), 1.30–1.95(m, 8H), 0.88(t, 3H, J=7.0 Hz)

IR(KBr, cm$^{-1}$): 3420, 3005, 1750, 1610, 1260

Elemental analysis for $C_{18}H_{22}O_7$ Calculated (%): C61.70; H6.33; O31.97 Found (%): C61.64; H6.47; O31.89

Example 77

Synthesis of 3-octyloxy-4-hydroxy-8-(2-hydroxycarbonylethoxy)-2H-1-benzopyran-2-one (compound (390))

In the same manner as in Reference Example 3, except that an equimolar amount of 3-octyloxy-4,8-dihydroxy-2H-1-benzopyran-2-one was used in place of 3-hexyloxy-4,5-dihydroxy-2H-1-benzopyran-2-one, and ethyl 3-bromopropionate was used in place of ethyl bromoacetate in Reference Example 3, 3-octyloxy-4-hydroxy-8-(2-ethoxycarbonylethoxy)-2H-1-benzopyran-2-one was obtained.

In the same manner as in Example 14, except that an equimolar amount of 3-octyloxy-4-hydroxy-8-(2-ethoxycarbonylethoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.14(bs, 1H), 10.36(bs, 1H), 6.80–7.60(m, 3H), 4.41(t, 2H, J=5.0 Hz), 3.97(t, 2H, J=6.0 Hz), 3.20(t, 2H, J=5.0 Hz), 1.68(m, 2H), 1.30–1.95(m, 12H), 0.88(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.53; H6.81; O29.66

Example 78

Synthesis of 3-hexyloxy-4-hydroxy-8-(3-hydroxycarbonylpropyloxy)-2H-1-benzopyran-2-one (compound (396))

In the same manner as in Reference Example 3, except that an equimolar amount of 3-hexyloxy-4,8-dihydroxy-2H-1-benzopyran-2-one was used in place of 3-hexyloxy-4,5-dihydroxy-2H-1-benzopyran-2-one, and ethyl 3-bromobutanoate was used in place of ethyl bromoacetate in Reference Example 3, 3-hexyloxy-4-hydroxy-8-(3-ethoxycarbonylpropyloxy)-2H-1-benzopyran-2-one was obtained.

In the same manner as in Example 14, except that an equimolar amount of 3-hexyloxy-4-hydroxy-8-(3-ethoxycarbonylpropyloxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.17(bs, 1H), 10.44(bs, 1H), 6.80–7.60(m, 3H), 4.41(t, 2H, J=5.0 Hz), 3.99(t, 2H, J=6.0 Hz), 2.27(t, 2H, J=5.0 Hz), 1.30–2.00(m, 10H), 0.88(t, 3H, J=7.0 Hz)

IR(KBr, cm$^{-1}$): 3420, 3005, 1750, 1610, 1260

Elemental analysis for $C_{19}H_{24}O_7$ Calculated (%): C62.62; H6.64; O30.73 Found (%): C62.64; H6.51; O30.85

Example 79

Synthesis of 3-hexyloxy-4-hydroxy-8-(4-hydroxycarbonylbutoxy)-2H-1-benzopyran-2-one (compound (402)))

In the same manner as in Reference Example 3, except that an equimolar amount of 3-hexyloxy-4,8-dihydroxy-2H-1-benzopyran-2-one was used in place of 3-hexyloxy-4,5-dihydroxy-2H-1-benzopyran-2-one, and ethyl 3-bromopentanoate was used in place of ethyl bromoacetate in Reference Example 3, 3-hexyloxy-4-hydroxy-8-(4-ethoxycarbonylbutoxy)-2H-1-benzopyran-2-one was obtained.

In the same manner as in Example 14, except that an equimolar amount of 3-hexyloxy-4-hydroxy-8-(4-ethoxycarbonylbutoxy)-2H-1-benzopyran-2-one was used in place of 3-hexyloxy-4-hydroxy-5-ethoxycarbonylmethoxy-2H-1-benzopyran-2-one in Example 14, the titled compound was obtained.

$^1$H-NMR(DMSO-$d_6$, δ-TMS): 11.19(bs, 1H), 10.47(bs, 1H), 6.80–7.60(m, 3H), 4.41(t, 2H, J=5.0 Hz), 3.99(t, 2H, J=6.0 Hz), 2.23(t, 2H, J=5.0 Hz), 1.30–2.00(m, 12H), 0.86(t, 3H, J=7.0 Hz)

IR(KBr, cm$^{-1}$): 3420, 3005, 1750, 1610, 1260

Elemental analysis for $C_{20}H_{26}O_7$ Calculated (%): C63.48; H6.93; O29.60 Found (%): C63.45; H7.03; O29.52

Example 80

Acute Toxicity Test in Mice

Each of the suspensions of compounds (1)–(404) in 0.5% methyl cellulose was forcibly administered orally at dosages of 1000 and 2000 mg/kg to male ICR mice (body weight of 20–25 g, 5 mice per group), using an esophageal sound.

After administration, the animals were kept in cages for 7 days to observe general symptoms and to count the number of animals that died. a lethal dosage ($LD_{50}$: mg/kg) was extrapolated from the mortality rate at the 7th day after administration. As a result, the $LD_{50}$ of compounds (1)–(404) were over 1000 mg/kg, and therefore it was clearly shown that the benzopyran derivative represented by the general formula (I) is markedly safer.

Example 81

Antiallergic Test due to Antigen-Induced Immediate Type Airway Reaction and Delayed Type Airway Reaction Test Procedure Using an ultrasonic nebulizer (NE-U12, manufactured by OMRON Corporation), male Hartley guinea pigs (aged six weeks) were actively sensitized by consecutive 8-day inhalation of a 1 wt % physiological saline of egg-white albumin for 10 minutes a day. After one week passed since the final sensitization, an asthmatic disease state was induced by inhalation of a 2 wt % physiological saline of egg-white albumin for 5 minutes in the same manner. To inhibit the synthesis of endogenous steroid, metyrapone (10 mg/kg) was intravenously administered at 24 hours and one hour before the induction. To inhibit anaphylactic shock, pyrilamine (10 mg/kg) was intraperitoneally administered 30 minutes before inducing the asthmatic reaction.

After inducing the asthmatic reaction, the airway resistance (specific airway resistance $R_{aw}$) was measured for 1 minute before inducing the asthmatic reaction, and 1 minute, 2 hours, 4 hours, 5 hours, 6 hours, 7 hours, 8 hours, and 23–24 hours after inducing the asthmatic reaction, using an airway resistance measuring apparatus (Pulmos-I, manufactured by M.I.P.S.). An average value of the airway resistance was determined, and an airway resistance increase ratio with respect to the value of the airway resistance before the induction was calculated by the following Equation 1.

Each of the test substances (10 mg/kg) listed in Table 1 was suspended in an aqueous 0.5% methyl cellulose solution, and the suspension was orally administered once one hour before inducing the asthmatic reaction. A positive control substance (prednisolone) was orally administered twice at a dosage of 10 mg/kg 16 hours and 2 hours before inducing the asthmatic reaction. The test was carried out on 8 animals per group.

According to this test procedure, a two-phase increase in airway resistance was observed immediately after inducing the asthmatic reaction and after 4–8 hours passed since inducing the asthmatic reaction. In the present invention, the former increase in airway resistance is referred to as the immediate type asthmatic reaction, while the latter increase in airway resistance is referred to as the delayed type asthmatic reaction. With respect to the evaluation of the drug, for the immediate type asthmatic reaction, the inhibition percentage with respect to the asthmatic reaction inhibiting medium administration group (referring to the group wherein a test drug is not administered after inducing the asthmatic reaction, hereinafter merely referred to as the "medium administration group") was determined by Equation 2 using the airway resistance increase ratio after one minute gas passed since the induction as an index. The results are summarized in Table 1.

For the delayed type asthmatic reaction, the inhibition percentage with respect to the medium administration group was determined by the following Equation 3 using the area under the curve ($AUC_{4-8}$) of the airway resistance increase ratio up to 4–8 hours after inducing the asthmatic reaction as an index. The results are summarized in Table 1. As an example, the relationship between the airway resistance increase ratio up to 4–8 hours after inducing the asthmatic reaction of the delayed type asthmatic reaction and time in the medium administration group, the prednisolone administration group, and the compound (216) administration group is shown in FIG. 1. As used herein, the area under the curve showing the relationship between the airway resistance increase ratio and time is ($AUC_{4-8}$)

Equation 1

> Airway resistance increase ratio (%)=(airway resistance after inducing the asthmatic airway resistance−airway resistance before inducing the asthmatic reaction)/(airway resistance before inducing the asthmatic reaction)×100

Equation 2

> Inhibition (%)=(1−airway resistance increase ratio after one minute has passed since inducing the asthmatic reaction of the test substance administration group/airway resistance increase ratio after one minute has passed since inducing the asthmatic reaction of the medium administration group)×100

Equation 3

> Inhibition (%)=[(1−$AUC_{4-8}$ of the test substance administration group)/($AUC_{4-8}$ after one minute has passed since inducing the asthmatic reaction of the medium administration group)]×100

As comparative compounds, the following six kinds of compounds and prednisolone were used.

Comparative compound (1): 3,4-dihydroxy-7-methoxy-2H-1-benzopyran-2-one described in Example 28 of WO92/13852.

Comparative compound (2): 3-methoxy-4-hydroxy-7-decyloxy-2H-1-benzopyran-2-one described in Example 62 of WO92/13852.

Comparative compound (3): 3-hydroxy-4-butoxy-8-decyloxy-2H-1-benzopyran-2-one described in Example 148 of WO92/13852.

Comparative compound (4): 7-methoxy-4-hydroxy-3-(β-D-glucopyranosyl)-2H-1-benzopyran-2-one described in Example 3 of Japanese Unexamined Patent Application, First Publication No. Hei 7-145189 (U.S. Pat. No. 5,525,595).

Comparative compound (5): 7-butoxy-3-hydroxy-4-(β-D-glucopyranosyl)-2H-1-benzopyran-2-one described in Example 6 of Japanese Unexamined Patent Application, First Publication No. Hei 7-145190 (Example 61 of U.S. Pat. No. 5,525,595).

Comparative compound (6): 3-hydroxy-4-hexyloxy-7-(β-D-glucopyranosyl)-2H-1-benzopyran-2-one described in Example 19 of Japanese Unexamined Patent Application, First Publication No. Hei 8-198890 (U.S. Pat. No. 5,580,552).

TABLE 1

| Compound | Inhibition (%) against immediate type allergy | Inhibition (%) against delayed type allergy |
|---|---|---|
| Compound (8) | 14.1 | 58.2 |
| Compound (14) | 32.4 | 65.5 |
| Compound (29) | 15.8 | 60.9 |
| Compound (53) | 19.3 | 59.8 |
| Compound (65) | 21.5 | 60.2 |
| Compound (81) | 15.4 | 54.1 |
| Compound (99) | 14.6 | 61.9 |
| Compound (109) | 14.0 | 66.8 |
| Compound (115) | 31.8 | 61.7 |
| Compound (137) | 8.3 | 58.9 |
| Compound (147) | 19.1 | 59.5 |
| Compound (166) | 23.5 | 64.1 |
| Compound (202) | 19.9 | 57.8 |
| Compound (207) | 8.5 | 71.7 |
| Compound (210) | 14.2 | 71.4 |
| Compound (216) | 38.8 | 72.5 |
| Compound (226) | 22.8 | 61.5 |
| Compound (249) | 28.8 | 63.4 |
| Compound (267) | 14.0 | 62.2 |
| Compound (273) | 32.9 | 64.5 |
| Compound (288) | 13.4 | 59.1 |
| Compound (311) | 11.9 | 55.4 |
| Compound (349) | 12.5 | 57.2 |
| Compound (368) | 24.8 | 60.0 |
| Compound (390) | 29.7 | 61.1 |
| Comparative Compound (1) | 5.7 | 21.9 |

TABLE 1-continued

| Compound | Inhibition (%) against immediate type allergy | Inhibition (%) against delayed type allergy |
|---|---|---|
| Comparative Compound (2) | 6.5 | 20.2 |
| Comparative Compound (3) | 5.2 | 24.3 |
| Comparative Compound (4) | 4.7 | 20.5 |
| Comparative Compound (5) | 6.8 | 22.4 |
| Comparative Compound (6) | 5.9 | 24.1 |
| Prednisolone | 29.0 | 51.4 |

As is apparent from the results shown in Table 1, the benzopyran derivative represented by the general formula (I) exhibited an inhibition effect of 8.3 to 38.8% against the immediate type asthmatic reaction and also exhibited a strong inhibition effect of 54.1 to 72.5% against the delayed type asthmatic reaction. This inhibition effect was stronger than that of the benzopyran derivative reported previously by the present inventors as the comparative compound, and was the same or higher than that of a steroid positive control substance. As is apparent from the above description, the benzopyran derivative represented by the general formula (I) exerts an excellent therapeutic effect against allergic diseases such as asthma and is useful as an antiallergic agent.

Next, Formulation Examples of the antiallergic agent containing the benzopyran derivative represented by the general formula (I) as the active ingredient are shown below.

Example 82

5% Powder 50 mg of compound (8) was pulverized in a mortar and thoroughly mixed with 950 mg of lactose while pulverizing with a pestle to obtain a powder containing 5% by weight of compound (8) of the present invention.

In the same manner as described above, except that each of compounds (14), (29), (53), (109), (137), (147), (166), (207), (210), (216), (249), (273), and (349) was used in place of compound (8), powders containing 5% by weight of compound (8) were obtained.

Example 83

10% Powder 100 mg of compound (8) was pulverized in a mortar and thoroughly mixed with 900 mg of lactose while pulverizing with a pestle to obtain a powder containing 10% by weight of compound (8) of the present invention.

In the same manner as described above, except that each of compounds (14), (29), (53), (109), (137), (147), (166), (207), (210), (216), (249), (273), and (349) was used in place of compound (8), powders containing 10% by weight of compound (8) were obtained.

Example 84

10% Granule 300 mg of compound (8) and 300 mg of starch were mixed and pulverized in a mortar. To the mixture, 2000 mg of lactose and 370 mg of starch were added and then mixed. Separately, a gelatin solution was prepared by adding 1 ml of pure water to 30 mg of gelatin, dissolving with heating, cooling the solution and adding 1 ml of ethanol, and then this was added to the previously prepared mixture and kneaded. After granulating, the mixture was dried and sifted to obtain granules containing 10% by weight of compound (8).

In the same manner as described above, except that each of compounds (14), (109), (115), (207), (210), (216), and (311) was used in place of compound (8), granules containing 10% by weight of each compound were obtained.

Example 85

5 mg Tablet 100 mg of crystals of the compound were pulverized. To this powders, 1240 mg of lactose and 400 mg of starch were added and then mixed. 2000 mg of 10% starch was added to the mixture and then kneaded. After granulating and drying, 40 mg of talc and 20 mg of magnesium stearate were added, and the resulting mixture was made into tablets by a conventional method at a dosage of 100 mg/tablet to obtain tablets containing 5 mg of compound (8).

In the same manner as described above, except that each of compounds (14), (109), (115), (207), (210), (216), (267), (273), and (311) was used in place of compound (8), tablets containing 5 mg of the compound were obtained.

Example 86

20 mg Tablet 6 g of hydroxypropyl cellulose was dissolved in an appropriate amount of ethanol and was kneaded with 94 g of lactose. The mixture was lightly dried, sifted through a sieve No. 60 to obtain 6% hydroxypropyl cellulose lactose. Magnesium was mixed with talc at a mixing ratio of 1:4 to obtain talc stearate. 200 mg of compound (8), 750 mg of 6% hydroxypropyl cellulose lactose, 20 mg of talc stearate, and 30 mg of potato starch were thoroughly mixed and made into tablets by a conventional method at a dosage of 100 mg/tablet to obtain tablets containing 20 mg of compound (8).

In the same manner as described above, except that each of compounds (14), (109), (115), (207), (210), (216), (267), (273), and (311) was used in place of compound (8), tablets containing 20 mg of the compound were obtained.

Example 87

25 mg Tablet 250 mg of compound (8) was pulverized in a mortar and then thoroughly mixed while adding 1220 g of lactose. An appropriate amount of pure water was added to 500 mg of carboxymethyl starch, and this was added to the previously prepared mixture and kneaded, followed by granulation. After drying, 20 mg of talc and 10 mg of magnesium stearate were mixed and made into tablets by a conventional method at a dosage of 200 mg/tablet to obtain tablets containing 25 mg of compound (8).

In the same manner as described above, except that each of compounds (14), (115), (208), (210), (216), (267), (311), and (349) was used in place of compound (8), tablets containing 25 mg of the compound were obtained.

Example 88

10 mg Capsule

In the same manner as in Example 84, 300 mg of compound (8), 2000 mg of lactose, 670 mg of starch, and 30 mg of gelatin were mixed and formed into granules, and then the granules were packed in a capsule No. 4 at a dosage of 100 mg/capsule to obtain capsules containing 10 mg of compound (8).

In the same manner as described above, except that each of compounds (14), (109), (115), (208), (210), (216), (267), (311), and (349) was used in place of compound (8), capsules containing 10 mg of the compound were obtained.

Example 89

0.5% Ointment 5 mg of compound (208) and a small amount of liquid paraffin were levigated in a mortar to form a dispersion. Separately, a base was prepared by mixing 915 mg of white soft paraffin with liquid paraffin in such an amount as to make the total amount with previously used liquid paraffin to be 80 mg while heating. To this base, the previously prepared dispersion was gradually added, followed by uniform mixing while thoroughly kneading to obtain ointments containing 0.5% by weight of compound (208).

In the same manner as described above, except that each of compounds (210), (216), (267), (311), and (349) was used in place of compound (208), ointments containing 0.5 mg of the compound were obtained.

What is claimed is:

1. A method for treating allergies, comprising the step of administering to a patient afflicted with an allergic condition a pharmaceutically effective amount of an antiallergic agent including a benzopyran derivative represented by the general formula (I):

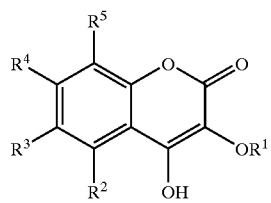

(I)

wherein $R^1$ is an alkyl group having 1–10 carbon atoms or an alkenyl group having 2–10 carbon atoms, and one of $R^2$, $R^3$, $R^4$, and $R^5$ is an alkoxy group substituted with a hydroxy group or an alkoxy group substituted with a carboxy group, and the others are hydrogen atoms, or physiologically acceptable salts thereof as the active ingredient.

2. The method according to claim 1, wherein $R^1$ is an alkyl group having 1–10 carbon atoms, and $R^2$ is an alkoxy group having 1–4 carbon atoms substituted with one or two hydroxy groups, or an alkoxy group having 1–4 carbon atoms substituted with one carboxy group, in the general formula (I).

3. The method according to claim 1, wherein $R^1$ is an alkyl group having 1–10 carbon atoms, and $R^3$ is an alkoxy group having 1–4 carbon atoms substituted with one or two hydroxy groups, or an alkoxy group having 1–4 carbon atoms substituted with one carboxy group, in the general formula (I).

4. The method according to claim 1, wherein $R^1$ is an alkyl group having 1–10 carbon atoms, and $R^4$ is an alkoxy group having 1–4 carbon atoms substituted with one or two hydroxy groups, or an alkoxy group having 1–4 carbon atoms substituted with one carboxy group, in the general formula (I).

5. The method according to claim 1, wherein $R^1$ is an alkyl group having 1–10 carbon atoms, and $R^5$ is an alkoxy group having 1–4 carbon atoms substituted with one or two hydroxy groups, or an alkoxy group having 1–4 carbon atoms substituted with one carboxy group, in the general formula (I).

6. The method according to claim 1, wherein $R^1$ is an alkenyl group having 2–10 carbon atoms, and $R^2$ is an alkoxy group having 1–4 carbon atoms substituted with one or two hydroxy groups, or an alkoxy group having 1–4 carbon atoms substituted with one carboxy group, in the general formula (I).

7. The method according to claim 1, wherein $R^1$ is an alkenyl group having 2–10 carbon atoms, and $R^3$ is an alkoxy group having 1–4 carbon atoms substituted with one or two hydroxy groups, or an alkoxy group having 1–4 carbon atoms substituted with one carboxy group, in the general formula (I).

8. The method according to claim 1, wherein $R^1$ is an alkenyl group having 2–10 carbon atoms, and $R^4$ is an alkoxy group having 1–4 carbon atoms substituted with one or two hydroxy groups, or an alkoxy group having 1–4 carbon atoms substituted with one carboxy group, in the general formula (I).

9. The method according to claim 1, wherein $R^1$ is an alkenyl group having 2–10 carbon atoms, and $R^5$ is an alkoxy group having 1–4 carbon atoms substituted with one or two hydroxy groups, or an alkoxy group having 1–4 carbon atoms substituted with one carboxy group, in the general formula (I).

10. A method for treating allergies, comprising the step of administering to a patient afflicted with an allergic condition a pharmaceutically effective amount of a benzopyran derivative represented by the general formula (II):

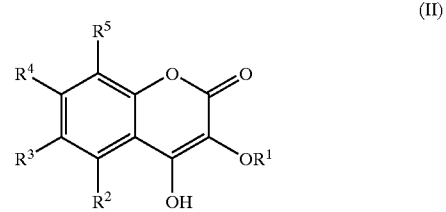

(II)

wherein $R^1$ is an alkyl group having 1–10 carbon atoms or an alkenyl group having 2–10 carbon atoms, and one of $R^2$, $R^3$, $R^4$, and $R^5$ is an alkoxy group substituted with a carboxy group, and the others are hydrogen atoms.

11. The method according to claim 10, wherein $R^1$ is an alkyl group having 1–10 carbon atoms, and $R^2$ is an alkoxy group having 1–4 carbon atoms substituted with one carboxy group, in the general formula (II).

12. The method according to claim 10, wherein $R^1$ is an alkyl group having 1–10 carbon atoms, and $R^3$ is an alkoxy group having 1–4 carbon atoms substituted with one carboxy group, in the general formula (II).

13. The method according to claim 10, wherein $R^1$ is an alkyl group having 1–10 carbon atoms, and $R^4$ is an alkoxy group having 1–4 carbon atoms substituted with one carboxy group, in the general formula (II).

14. The method according to claim 10, wherein $R^1$ is an alkyl group having 1–10 carbon atoms, and $R^5$ is an alkoxy group having 1–4 carbon atoms substituted with one carboxy group, in the general formula (II).

15. The method according to claim 10, wherein $R^1$ is an alkenyl group having 2–10 carbon atoms, and $R^2$ is an alkoxy group having 1–4 carbon atoms substituted with one carboxy group, in the general formula (II).

16. The method according to claim 10, wherein $R^1$ is an alkenyl group having 2–10 carbon atoms, and $R^3$ is an alkoxy group having 1–4 carbon atoms substituted with one carboxy group, in the general formula (II).

17. The method according to claim 10, wherein $R^1$ is an alkenyl group having 2–10 carbon atoms, and $R^4$ is an alkoxy group having 1–4 carbon atoms substituted with one carboxy group, in the general formula (II).

18. The method according to claim 10, wherein $R^1$ is an alkenyl group having 2–10 carbon atoms, and $R^5$ is an alkoxy group having 1–4 carbon atoms substituted with one carboxy group in the general formula (II).

19. A method for treating allergies, comprising the steps of:

providing an antiallergic agent comprising a benzopyran derivative represented by the general formula (I):

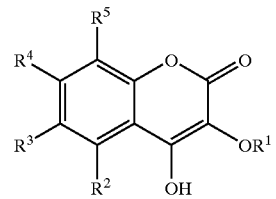

(I)

wherein $R^1$ is an alkyl group having 1–10 carbon atoms or an alkenyl group having 2–10 carbon atoms, one of $R^2$, $R^3$, $R^4$, and $R^5$ is an alkoxy group substituted with a hydroxy group or an alkoxy group substituted with a carboxy group, and the others are hydrogen atoms, or physiologically acceptable salts thereof for preparation of an antiallergic agent.

* * * * *